United States Patent
Dibenedetto et al.

(10) Patent No.: US 11,562,417 B2
(45) Date of Patent: Jan. 24, 2023

(54) RETAIL STORE MOTION SENSOR SYSTEMS AND METHODS

(71) Applicant: adidas AG, Herzogenaurach (DE)

(72) Inventors: Christian Dibenedetto, North Plains, OR (US); Amy Jones Vaterlaus, Portland, OR (US); Ben Valenti, Portland, OR (US); Aurel Coza, Portland, OR (US)

(73) Assignee: adidas AG, Herzogenaurach (DE)

( * ) Notice: Subject to any disclaimer, the term of this patent is extended or adjusted under 35 U.S.C. 154(b) by 440 days.

(21) Appl. No.: 14/579,226

(22) Filed: Dec. 22, 2014

(65) Prior Publication Data

US 2016/0180440 A1    Jun. 23, 2016

(51) Int. Cl.
*G06Q 30/06* (2012.01)
*A61B 5/11* (2006.01)
(Continued)

(52) U.S. Cl.
CPC .......... *G06Q 30/0631* (2013.01); *A61B 5/112* (2013.01); *G06Q 30/02* (2013.01); *G16H 20/30* (2018.01)

(58) Field of Classification Search
CPC ......... A61B 5/112; G06F 19/34; G06Q 30/02; G06Q 30/0631; G16H 20/30
(Continued)

(56) References Cited

U.S. PATENT DOCUMENTS

| | | |
|---|---|---|
| 4,202,350 A | 5/1980 | Walton |
| 4,312,358 A | 1/1982 | Barney |

(Continued)

FOREIGN PATENT DOCUMENTS

| | | |
|---|---|---|
| CN | 103372298 A | 10/2013 |
| EP | 1134555 A1 | 9/2001 |

(Continued)

OTHER PUBLICATIONS

Porta, J.P., 2013. Validating the Adidas miCoach and Nike+ Sport Kit for estimating pace, distance, and energy expenditure during over-ground exercise, The University of Texas at El Paso. (Year: 2013).*

(Continued)

*Primary Examiner* — Matthew E Zimmerman
*Assistant Examiner* — Latasha D Ramphal
(74) *Attorney, Agent, or Firm* — Sterne, Kessler, Goldstein & Fox P.L.L.C.

(57) ABSTRACT

A method for providing a recommendation to an individual about an article of footwear includes receiving data about the individual from a sensor module associated with the individual during a first athletic activity engaged in by the individual, determining a first characteristic about the individual's gait based on the data related to the first athletic activity, providing a recommendation about a first article of footwear to the individual based on the first characteristic, receiving data about the individual from the sensor module associated with the individual during a second athletic activity engaged in by the individual, determining a second characteristic about the individual's gait based on the data related to the second athletic activity, comparing the first characteristic with the second characteristic, and providing a recommendation about a second article of footwear to the individual based on the comparison.

19 Claims, 31 Drawing Sheets

(51) Int. Cl.
*G06Q 30/02* (2012.01)
*G16H 20/30* (2018.01)

(58) Field of Classification Search
USPC .......................................................... 705/26
See application file for complete search history.

(56) References Cited

U.S. PATENT DOCUMENTS

| | | | |
|---|---|---|---|
| 4,572,197 A | 2/1986 | Moore et al. | |
| 4,580,572 A | 4/1986 | Granek et al. | |
| 4,889,131 A | 12/1989 | Salem et al. | |
| 4,909,260 A | 3/1990 | Salem et al. | |
| 4,962,469 A | 10/1990 | Ono et al. | |
| 5,007,427 A | 4/1991 | Ramsey et al. | |
| 5,111,818 A | 5/1992 | Ramsey et al. | |
| 5,148,002 A | 9/1992 | Kuo et al. | |
| 5,153,584 A | 10/1992 | Engira | |
| 5,204,670 A | 4/1993 | Stinton | |
| 5,210,540 A | 5/1993 | Masumoto | |
| 5,353,793 A | 10/1994 | Bomn | |
| 5,400,254 A | 3/1995 | Fujita | |
| 5,583,776 A | 12/1996 | Levi et al. | |
| 5,592,401 A | 1/1997 | Kramer | |
| 5,611,085 A | 3/1997 | Rasmussen | |
| 5,724,025 A | 3/1998 | Tavori | |
| 5,724,265 A | 3/1998 | Hutchings | |
| 5,769,755 A | 6/1998 | Henry et al. | |
| 5,802,492 A | 9/1998 | DeLorme et al. | |
| 5,825,327 A | 10/1998 | Krasner | |
| 5,899,963 A | 5/1999 | Hutchings | |
| 5,947,868 A | 9/1999 | Dugan | |
| 5,948,040 A | 9/1999 | DeLorme et al. | |
| 5,955,667 A | 9/1999 | Fyfe | |
| 5,976,083 A | 11/1999 | Richardson et al. | |
| 5,989,157 A | 11/1999 | Walton | |
| 6,002,982 A | 12/1999 | Fry | |
| 6,013,007 A | 1/2000 | Root et al. | |
| 6,032,108 A | 2/2000 | Seiple et al. | |
| 6,047,203 A | 4/2000 | Sackner et al. | |
| 6,066,093 A | 5/2000 | Kelly et al. | |
| 6,097,345 A | 8/2000 | Walton | |
| 6,122,340 A | 9/2000 | Darley et al. | |
| 6,135,951 A | 10/2000 | Richardson et al. | |
| 6,145,389 A | 11/2000 | Ebeling et al. | |
| 6,148,262 A | 11/2000 | Fry | |
| 6,148,271 A | 11/2000 | Marinelli | |
| 6,151,563 A | 11/2000 | Marinelli | |
| 6,157,898 A | 12/2000 | Marinelli | |
| 6,198,394 B1 | 3/2001 | Jacobsen et al. | |
| 6,204,807 B1 | 3/2001 | Odagiri et al. | |
| 6,246,362 B1 | 6/2001 | Tsubata et al. | |
| 6,254,551 B1 | 7/2001 | Varis | |
| 6,266,623 B1 | 7/2001 | Vock et al. | |
| 6,298,314 B1 | 10/2001 | Blackadar et al. | |
| 6,301,964 B1 | 10/2001 | Fyfe et al. | |
| 6,305,221 B1 | 10/2001 | Flutchings | |
| 6,336,365 B1 | 1/2002 | Blackadar et al. | |
| 6,356,856 B1 | 3/2002 | Damen et al. | |
| 6,357,147 B1 | 3/2002 | Darley et al. | |
| 6,381,482 B1 | 4/2002 | Jayaraman et al. | |
| 6,443,890 B1 | 9/2002 | Schulze | |
| 6,463,385 B1 | 10/2002 | Fry | |
| 6,478,736 B1 | 11/2002 | Mault | |
| 6,493,652 B1 | 12/2002 | Ohlenbusch et al. | |
| 6,513,381 B2 | 2/2003 | Fyfe et al. | |
| 6,513,532 B2 | 2/2003 | Mault et al. | |
| 6,536,139 B2 | 3/2003 | Darley et al. | |
| 6,551,252 B2 | 4/2003 | Sackner et al. | |
| 6,582,330 B1 | 6/2003 | Rehkemper et al. | |
| 6,585,622 B1 | 7/2003 | Shum et al. | |
| 6,590,536 B1 | 7/2003 | Walton | |
| 6,611,789 B1 | 8/2003 | Darley | |
| 6,616,613 B1 | 9/2003 | Goodman | |
| 6,626,799 B2 | 9/2003 | Watterson et al. | |
| 6,716,139 B1 | 4/2004 | Hosseinzadeh-Dolkhani et al. | |
| 6,736,759 B1 | 5/2004 | Stubbs et al. | |
| 6,745,069 B2 | 6/2004 | Nissila et al. | |
| 6,790,178 B1 | 9/2004 | Mault et al. | |
| 6,798,378 B1 | 9/2004 | Walters | |
| 6,832,109 B2 | 12/2004 | Nissila | |
| 6,836,744 B1 | 12/2004 | Asphahani et al. | |
| 6,876,947 B1 | 4/2005 | Darley et al. | |
| 6,882,955 B1 | 4/2005 | Ohlenbusch et al. | |
| 6,885,971 B2 | 4/2005 | Vock et al. | |
| 6,895,341 B2 | 5/2005 | Barrey et al. | |
| 6,898,550 B1 | 5/2005 | Blackadar et al. | |
| 6,959,259 B2 | 10/2005 | Vock et al. | |
| 6,970,731 B1 | 11/2005 | Jayaraman et al. | |
| 7,062,225 B2 | 6/2006 | White | |
| 7,072,789 B2 | 7/2006 | Vock et al. | |
| 7,089,152 B2 | 8/2006 | Oda et al. | |
| 7,092,846 B2 | 8/2006 | Vock et al. | |
| 7,171,331 B2 | 1/2007 | Vock et al. | |
| 7,187,924 B2 | 3/2007 | Ohlenbusch et al. | |
| 7,200,517 B2 | 4/2007 | Darley et al. | |
| 7,220,220 B2 | 5/2007 | Stubbs et al. | |
| 7,251,454 B2 | 7/2007 | White | |
| 7,254,516 B2 | 8/2007 | Case, Jr. et al. | |
| 7,273,431 B2 | 9/2007 | DeVall | |
| 7,292,867 B2 | 11/2007 | Werner et al. | |
| 7,428,472 B2 | 9/2008 | Darley et al. | |
| 7,457,724 B2 | 11/2008 | Vock et al. | |
| 7,467,060 B2 | 12/2008 | Kulach et al. | |
| 7,480,512 B2 | 1/2009 | Graham et al. | |
| 7,503,900 B2 | 3/2009 | Goswami | |
| 7,552,031 B2 | 6/2009 | Vock et al. | |
| 7,559,902 B2 | 7/2009 | Ting et al. | |
| 7,647,196 B2 | 1/2010 | Kahn et al. | |
| 7,650,257 B2 | 1/2010 | Alexander et al. | |
| 7,670,263 B2 | 3/2010 | Ellis et al. | |
| 7,670,295 B2 | 3/2010 | Sackner et al. | |
| 7,680,523 B2 | 3/2010 | Rytky | |
| 7,689,378 B2 | 3/2010 | Kolen | |
| 7,698,830 B2 | 4/2010 | Townsend et al. | |
| 7,706,815 B2 | 4/2010 | Graham et al. | |
| 7,715,982 B2 | 5/2010 | Grenfell et al. | |
| 7,805,149 B2 | 9/2010 | Werner et al. | |
| 7,805,150 B2 | 9/2010 | Graham et al. | |
| 7,827,000 B2 | 11/2010 | Stirling et al. | |
| 7,844,415 B1 | 11/2010 | Bryant et al. | |
| 7,890,291 B2 | 2/2011 | Godin et al. | |
| 7,891,666 B2 | 2/2011 | Kuenzler et al. | |
| 7,938,013 B2 | 5/2011 | Hughes et al. | |
| 7,980,998 B2 | 7/2011 | Shemesh et al. | |
| 8,060,337 B2 | 11/2011 | Kulach et al. | |
| 8,253,586 B1 | 8/2012 | Matak | |
| 8,540,560 B2 | 9/2013 | Crowley et al. | |
| 8,579,632 B2 | 11/2013 | Crowley | |
| 8,818,478 B2 | 8/2014 | Scheffler et al. | |
| 2002/0023087 A1 | 2/2002 | Vickery et al. | |
| 2002/0032386 A1 | 3/2002 | Sackner et al. | |
| 2002/0068873 A1 | 6/2002 | Nissila | |
| 2002/0107433 A1 | 8/2002 | Mault | |
| 2002/0160883 A1 | 10/2002 | Dugan | |
| 2002/0178093 A1* | 11/2002 | Dean | G06Q 30/0641 705/28 |
| 2003/0110095 A1 | 6/2003 | Danenberg | |
| 2003/0163287 A1 | 8/2003 | Vock et al. | |
| 2003/0208409 A1 | 11/2003 | Mault | |
| 2003/0224337 A1 | 12/2003 | Shum et al. | |
| 2004/0046692 A1 | 3/2004 | Robson et al. | |
| 2004/0102931 A1 | 5/2004 | Ellis et al. | |
| 2004/0143452 A1* | 7/2004 | Pattillo | A43D 1/02 600/300 |
| 2004/0171956 A1 | 9/2004 | Babashan | |
| 2004/0177531 A1 | 9/2004 | DiBenedetto et al. | |
| 2004/0199056 A1 | 10/2004 | Husemann et al. | |
| 2004/0209600 A1 | 10/2004 | Werner et al. | |
| 2005/0010096 A1 | 1/2005 | Blackadar | |
| 2005/0049816 A1* | 3/2005 | Oda | A43D 1/025 702/127 |
| 2005/0054941 A1 | 3/2005 | Ting et al. | |
| 2005/0195094 A1 | 9/2005 | White | |
| 2005/0197063 A1 | 9/2005 | White | |

(56) References Cited

U.S. PATENT DOCUMENTS

| | | |
|---|---|---|
| 2005/0227811 A1 | 10/2005 | Shum et al. |
| 2005/0233815 A1 | 10/2005 | McCreary et al. |
| 2005/0250458 A1 | 11/2005 | Graham et al. |
| 2005/0266961 A1 | 12/2005 | Shum et al. |
| 2006/0020421 A1 | 1/2006 | Darley et al. |
| 2006/0025282 A1 | 2/2006 | Redmann |
| 2006/0135297 A1 | 6/2006 | Cruciani |
| 2006/0136173 A1 | 6/2006 | Case, Jr. et al. |
| 2006/0148594 A1 | 7/2006 | Saintoyant et al. |
| 2006/0189360 A1 | 8/2006 | White |
| 2006/0240865 A1 | 10/2006 | White |
| 2006/0246869 A1 | 11/2006 | Ohlenbusch et al. |
| 2007/0006489 A1 | 1/2007 | Case, Jr. et al. |
| 2007/0011919 A1 | 1/2007 | Case, Jr. |
| 2007/0021269 A1* | 1/2007 | Shum ................ A61B 5/11 482/8 |
| 2007/0032318 A1 | 2/2007 | Nishimura et al. |
| 2007/0039209 A1 | 2/2007 | White et al. |
| 2007/0043582 A1 | 2/2007 | Peveto et al. |
| 2007/0059675 A1 | 3/2007 | Kuenzler et al. |
| 2007/0060425 A1 | 3/2007 | Kuenzler et al. |
| 2007/0061105 A1 | 3/2007 | Darley et al. |
| 2007/0191083 A1 | 8/2007 | Kuenzler et al. |
| 2007/0203665 A1 | 8/2007 | Darley et al. |
| 2007/0208531 A1 | 9/2007 | Darley et al. |
| 2007/0247306 A1 | 10/2007 | Case |
| 2007/0287596 A1 | 12/2007 | Case et al. |
| 2008/0009275 A1 | 1/2008 | Werner et al. |
| 2008/0051993 A1 | 2/2008 | Graham et al. |
| 2008/0058971 A1 | 3/2008 | Graham et al. |
| 2008/0059064 A1 | 3/2008 | Werner et al. |
| 2008/0065319 A1 | 3/2008 | Graham et al. |
| 2008/0088303 A1 | 4/2008 | Englert |
| 2008/0103689 A1 | 5/2008 | Graham et al. |
| 2008/0125288 A1 | 5/2008 | Case |
| 2008/0242953 A1* | 10/2008 | Dew ................ G16H 10/60 600/300 |
| 2008/0274844 A1 | 11/2008 | Ward |
| 2008/0319661 A1 | 12/2008 | Werner et al. |
| 2009/0047645 A1 | 2/2009 | Dibenedetto et al. |
| 2009/0048044 A1 | 2/2009 | Oleson et al. |
| 2009/0048070 A1 | 2/2009 | Vincent et al. |
| 2009/0163834 A1 | 6/2009 | Wilssens |
| 2009/0233770 A1 | 9/2009 | Vincent et al. |
| 2009/0292178 A1 | 11/2009 | Ellis et al. |
| 2010/0042427 A1 | 2/2010 | Graham et al. |
| 2010/0063778 A1 | 3/2010 | Schrock et al. |
| 2010/0063779 A1 | 3/2010 | Schrock et al. |
| 2010/0088023 A1 | 4/2010 | Werner |
| 2010/0012599 A1 | 5/2010 | Boeve et al. |
| 2010/0184564 A1 | 7/2010 | Molyneux et al. |
| 2010/0201352 A1 | 8/2010 | Englert |
| 2010/0292050 A1 | 11/2010 | DiBenedetto et al. |
| 2010/0292599 A1 | 11/2010 | Oleson et al. |
| 2010/0292600 A1 | 11/2010 | Dibenedetto et al. |
| 2011/0054270 A1 | 3/2011 | Derchak |
| 2011/0054271 A1 | 3/2011 | Derchak et al. |
| 2011/0054272 A1 | 3/2011 | Derchak |
| 2011/0054290 A1 | 3/2011 | Derchak |
| 2011/0082641 A1 | 4/2011 | Werner et al. |
| 2011/0087115 A1 | 4/2011 | Sackner et al. |
| 2011/0105861 A1 | 5/2011 | Derchak et al. |
| 2011/0119022 A1 | 5/2011 | Kuenzler et al. |
| 2011/0130643 A1 | 6/2011 | Derchak et al. |
| 2012/0223943 A1* | 9/2012 | Williams ............ G06Q 30/06 345/419 |
| 2012/0253484 A1 | 10/2012 | Burich et al. |
| 2012/0254934 A1 | 10/2012 | McBrearty et al. |
| 2013/0041590 A1 | 2/2013 | Burich et al. |
| 2013/0274040 A1 | 10/2013 | Coza et al. |
| 2013/0274635 A1* | 10/2013 | Coza ................ G16H 40/63 600/595 |
| 2013/0274904 A1* | 10/2013 | Coza ................ A63B 71/0619 700/91 |
| 2014/0052567 A1 | 2/2014 | Bhardwaj et al. |
| 2014/0222173 A1* | 8/2014 | Giedwoyn .......... G06F 19/3481 700/91 |
| 2014/0244009 A1* | 8/2014 | Mestas ................ G16H 40/63 700/91 |
| 2015/0031964 A1* | 1/2015 | Bly ................ A61B 5/681 600/301 |
| 2016/0081435 A1* | 3/2016 | Marks ................ A43D 1/027 382/154 |

FOREIGN PATENT DOCUMENTS

| | | |
|---|---|---|
| EP | 2 650 807 A1 | 10/2013 |
| JP | 07-96014 | 10/1995 |
| WO | WO 2002/067449 A2 | 8/2002 |
| WO | WO 2007/001809 A2 | 1/2007 |
| WO | WO 2007/001809 A3 | 1/2007 |
| WO | WO 2012/014110 A2 | 2/2012 |
| WO | WO-2012021507 A2 * | 2/2012 ........ A61B 5/0002 |
| WO | WO 2014/028765 A2 | 2/2014 |

OTHER PUBLICATIONS

The Extended European Search Report issued in European Patent Application No. EP 15 19 9781, 7 pages, dated Mar. 3, 2016.

Lomas, N., "RunScribe Is A Wearable For Granular Gait Analysis," published Sep. 1, 2014, accessed at http://techcrunch.com/2014/09/01/runscribe/, accessed on Dec. 12, 2014.

Yun, X., et al., "A Simplified Quaternion-Based Algorithm for Orientation Estimation From Earth Gravity and Magnetic Field Measurements," IEEE Transactions on Instrumentation and Measurement, vol. 57, No. 3, pp. 638-650, Mar. 2008.

Shead, S., "Shirt Capable of Converting Body into Electricity," The Engineer, http://www.theengineer.co.uk/electronics/news/shirt-capable-of-converting-body-heat-into-electricity/1010775.article, dated Nov. 3, 2011, access Mar. 16, 2008.

Futterman, M., "Gait Analysis: The Serious Runner's Salvation," The Wall Street Journal, published Sep. 22, 2014.

Bachman, R., "Gear to Help Runners Diagnose Form and Gait," The Wall Street Journal, published Sep. 22, 2014.

Third Chinese Office Action issued in Chinese Application No. 201510970010.2, dated Apr. 14, 2020, 16 pages.

Zheng Xiuyuan et al. "Modern Sports Biomechanics", pp. 80-83, National Defense Industry Press, Oct. 30, 2002.

* cited by examiner

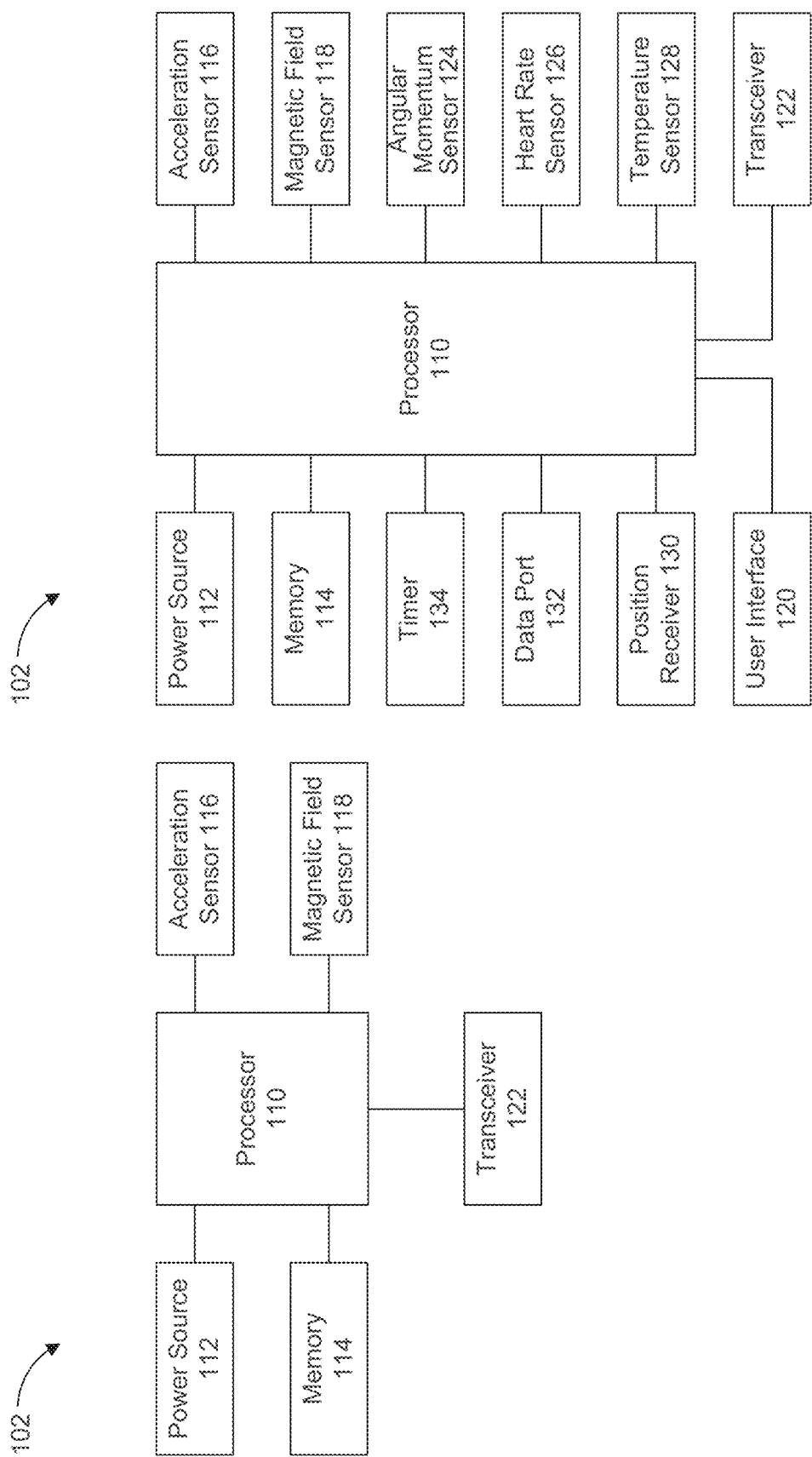

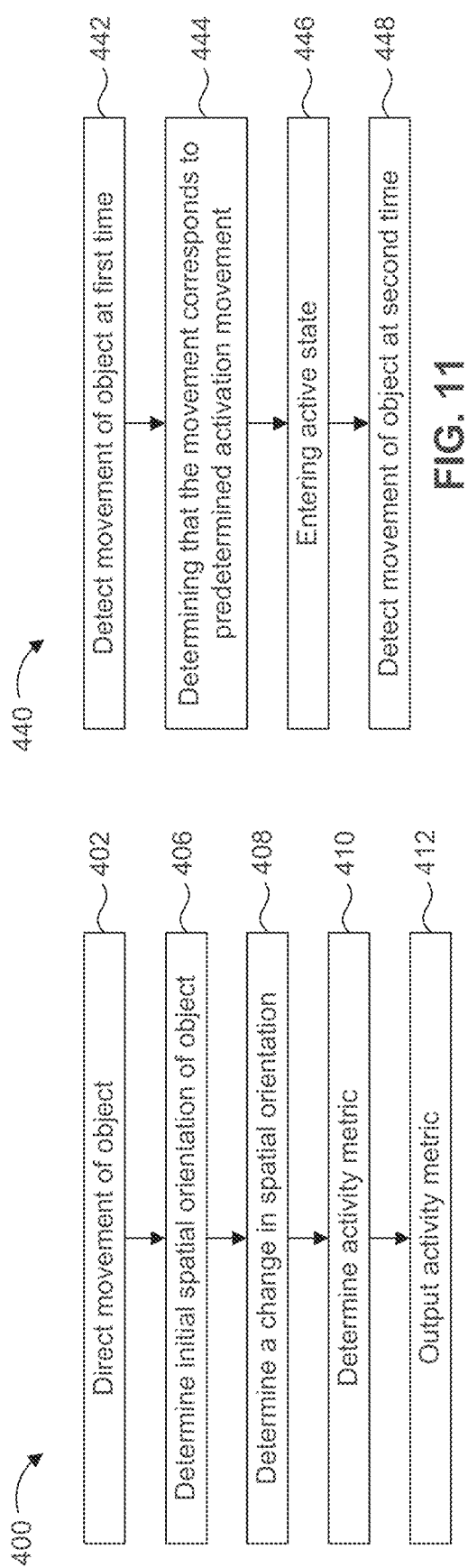
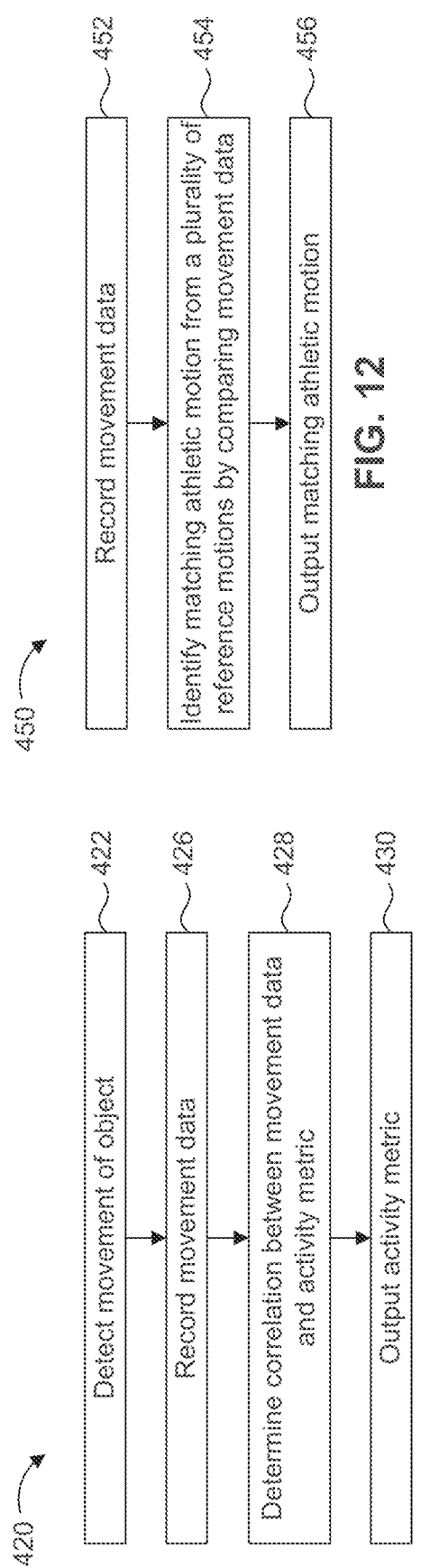

|  | Foot Strike | | |
|---|---|---|---|
| Pronation Angle | Heel Striker (>5°) | Midfoot Striker (-5° to 5°) | Forefoot Striker (<5°) |
| Pronator (1 > 12°) |  | Stable | Neutral / Natural - depends on pronation rate |
| Mild Pronator (5° to 12°) | Stable | Mileage per run : More than 5k Stable<br>Mileage per run : up to 5k distance per run<br>Fast | Running Experience : Everyone else<br>Neutral / Natural - depends on pronation rate<br>Mileage per run : Expert (up to 5k distance per run)<br>Fast |
| Neutral (-5° to 5°) | High Pronation Rate Stable<br>Average Pronation Rate Neutral<br>Low Pronation Rate Neutral | Mileage per run : More than 5k High Pronation Rate Stable<br>Average Pronation Rate Neutral<br>Low Pronation Rate Neutral<br>Mileage per run : up to 5K distance per run<br>Fast | Neutral / Natural - depends on pronation rate<br>Mileage per run : up to 5K distance per run<br>Fast |

FIG. 16C

Name

What kinds of running will these shoes be used for? (you can choose multiple)

For the Love of It | Training for a Race | Stay Healthy | Lose Weight | Training for Sports What kinds of surfaces will these shoes be used on? (you can choose multiple)

Road/Sidewalk | Treadmill | Trail | Everywhere

What's your longest run in terms of time?

30 Minutes or Less | 30 Minutes to an Hour | More than an Hour

○ ● ●

Back

ED
*11:48 am*

Style | Run | Learn | Shoes

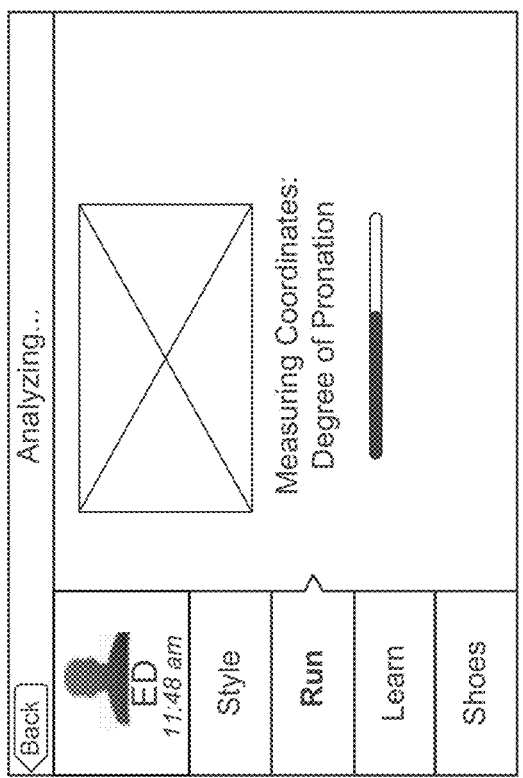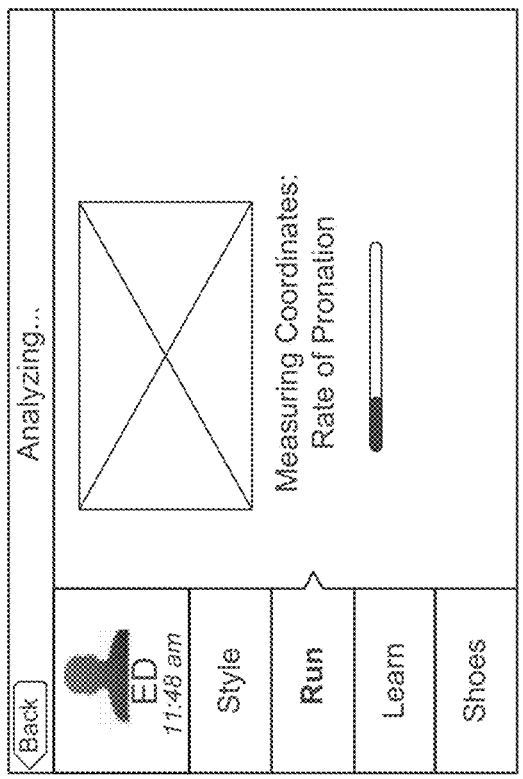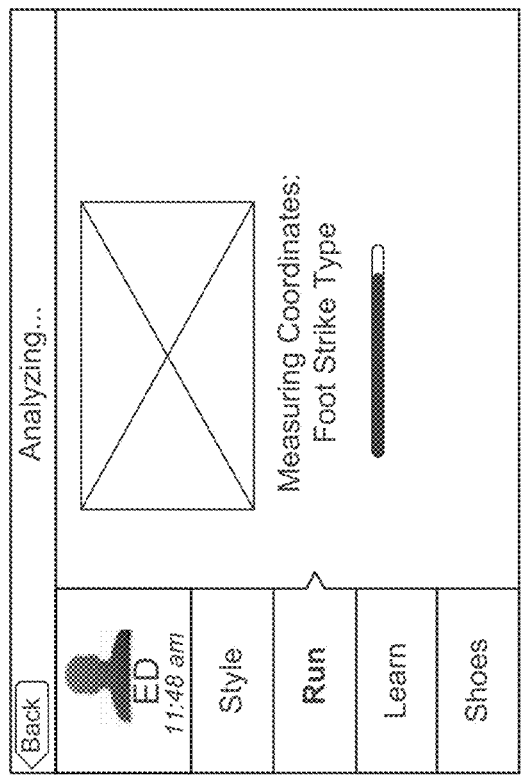
FIG. 21

FIG. 24A

RETAIL STORE MOTION SENSOR SYSTEMS AND METHODS

FIELD OF THE INVENTION

Embodiments of the present invention generally relate to systems and methods for using sensors to provide feedback or recommendations about a piece of athletic equipment or apparel. More particularly, embodiments of the present invention relate to systems and methods for using motion sensors to provide feedback or recommendations about a piece of athletic equipment or apparel in a retail environment.

BACKGROUND OF THE INVENTION

Athletic activity is important to maintaining a healthy lifestyle and is a source of entertainment for many people.

Technology has resulted in the development of fitness monitoring devices that are capable of recording information about an individual's performance during an athletic activity using sensors, and in some cases providing feedback about the individual's performance. Some fitness monitoring devices employ sensors attached to the individual's body, while other fitness monitoring devices rely on sensors attached to a piece of athletic equipment. Such sensors may be capable of measuring various physical and/or physiological parameters associated with the individual's physical activity.

While some existing fitness monitoring devices are capable of making relatively simple performance determinations such as an individual's current heart rate or total step count for an activity, more advanced determinations are often not possible or suffer from accuracy issues. Finally, the performance feedback provided by existing devices to individuals often fails to provide these individuals with quick, accurate, insightful information that would enable them to easily compare past performances, develop strategies for improving future performances, visualize performances, or select new training regimens or athletic equipment, such as articles of footwear in a retail environment.

BRIEF SUMMARY OF THE INVENTION

Embodiments of the present invention relate to a method for providing a recommendation to an individual about an article of footwear, including the steps of receiving data about the individual from a sensor module associated with the individual during a first athletic activity engaged in by the individual, determining a first characteristic about the individual's gait based on the data related to the first athletic activity, providing a recommendation about a first article of footwear to the individual based on the first characteristic, receiving data about the individual from the sensor module associated with the individual during a second athletic activity engaged in by the individual, determining a second characteristic about the individual's gait based on the data related to the second athletic activity, comparing the first characteristic with the second characteristic, and providing a recommendation about a second article of footwear to the individual based on the comparison.

Embodiments of the present invention also relate to a method for providing a recommendation to an individual for an article of footwear in a retail environment, including the steps of creating an account for the individual, obtaining personal information from the individual, receiving motion data related to the individual from a sensor module associated with the individual while the individual is engaged in an athletic activity, determining based on the data a characteristic about a gait of the individual, providing a recommendation about an article of footwear to the individual based on the characteristic and based on the personal information, storing the personal information, the characteristic, and the recommendation in association with the account for the individual.

Embodiments of the present invention further relate to a retail enhancement system, including a sensor module configured to obtain data relating to a physiological parameter of the individual during an athletic activity, and an electronic device separate from the sensor module and configured to associate the sensor module with the individual, wherein the sensor module is configured to be separately associated with a plurality of individuals in the retail environment.

Additional features of embodiments of the invention will be set forth in the description that follows, and in part will be apparent from the description, or may be learned by practice of the invention. Both the foregoing general description and the following detailed description are exemplary and explanatory and are intended to provide further explanation of the invention as claimed.

BRIEF DESCRIPTION OF THE DRAWINGS/FIGURES

The accompanying figures, which are incorporated herein, form part of the specification and illustrate embodiments of the present invention. Together with the description, the figures further serve to explain the principles of and to enable a person skilled in the relevant arts to make and use the invention.

FIG. 1 is an illustration of an individual and a retailer using a retail enhancement system according to an embodiment of the present invention.

FIGS. 2A-B are illustrations of selected articles of footwear utilizing sensor modules of a retail enhancement system according to an embodiment of the present invention.

FIGS. 6A-B are diagrams of sensor modules according to an embodiment of the present invention.

Figure 7A:
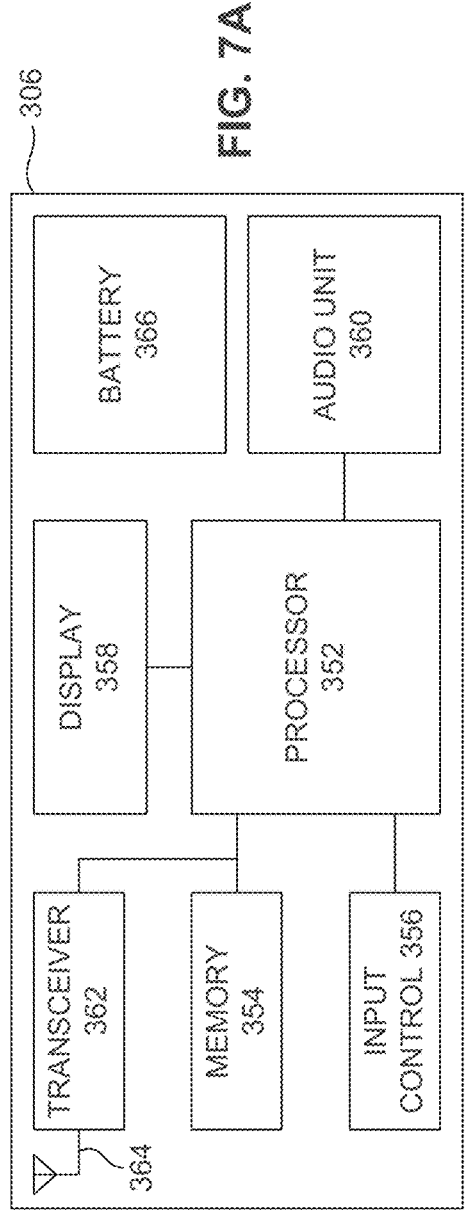
Figure 7B:
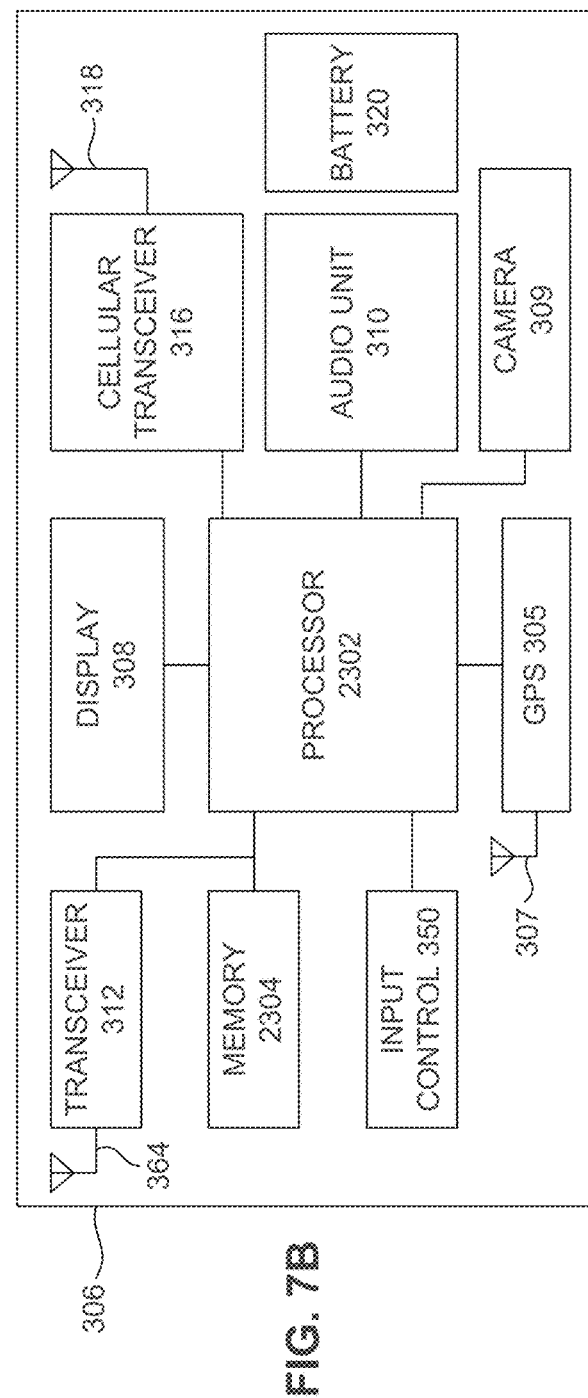

FIGS. 7A-B are diagrams of electronic devices according to an embodiment of the present invention.

Figure 8B:
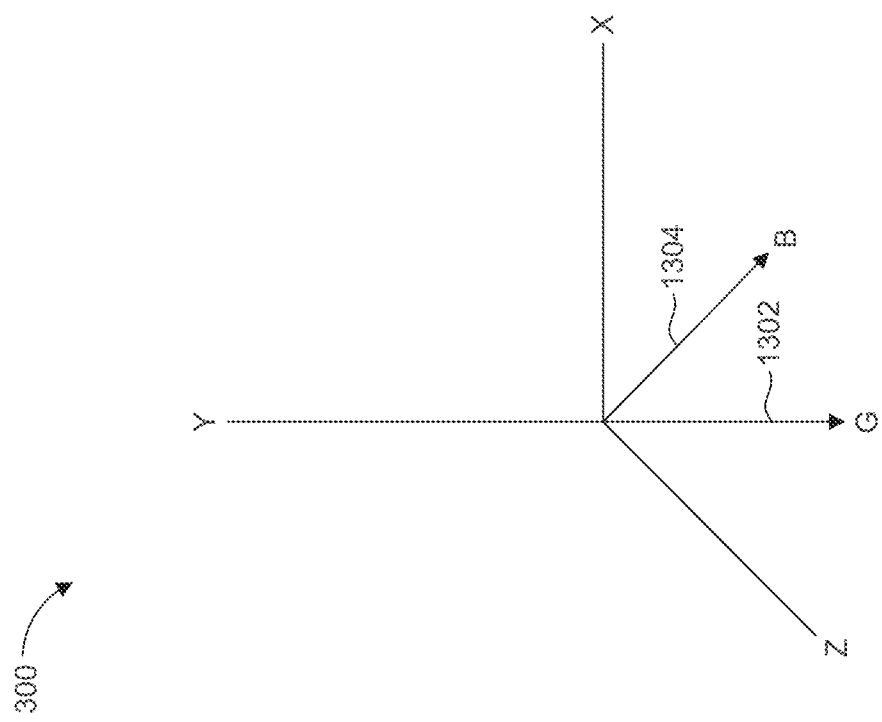
Figure 8A:
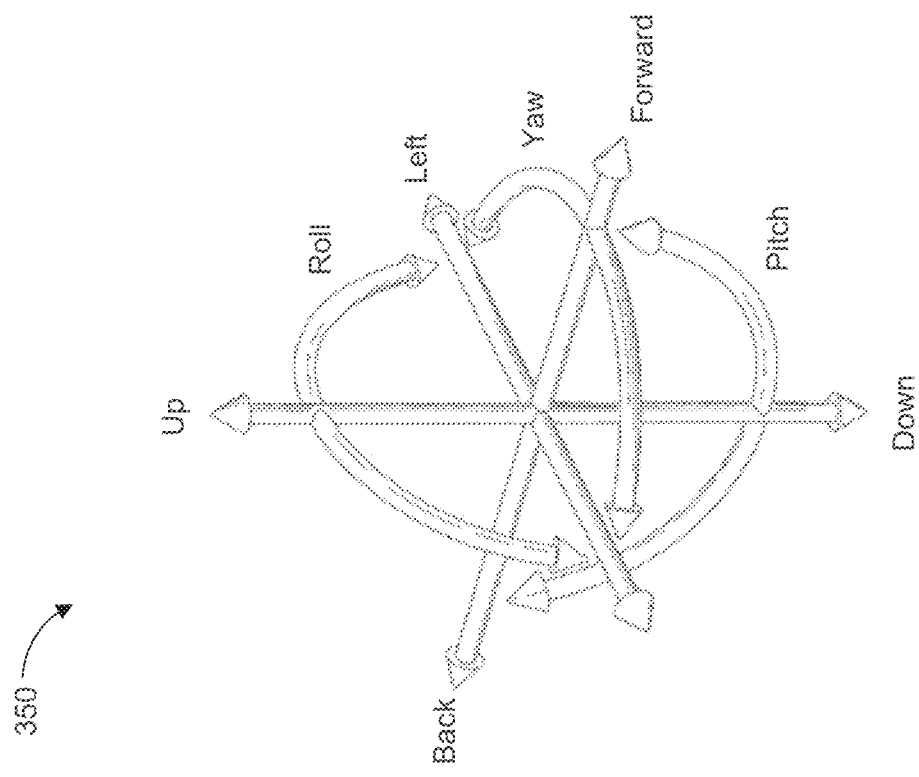

FIGS. 8A-B are diagrams of coordinate systems according to an embodiment of the present invention.

FIG. 9 is a flowchart illustrating a method for determining an activity metric, such as gait characteristic, according to an embodiment of the present invention.

FIG. 10 is a flowchart illustrating a method for determining an activity metric, such as gait characteristic, according to an embodiment of the present invention.

FIG. 11 is a flowchart illustrating a method for activating a sensor module, according to an embodiment of the present invention.

FIG. 12 is a flowchart illustrating a method for identifying a matching athletic motion, such as running, according to an embodiment of the present invention.

Figure 13:
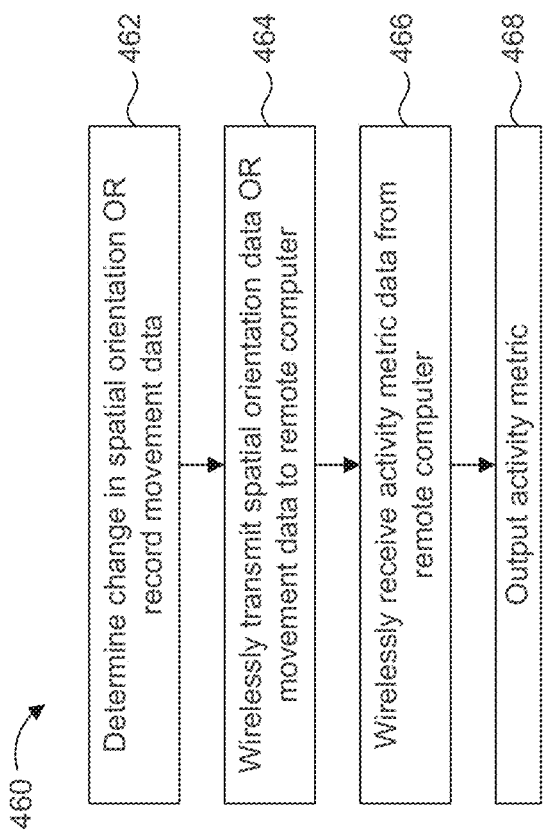
Figure 14:
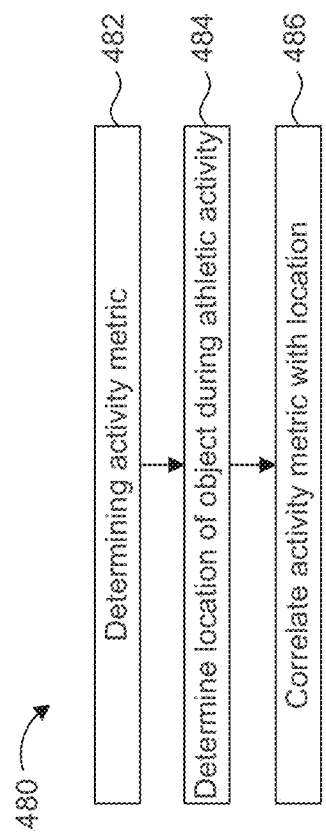

FIG. 13 is a flowchart illustrating a method for communicating with a remote computer according to an embodiment of the present invention FIG. 14 is a flowchart illustrating a method for correlating an activity metric, such as gait characteristic, with a location according to an embodiment of the present invention.

Figure 15:
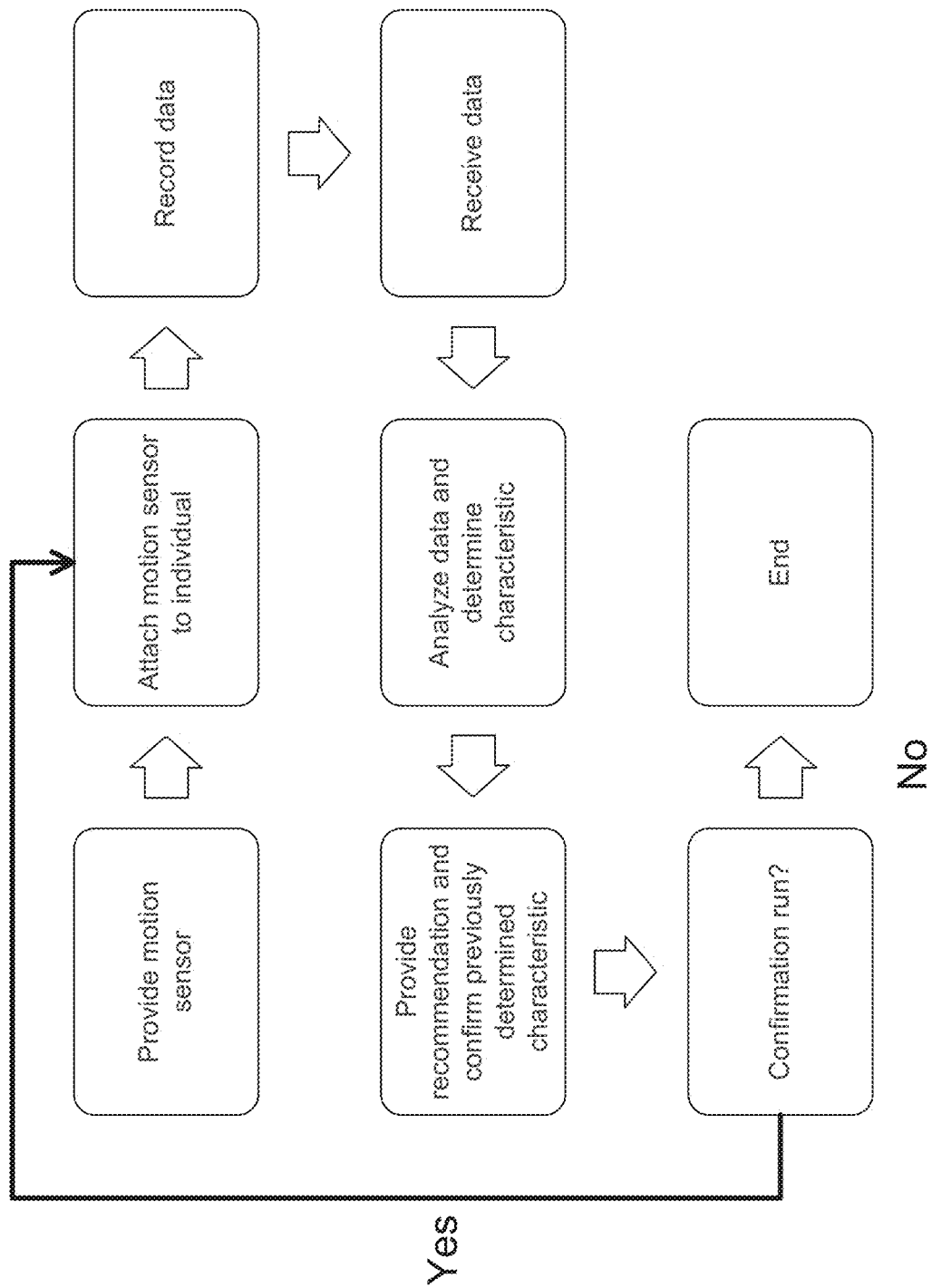

FIG. 15 is a flowchart illustrating a method for feedback of a recommendation of an article of footwear according to an embodiment of the present invention.

Figure 16A:
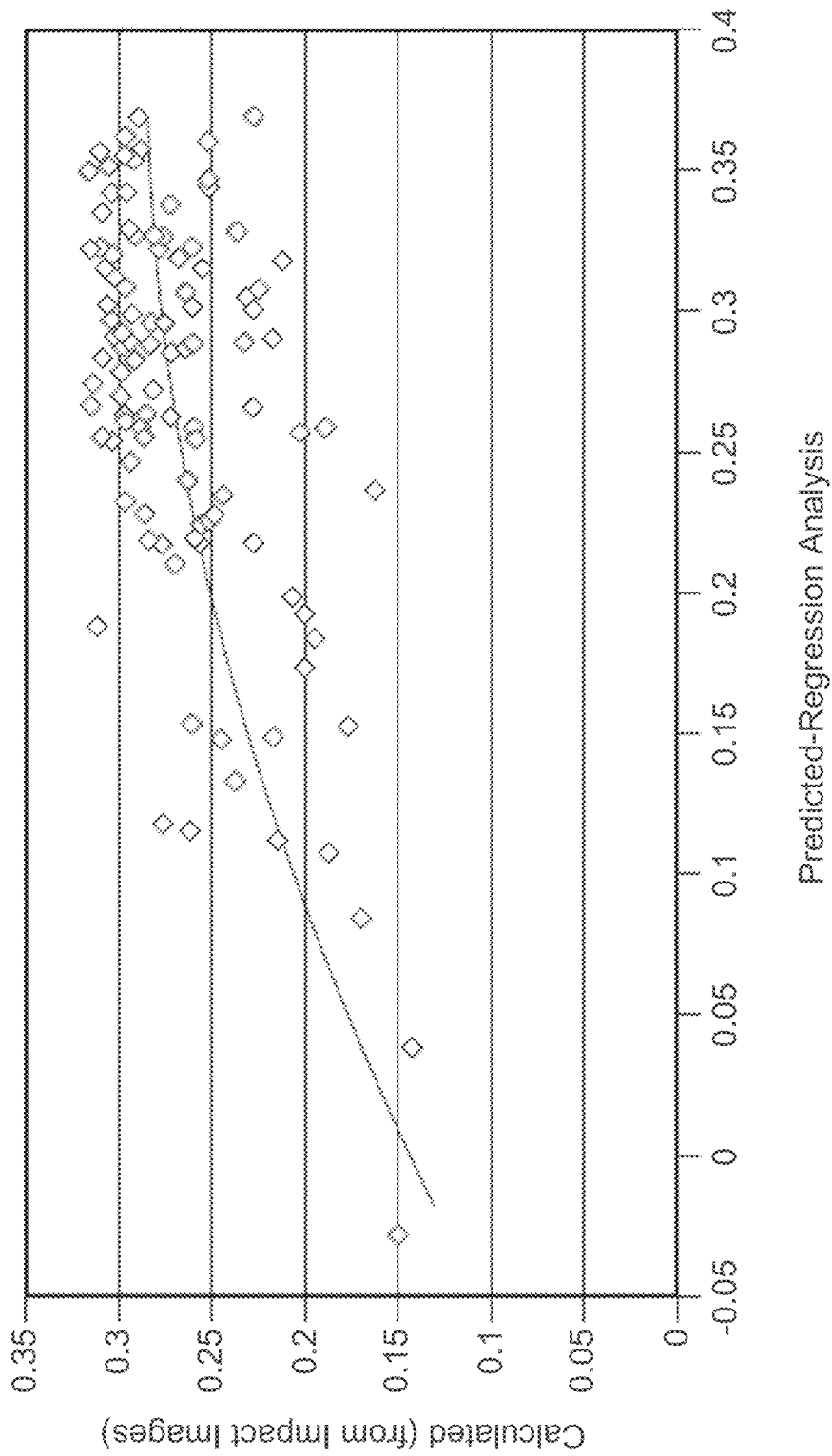

FIG. 16A is an illustration of a regression analysis plot according to an embodiment of the present invention.

Figure 16B:
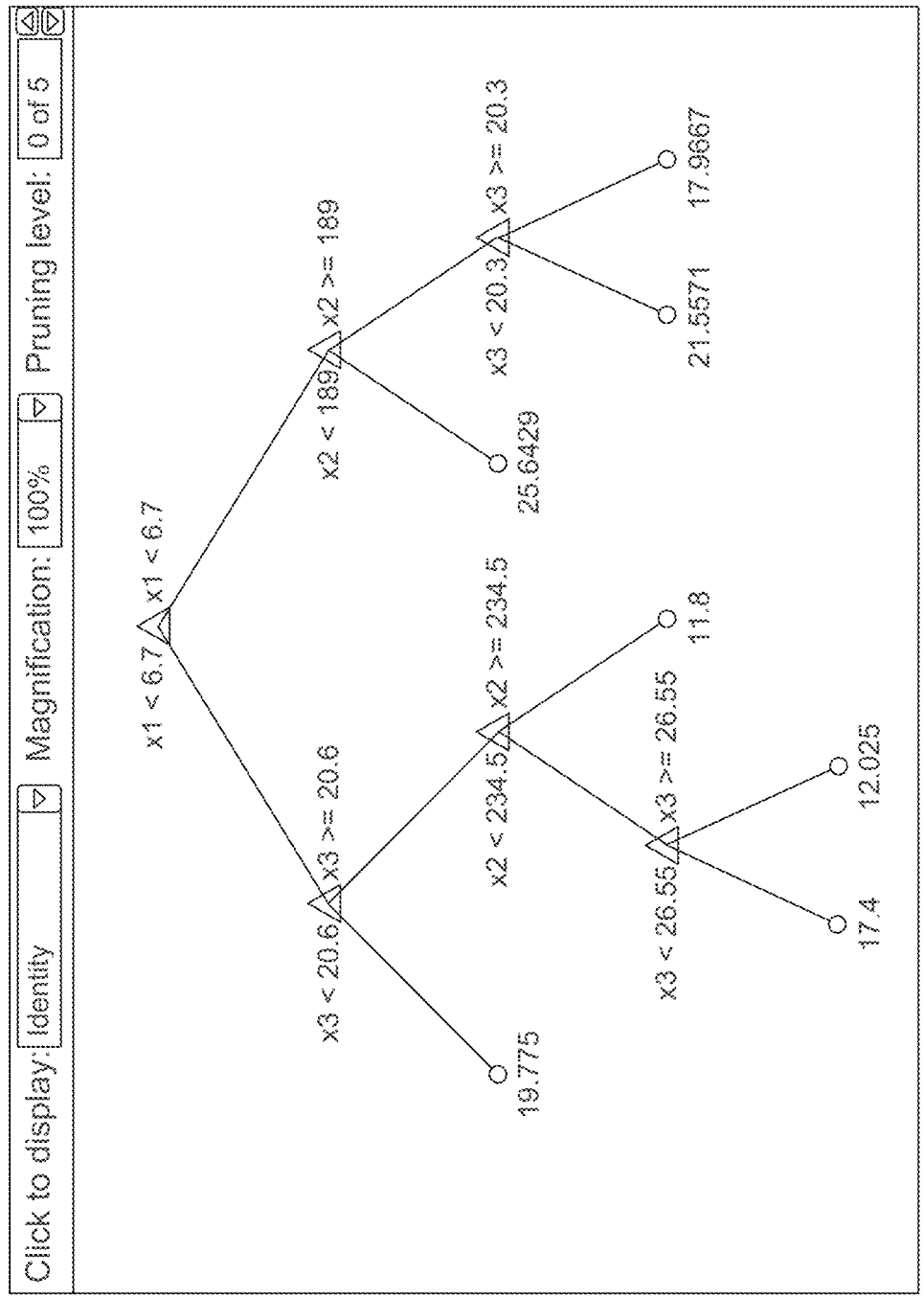

FIG. 16B is an illustration of a regression tree according to an embodiment of the present invention.

FIG. 16C is an illustration of a characteristic table according to an embodiment of the present invention.

Figure 17:
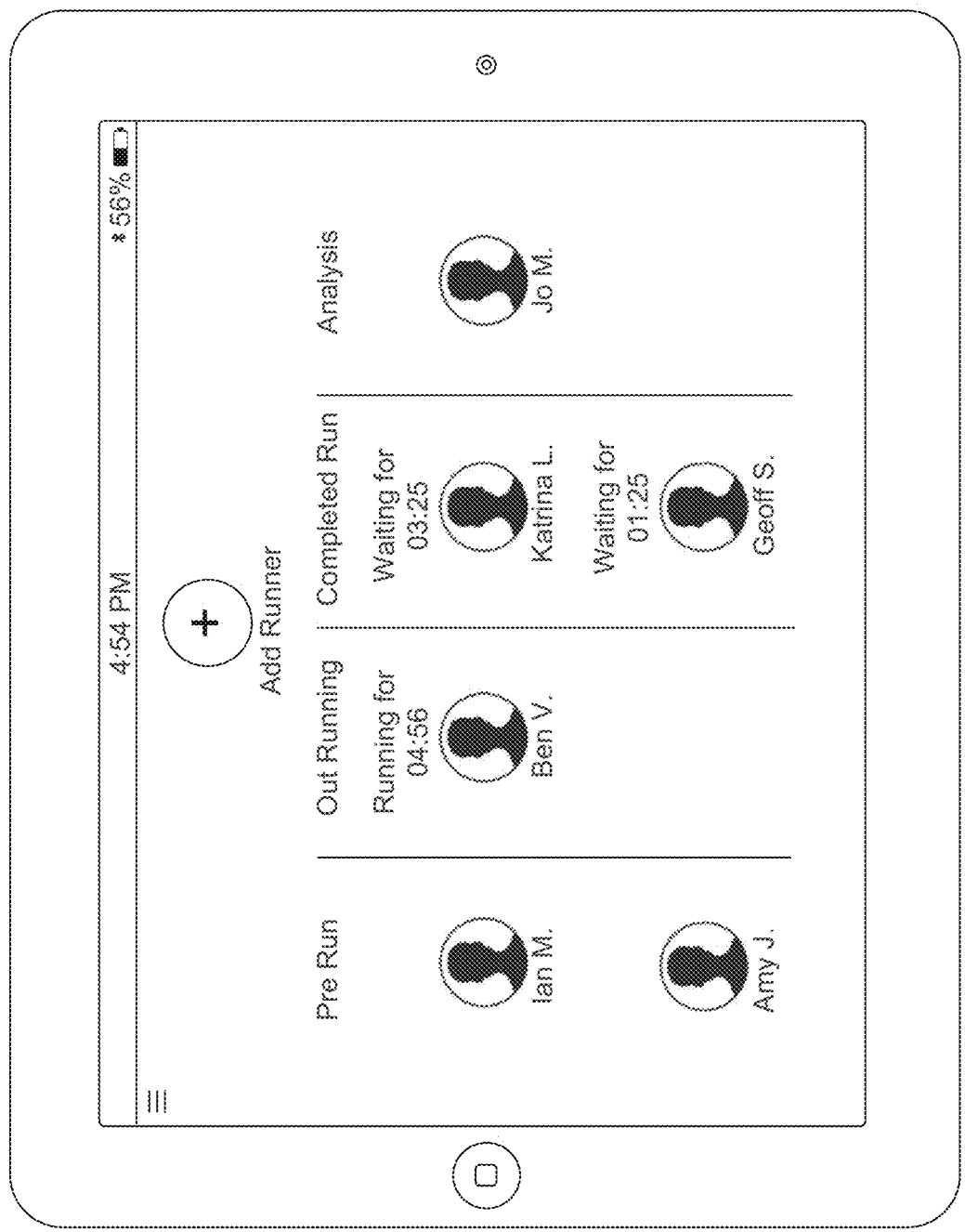

FIG. 17 is a graphical user interface for a retail enhancement system application according to an embodiment of the present invention.

Figure 18:
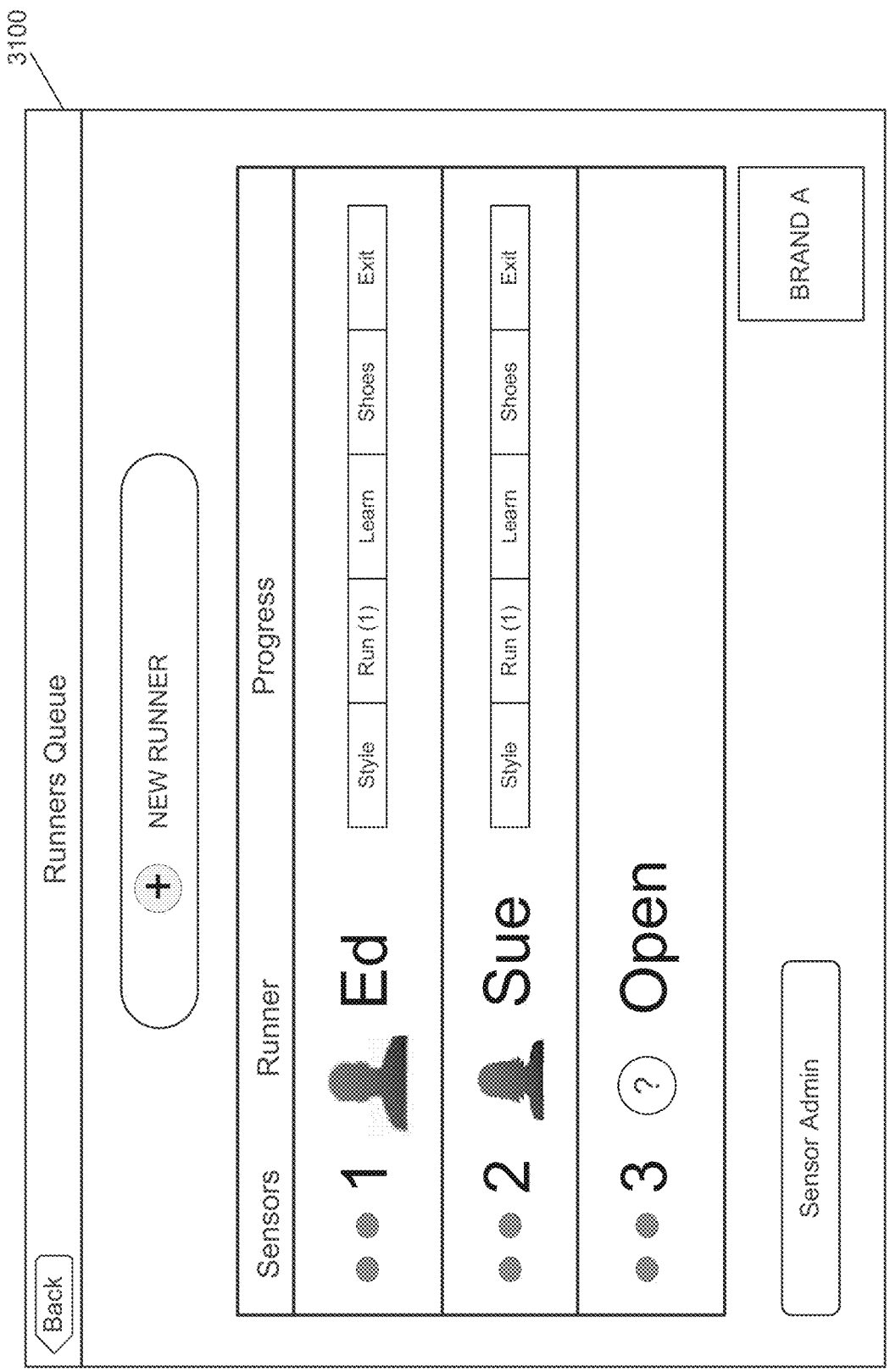

FIG. 18 is a graphical user interface for a retail enhancement system application according to an embodiment of the present invention.

FIG. 19A is a graphical user interface for a retail enhancement system application according to an embodiment of the present invention.

Figure 19B:
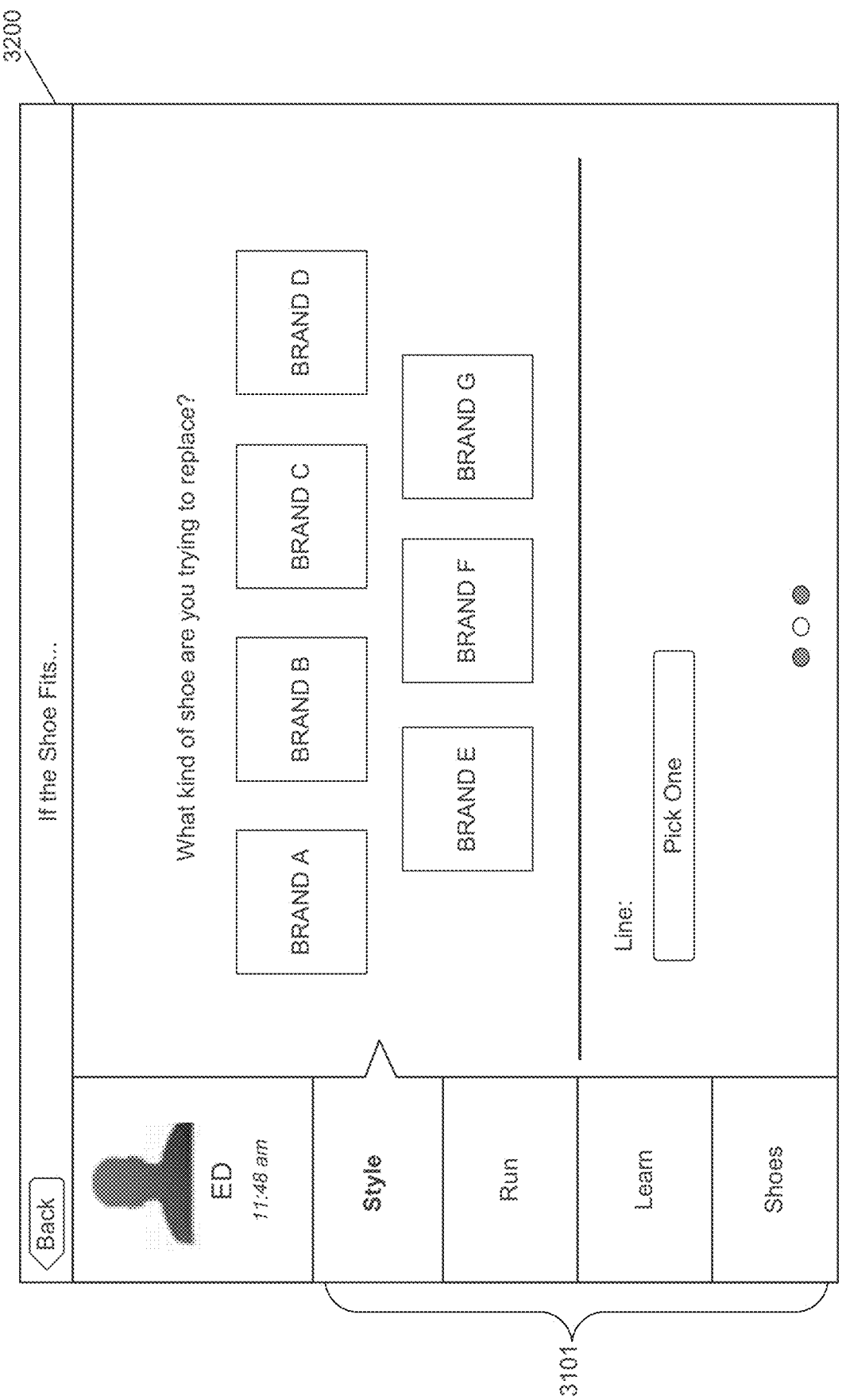

FIG. 19B is a graphical user interface for a retail enhancement system application according to an embodiment of the present invention.

Figure 19C:
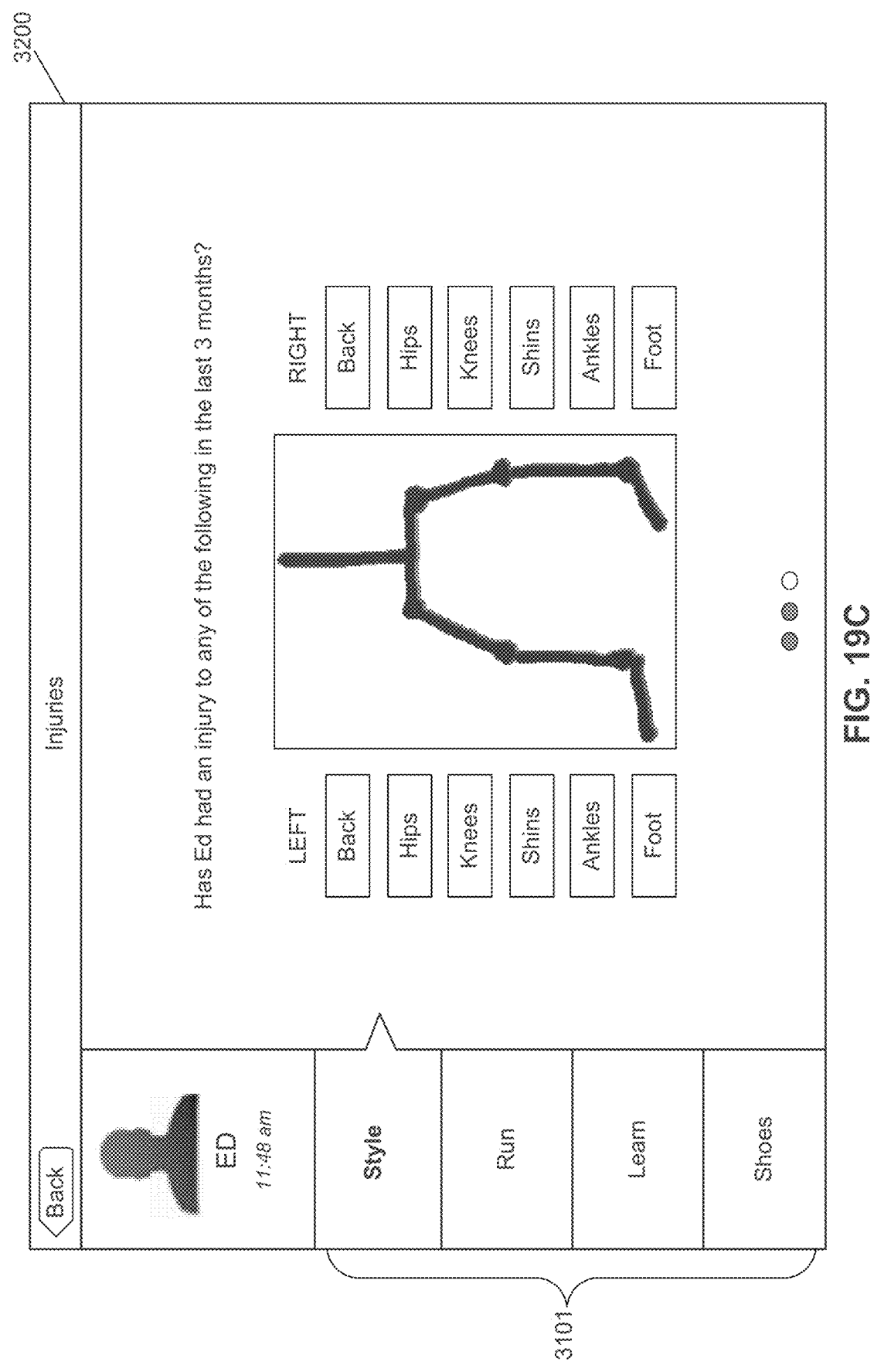

FIG. 19C is a graphical user interface for a retail enhancement system application according to an embodiment of the present invention.

Figure 20A:
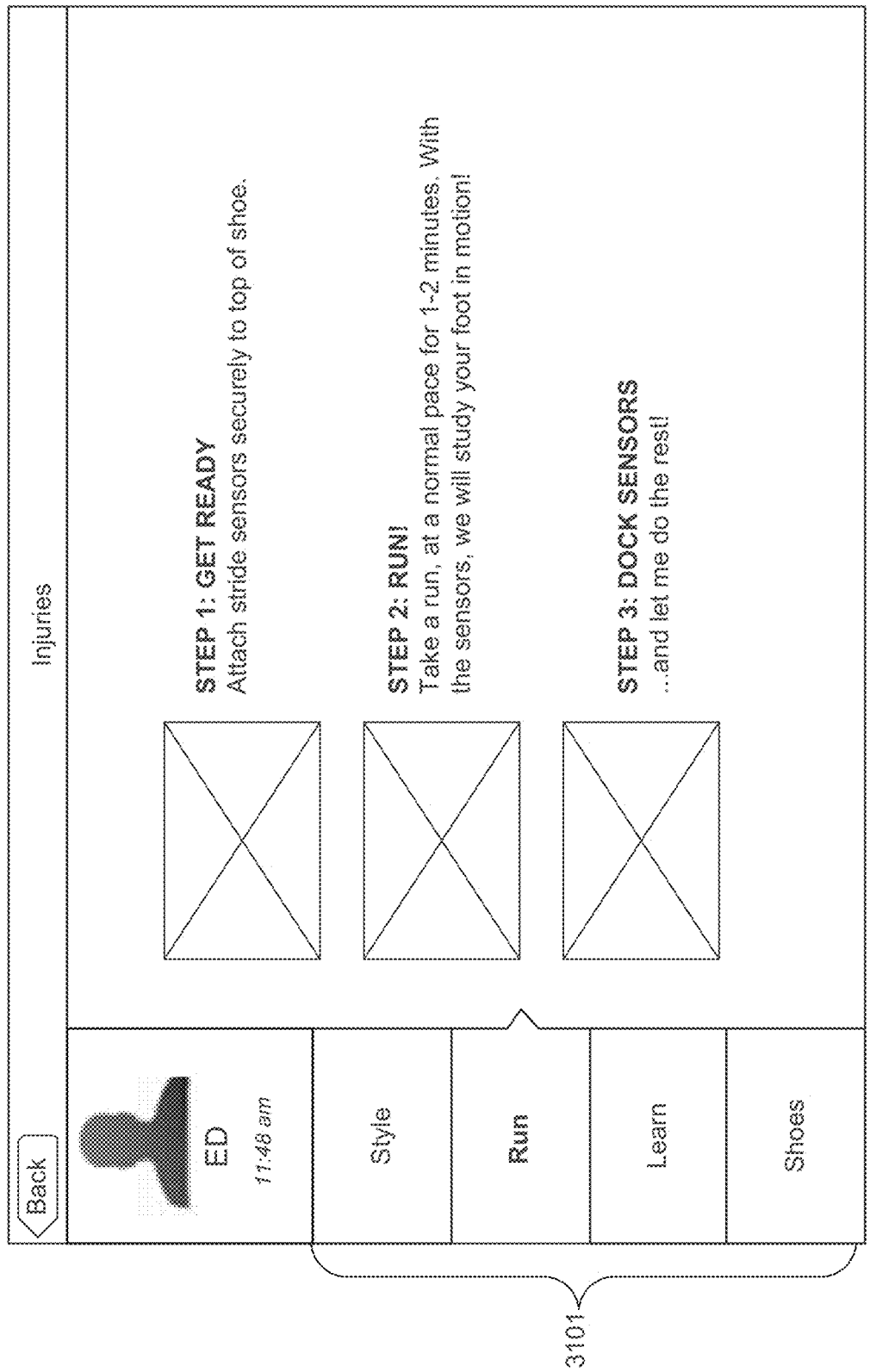

FIG. 20A is a graphical user interface for a retail enhancement system application according to an embodiment of the present invention.

Figure 20B:
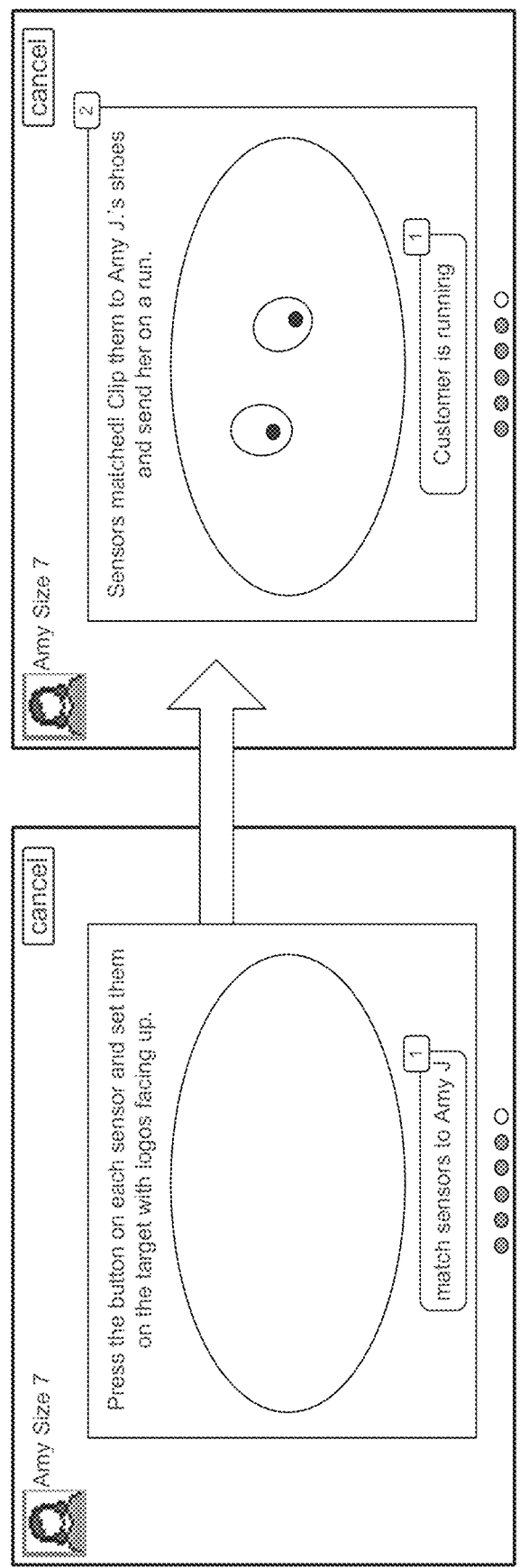

FIG. 20B is a graphical user interface for a retail enhancement system application according to an embodiment of the present invention.

Figure 20C:
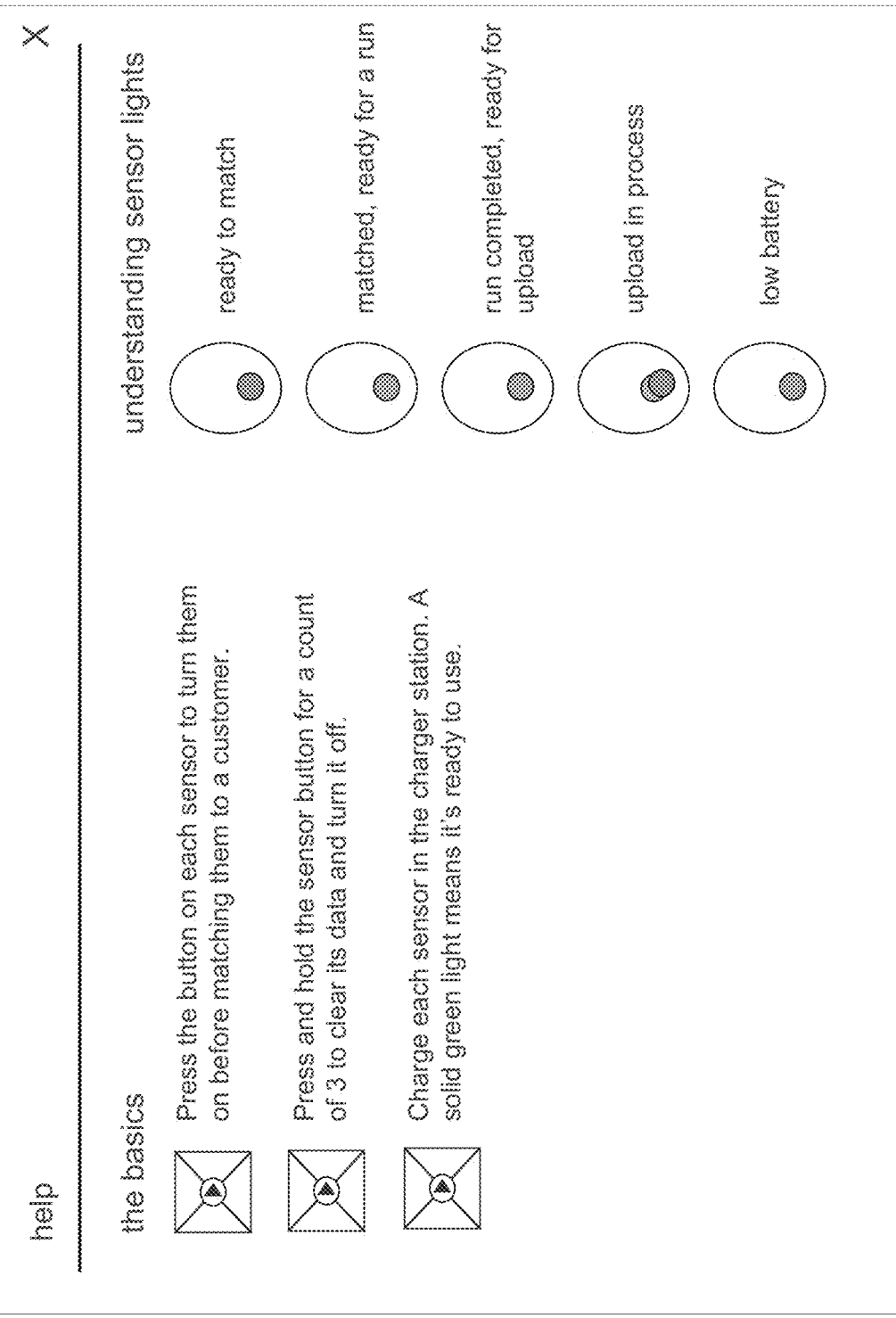

FIG. 20C is a graphical user interface for a retail enhancement system application according to an embodiment of the present invention.

FIG. 21 is a graphical user interface for a retail enhancement system application according to an embodiment of the present invention.

Figure 22A:
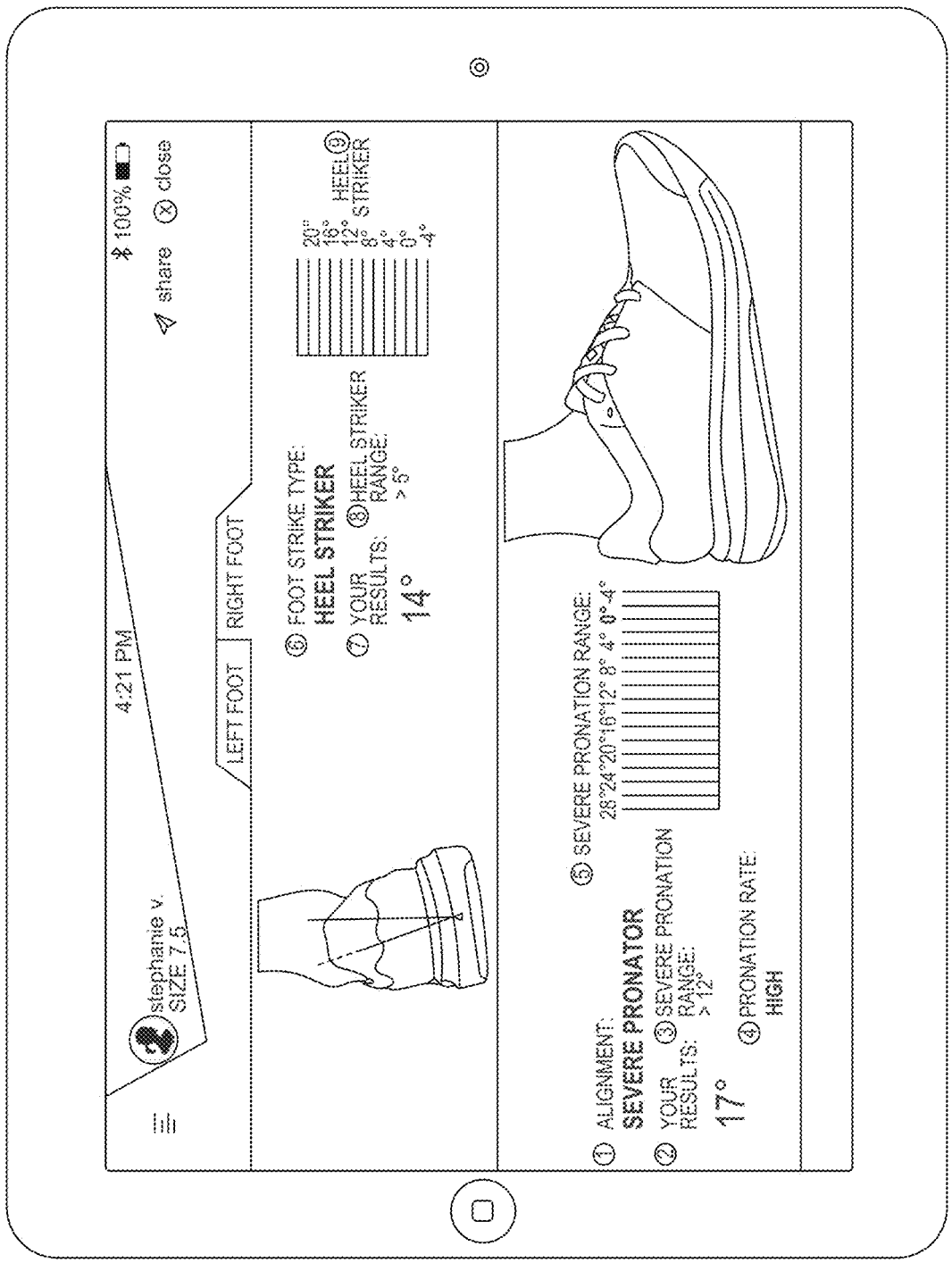

FIG. 22A is a graphical user interface for a retail enhancement system application according to an embodiment of the present invention.

Figure 22B:
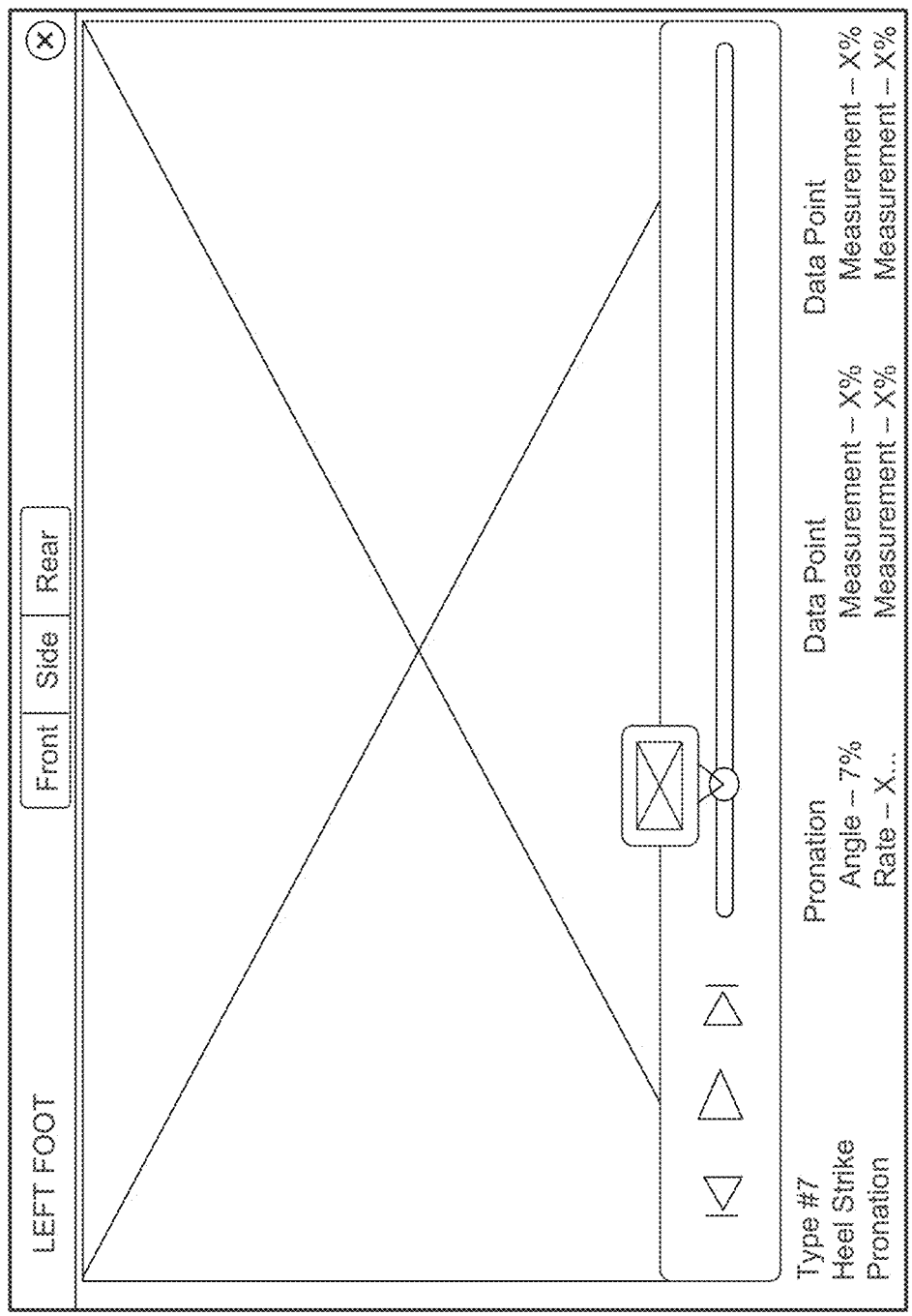

FIG. 22B is a graphical user interface for a retail enhancement system application according to an embodiment of the present invention.

Figure 23A:
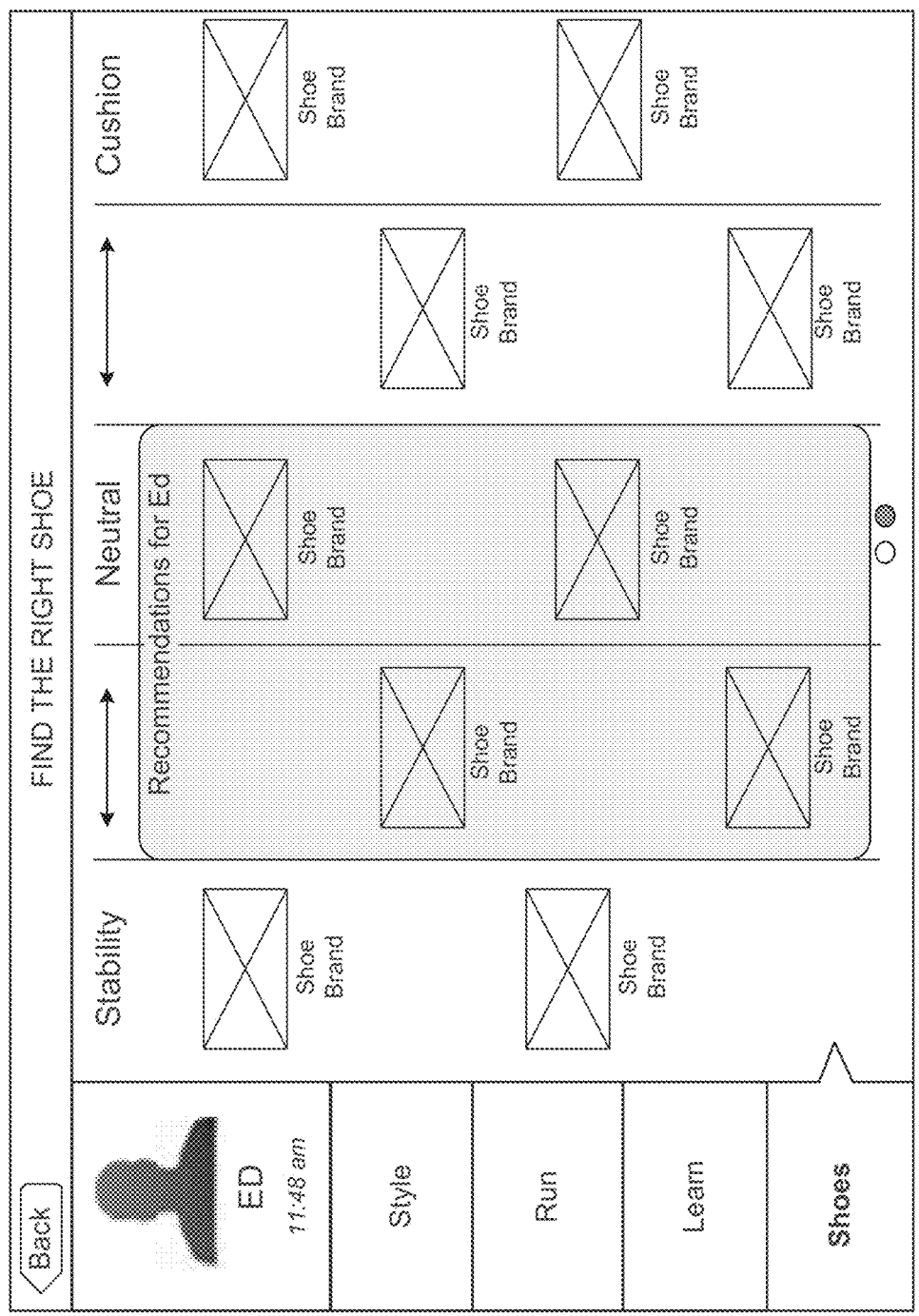

FIG. 23A is a graphical user interface for a retail enhancement system application according to an embodiment of the present invention.

Figure 23B:
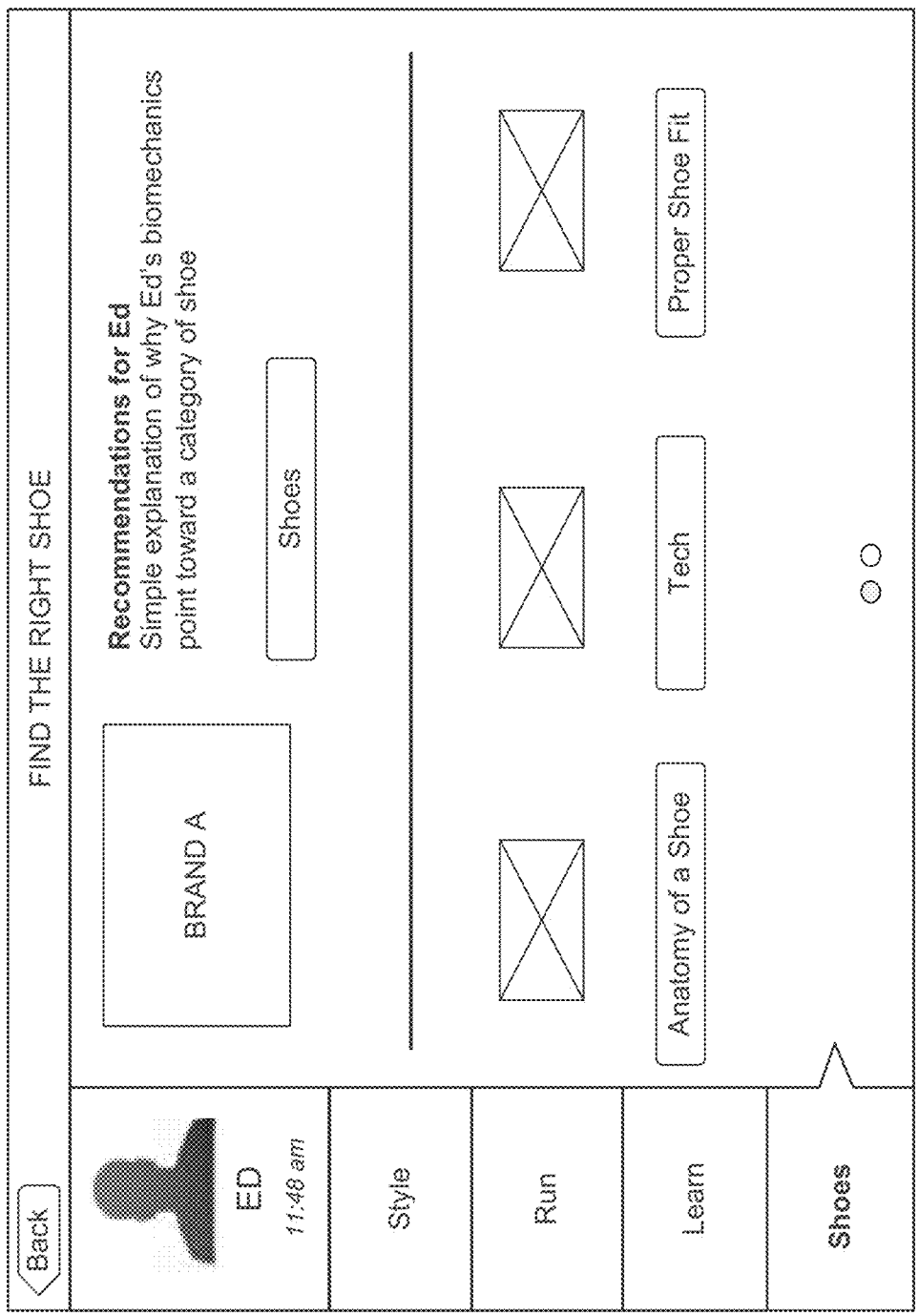

FIG. 23B is a graphical user interface for a retail enhancement system application according to an embodiment of the present invention.

Figure 24A:
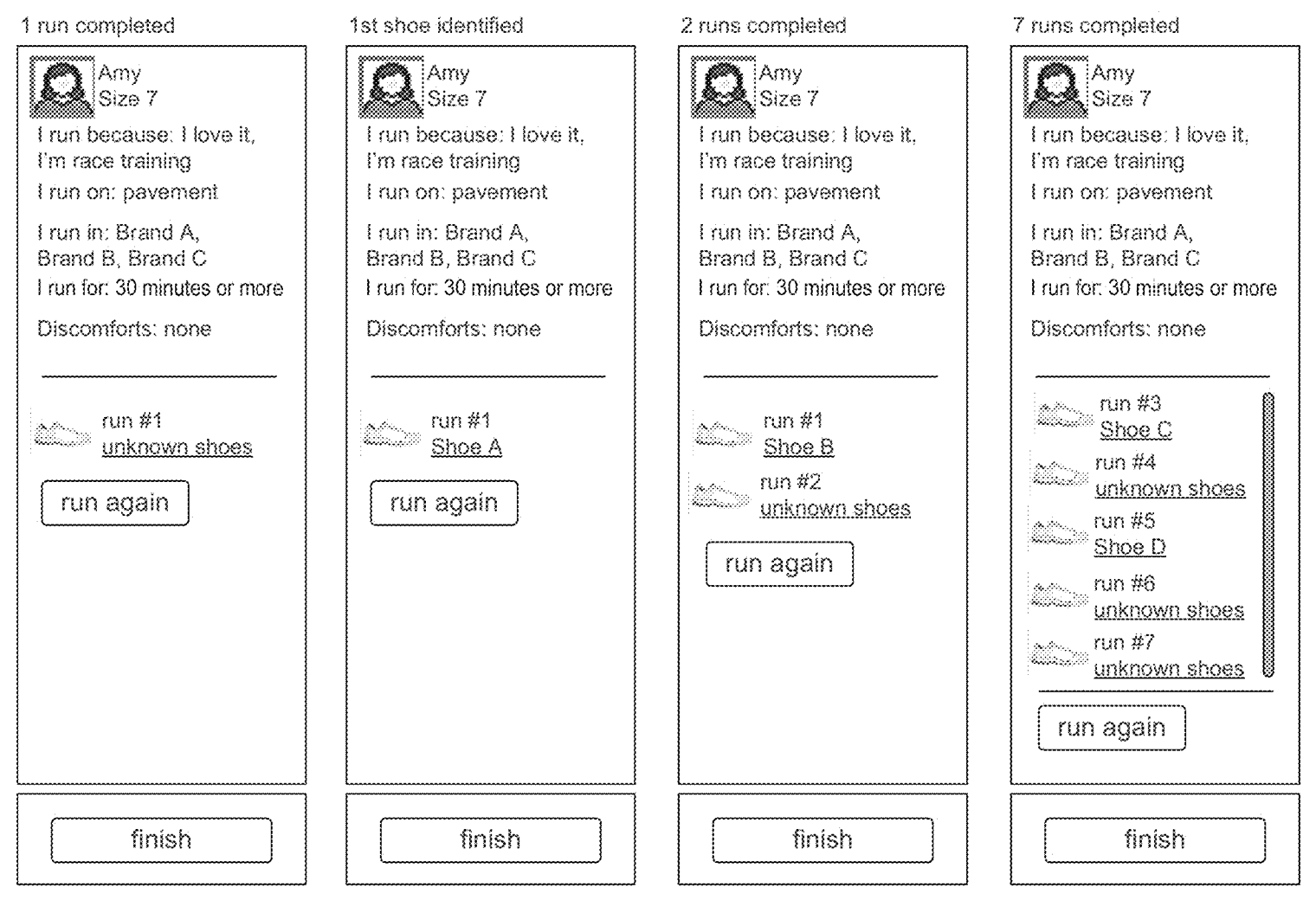

FIG. 24A is a graphical user interface for a retail enhancement system application according to an embodiment of the present invention.

Figure 24B:

FIG. 24B is a graphical user interface for a retail enhancement system application according to an embodiment of the present invention.

Figure 25:
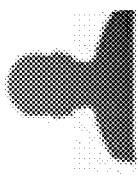

FIG. 25 is a graphical user interface for a retail enhancement system application according to an embodiment of the present invention.

Figure 26:
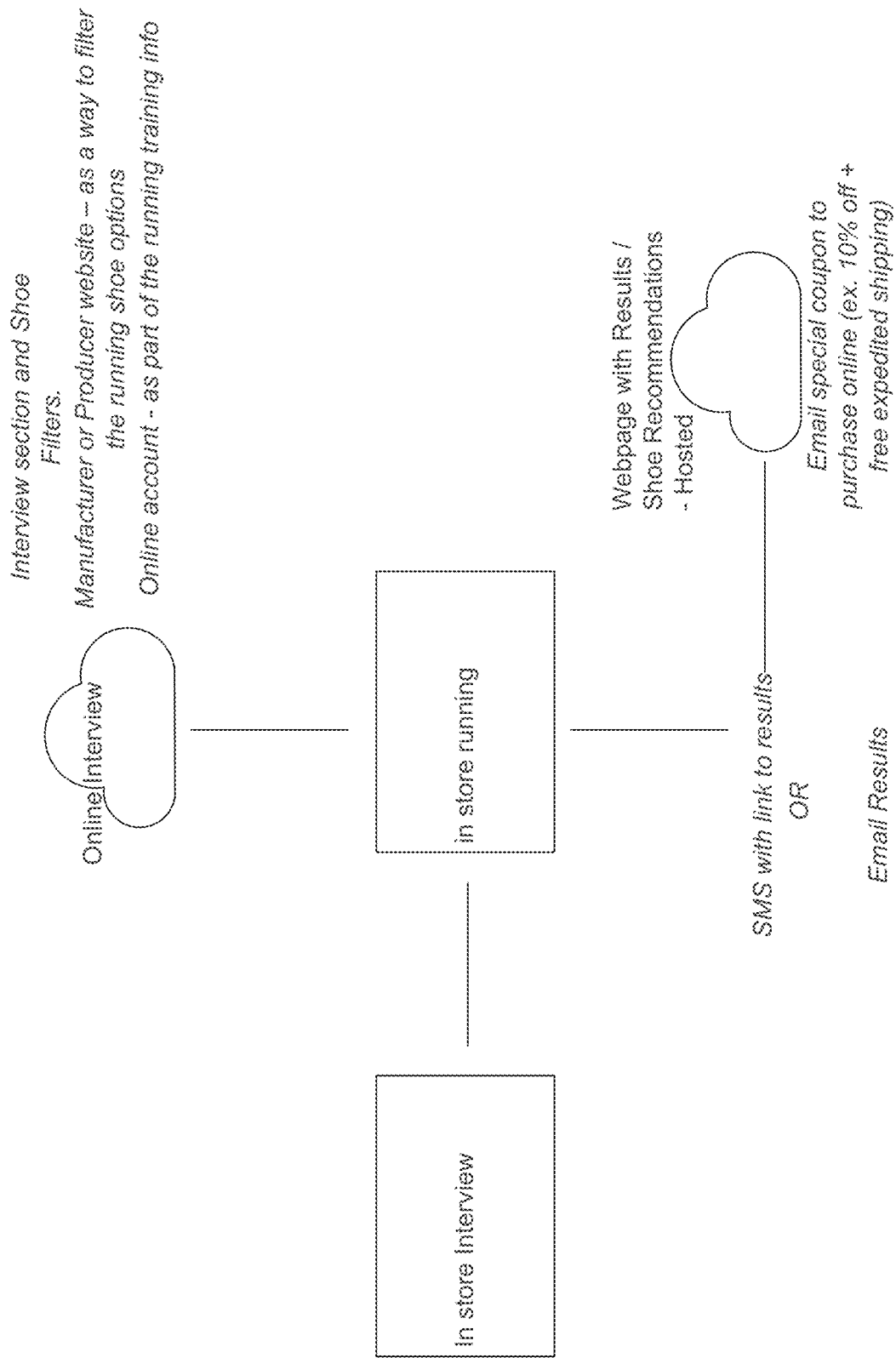

FIG. 26 is a conceptual diagram of a retail enhancement system according to an embodiment of the present invention.

DETAILED DESCRIPTION OF THE INVENTION

The present invention will now be described in detail with reference to embodiments thereof as illustrated in the accompanying drawings. References to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "invention" or "present invention" as used herein is a non-limiting term and is not intended to refer to any single embodiment of the particular invention but encompasses all possible embodiments as described in the application.

Various aspects of the present invention, or any parts or functions thereof, may be implemented using hardware, software, firmware, non-transitory tangible computer readable or computer usable storage media having instructions stored thereon, or a combination thereof, and may be implemented in one or more computer systems or other processing systems.

In general, in some embodiments, a method is provided for providing a recommendation to an individual about an article of footwear. The method may include receiving data about the individual from a sensor module associated with the individual during a first athletic activity engaged in by the individual. After this, the method may include determining a first characteristic about the individual's gait based on the data related to the first athletic activity. Once the first characteristic is determined, the method may provide a recommendation about a first article of footwear to the individual based on the first characteristic. The method may also include receiving data about the individual from the sensor module associated with the individual during a second athletic activity engaged in by the individual, and determining a second characteristic about the individual's gait based on the data related to the second athletic activity. The method may also include comparing the first characteristic with the second characteristic; and providing a recommendation about a second article of footwear to the individual based on the comparison. The method may be carried out in a retail environment.

In some embodiments, the first and second characteristics may include physiological characteristics (e.g. gait characteristics). In some embodiments, the method may determine whether the second characteristic represents an improvement over the first characteristic. In some embodiments, the characteristics may include gait characteristics such as foot strike type (e.g. heel, midfoot, forefoot, etc.), rate of pronation or supination, and degree of pronation and supination.

In some embodiments, the method may include identifying whether a performance goal has been met. In some embodiments, the method may include receiving personal information about the individual prior to receiving the data about the individual. The personal information may include information such as their name, prior injury information, height, weight, gender, shoe size, an athletic goal, intended athletic environment or terrain, intended athletic activity duration, intended athletic activity frequency, intended athletic activity distance, quantitative or qualitative preferences about athletic equipment or footwear (such as level of cushion, preference of weight, materials and the like), and current athletic footwear. In some embodiments, one of the recommendation about the first article of footwear and the recommendation about the second article of footwear may be further based on the personal information In some embodiments, the recommendation may be a recommendation to purchase an article of footwear, and may include one of a style of footwear and a size of footwear.

In other embodiments, the method may include creating an account for the individual. This account may include obtaining personal information from the individual. The method may include receiving motion data related to the individual from a sensor module associated with the individual while the individual is engaged in an athletic activity; determining based on the data a characteristic about a gait of the individual; providing a recommendation about an article of footwear to the individual based on the characteristic and based on the personal information. In some embodiments, the method may include storing the personal information, the characteristic, and the recommendation in association with the account for the individual.

The method may include in some embodiments that prior to providing the recommendation about an article of footwear to the individual, determining particular types of footwear that are in stock at the retail environment for purchase, and eliminating potential recommendations for types of footwear that are not in stock at the retail environment for purchase. In some embodiments, the retail environment may be a physical or virtual location. In some embodiments, the method of claim may include that access to the account of the individual is available at a later point in time. In some embodiments, the account is synced for providing access the account at multiple retail environments.

In some embodiments, the method may include receiving motion data via local wired or wireless connection, or via a wide area network. In some embodiments, the method may include identifying which shoes are in stock in other retail environments.

In some embodiments, the method may include recommending a first article of footwear if the first article of footwear is in stock at the retail environment; recommending a second article of footwear if the first article of footwear is not in stock at the retail environment. In other embodiments, the method may include recommending other accessories/apparel/equipment to go with the recommended footwear.

In some embodiments, the method may include monitoring the motion in real-time during the athletic activity.

In some embodiments, the method may include providing data or feedback from the retailer to a manufacturer of articles of footwear.

In some embodiments, a retail enhancement system is provided. In some embodiments, the retail enhancement system may include a sensor module configured to obtain data relating to a physiological parameter of the individual during an athletic activity; and an electronic device separate from the sensor module and configured to associate the sensor module with the individual, wherein the sensor module is configured to be separately associated with a plurality of discrete individuals in the retail environment. This system may be utilized with the above method.

In some embodiments, the electronic device is configured to prompt a retailer to enter information about the individuals related to athletic activity. In other embodiments, the electronic device is configured to prompt the retailer to pair the sensor module to the mobile display, and subsequently attach the sensor module to the shoe of the individual. In other embodiments, the electronic device may be configured to prompt the retailer to attach the sensor module to the shoe of the individual, and subsequently pair the sensor module to the mobile display. The electronic device is configured to receive data from the paired sensor module after the individual engages in an athletic activity in some embodiments. Associating the sensor module may include wirelessly connecting the sensor module with the electronic device. The system may include a first sensor module, and a second sensor module.

The first sensor module may be configured to be removably attached to a first article of footwear to be worn by the individual during the athletic activity and the second sensor module is configured to be removably attached to a second article of footwear to be worn by the individual during the athletic activity. The individual may be a first individual and the athletic activity is a first athletic activity, wherein the first sensor module is configured to be removably attached to an article of footwear to be worn by the first individual during the first athletic activity, and wherein the second sensor module is configured to be removably attached to an article of footwear to be worn by a second individual during a second athletic activity. The system may perform a sales transaction at the electronic device including the article of footwear.

The methods and systems discussed above are further described below. The figures below apply to both the method and system embodiments of the invention.

In some embodiments, a sensor module is placed and/or built into an article of footwear to measure, for example, a runner's running form and gait cycle (e.g., sensor is placed on, removably attached to, or built into the heel, midsole, or toe of the article of footwear). Additional sensors/motion monitors can also be placed on the runner's knee and hip, for example, to obtain more information about the runner's running form. The information collected by the sensors/motion monitors is analyzed and characterized with a retail enhancement system and method for providing a recommendation to an individual about an article of footwear of the present invention and used to provide feedback to the runner regarding how the runner can improve his or her running form and/or gait cycle.

Figure 1:
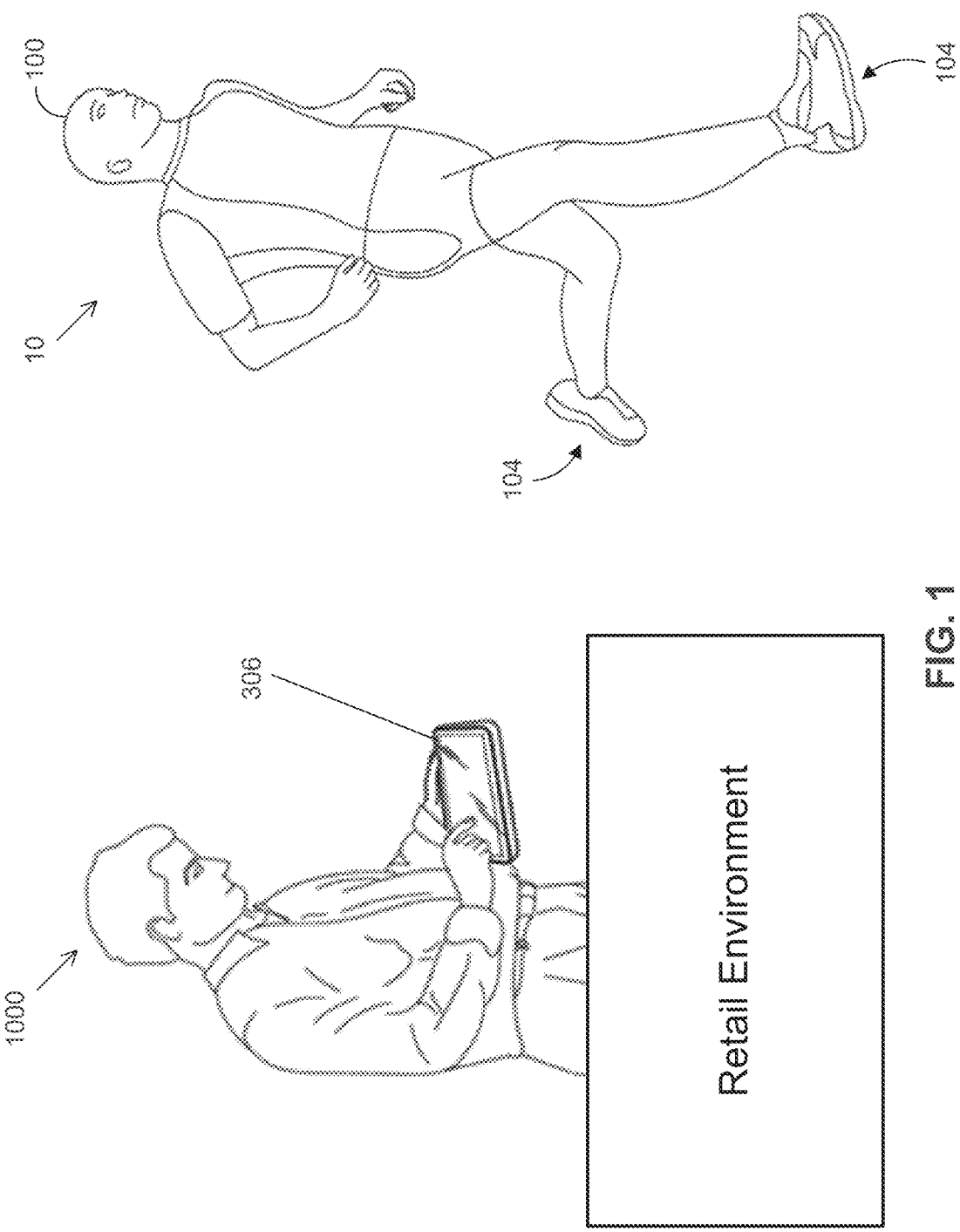

FIG. 1 is an illustration of an individual 100 using a retail enhancement system 10 according to some embodiments of the present invention. The individual 100 may desire to obtain information about the motion of the individual's 100 body or the motion of a piece of the individual's 100 athletic equipment during the course of the athletic activity using retail enhancement system 10 according to the present invention. FIG. 1 also illustrates a method of providing a recommendation to an individual regarding an article of footwear. Interface aspects of the interactive retail system or retail enhancement system software could be, for example, presented to an individual 100 via a screen on the individual's 100 electronic device 306. By using a retail enhancement system 10 including one or more sensor modules 102, embodiments of the present invention described below may advantageously enable an individual (or a retailer 1000) to obtain this or other information about the motion of the individual's body or the motion of a piece of the individual's athletic equipment during the course of the athletic activity. Sensor modules 102 may comprise one or more sensors, such as motion sensors.

The retail enhancement system 10 and methods described above may be carried out at a physical retail environment, such as a sporting goods store, running store, department store and the like. The retailer 1000 may be an employee or clerk of the store in some embodiments. In other embodiments, the retailer 1000 may be a representative of a particular producer or manufacturer of athletic equipment. In some embodiments, the athletic equipment may include articles of footwear. In some embodiments, the retail environment may be a physical location, such as a store. In other embodiments, the retail environment may be a virtual location, where the individual 100 carries out the methods and systems of the present invention at another remote location, not at a store, such as an area around their home.

In some embodiments, the retailer 1000 may use the electronic device 306 to carry out the methods and systems of the present invention. In other embodiments, the individual 100 may use the electronic device 306 to carry out the methods and systems of the present invention. In some embodiments, a combination of both the retailer 1000 and individual 100 may use the electronic device 306 to carry out the methods and systems of the present invention.

In some embodiments, the electronic device 306 may be for example one of a tablet computer, a mobile phone, a desktop computer, a dedicated retail system general to a retail environment, a retail kiosk specific to particular athletic equipment brands, and the like.

In some embodiments, a producer, manufacturer, or retailer of athletic equipment (such as articles of footwear) may perform testing in advance of their products with the sensor modules 102 and retail enhancement system 10 with many individuals 100 prior to using the system in a retail environment. In this embodiment, the data gathered may aid in recommendations regarding articles of footwear to individuals (e.g. to the individuals as customers). In this embodiment, this may provide a baseline of data for which to compare to the eventual individual 100 (e.g. customer) using the systems and methods in a retail environment.

In an embodiment, electronic device 306 corresponds to a device such as, for example, at tablet computer, retail register kiosk, desktop computer, a PDA device, MP3 player, an electronic watch having a sports operating mode, a workstation, mobile device (e.g., a mobile phone, personal digital assistant, tablet computer, or laptop), computer, server, compute cluster, server farm, game console, set-top box, kiosk, embedded system, a gym machine, a retail system or retail enhancement system or other device having at least one processor and memory. In some embodiments, the individual 100 may have access to the electronic device 306 and at least one sensor module 102 in a location remote from the retail environment. In some embodiments, the individual 100 may then purchase items recommended from an online or virtual retail environment based on the feedback (i.e. they never have to go into the "brick and mortar" retail environment such as a store).

Retail enhancement system 10 according to embodiments of the present invention may be suitable for use by individuals 100 for individual athletic activities and for individuals 100 in a retail environment. For example, retail enhancement system 10 according to embodiments of the present invention may be suitable for use by individuals 100 engaged in athletic activities such running or walking, or retail scenarios related to such.

For example, in embodiments where the monitored object 104 is an article of footwear, certain determinations may be used by the retail enhancement system 10 to help the individual 100 improve their running form or gait characteristics in future athletic activities. Methods used to achieve improvements may be, for example, recommending a particular article of footwear or other piece of athletic equipment or apparel, providing cross-training workouts or drills to the individual 100, providing gait type specific workouts or drills to the individual 100, or prescribing a number of other training regimens.

In some embodiments of the present invention, the retail enhancement system 10 may also include or interact with retail enhancement system software. Interface aspects of the interactive retail system or retail enhancement system software could be, for example, presented to an individual 100 via a screen on the individual's 100 electronic device 306. The interactive retail system or retail enhancement system 10 could provide a platform for selecting and/or ordering products offered by the provider of the system. Based on the characteristic or specific athletic movement provided by the monitoring/retail enhancement system 10, and/or based on any training or coaching provided, as described above, the interactive retail system or retail enhancement system 10 could suggest specific products or product lines that may be helpful to the individual 100 in improving their future performance. In some embodiments, personal data about the individual stored by the monitoring/retail enhancement system 10 may also be used in making the determination of suitable products or product lines.

For example, a soccer player trying to improve her shots may receive a recommendation for a new pair of soccer cleats, while a basketball player trying to improve his jumping ability may receive a recommendation for a new pair of basketball shoes. These recommendations may ultimately be based on data derived from monitoring the individuals 100 body, and/or from monitoring the individual's 100 athletic equipment. For example, a source of inadequate performance may be the individual's 100 performance or it may be that the individual's 100 current equipment has worn out. In some embodiments, the individual 100 may be provided with the option to purchase the new product at the time of receiving the any training or coaching provided. In some embodiments, the recommendation may be based in part upon previous injury data that may be related to the individual's gait characteristics.

In some embodiments, retailer 1000 may stock many sensor modules 102 and use them interchangeably. As an example, a retailer 1000 may randomly select a pair of sensor modules 102 from a bin or charger containing perhaps dozens of sensor modules 102. The retailer 1000 may then use the electronic device 306 to register the individual 100, and pair the sensor modules 102 to the individual 100 utilizing the electronic device 306. The sensor modules 102 may also automatically determine which foot they have been placed on through motion recognition according to the data captured. When the data is finished recording, the sensor modules 102 may transmit by any means described herein, the recorded data to be viewed on the electronic device 306. In some embodiments, the electronic device 306 that receives the data from the sensor modules 102 may be different from the first electronic device 306 originally used to pair the sensor modules 102 to the individual 100. In some embodiments, the electronic device 306 may be used as a conduit for the sensor modules 102 to connect to a network and a database and a display to present the results of the athletic characteristic analysis, e.g. the gait characteristic analysis.

Once the individual is finished with data collection on the athletic activity, the retail enhancement system 10 may notify the retailer 1000 that the data collection is finished.

This may occur, for example, when the sensor module 102 is returned to a docking station. In other embodiments, this may happen each time a set of data is collected, regardless of whether the sensor modules 102 are docked.

In one embodiment, the characteristic or specific athletic movement data and/or any training or coaching provided may be used for the online customization of certain products. For example, this data can be used to customize an article of footwear, an article of compression clothing, a helmet, or other piece of clothing or athletic equipment to enable toe clothing or other equipment to help the individual 100 in improving their future performance. In some embodiments, customized products may have an individual styles, varied materials, or different accessories for the individual 100 to choose from.

By using a retail enhancement system 10 including one or more sensor modules 102, embodiments of the present invention described below may advantageously enable an individual (or a retailer 1000) to obtain this or other information about the motion of the individual's body or the motion of a piece of the individual's athletic equipment during the course of the athletic activity. Data obtained by sensor modules 102 may be processed in a variety of ways to yield useful information about the motion of an object of interest during the activity. In some embodiments, sensor module 102 data may be processed to monitor changes in the spatial orientation (i.e., changes in the position and/or rotation, relative to a specific location on the Earth or other point of reference) of the individual's body or a piece of the individual's athletic equipment. In other embodiment, sensor module 102 data may be processed to by reference to a predetermined correlation between movement data and a characteristic stored in a data structure and provide a recommendation regarding an article of footwear or other athletic equipment.

Retail enhancement system 10 according to embodiments of the present invention may include a sensor module 102. The sensor module 102 may include one or more sensors, and may be physically coupled to an object 104 during an athletic activity conducted by an individual 100. As explained in further detail below, the sensor module 102 may be used to monitor changes in the spatial orientation of the individual's 100 body or a piece of the individual's athletic equipment or article of footwear in some embodiments, while the sensor module 102 may be used in combination with predetermined correlation data stored in a data structure to determine a correlation between body or equipment or article of footwear movement data and a characteristic such as a gait characteristic in other embodiments.

In one embodiment, as illustrated in FIG. 1, the monitored object 104 may be the individual's 100 body, and the sensor module 102 may be physically coupled to the individual's 100 body. In the illustrated embodiment, the sensor module 102 is configured to be physically coupled to the portion of the individual's 100 body known as the foot by way of an object 104 which may be an article of footwear. In other embodiments, the sensor module 102 may be configured to be physically coupled to other portions of the individual's 100 body such as, for example, the individual's head, neck, shoulder, chest, back, arm, wrist, hand, finger, waist, hip, leg, ankle, foot, or toe.

In some embodiments, the sensor module 102 may be configured to be physically coupled to the portion of the individual's 100 body with one or more layers of clothing, an article of footwear, or athletic protective equipment existing between the sensor module 102 and the individual's 100 body. Regardless of whether intervening articles are present, the sensor module 102 may be physically coupled to the portion of the individual's 100 body by a variety of releasable or non-releasable coupling means such as, for example, straps, adhesives, pockets, clips, or by being integrated into an article of clothing (e.g., shirt, pants, sock, glove, or hat), footwear, or athletic protective equipment worn by the individual 100.

In one embodiment, the sensor module 102 may be configured to be placed in a sensor module 102 retention element of a garment or article of footwear that is configured to retain the sensor module 102. In some exemplary embodiments, retention element may be sized and shaped to correspond to the size and shape of the sensor module 102, to be capable of nesting sensor module 102 therein and holding the sensor module 102 in place so as to minimize the effect of movement of a wearer of the garment or article of footwear on the sensor module 102. Additional elements may be used to help minimize this effect, such as, for example, bands and spacer elements. The sensor module 102 retention element may be coupled to textile a layer of a garment or article of footwear by, for example, being integral therewith, being adhered, stitched, welded, tied, clipped, snapped, or mounted thereto, or any combination of these and other techniques. In some exemplary embodiments, sensor module 102 retention element is formed integrally with a textile layer of the garment or article of footwear.

In other embodiments, the sensor module 102 may be integrated within an existing piece of athletic activity monitoring equipment such as, for example, a heart rate monitoring device, a pedometer, and accelerometer-based monitoring device, positioning system receiver device (e.g. a GPS receiver), or other fitness monitoring device.

Figure 2B:
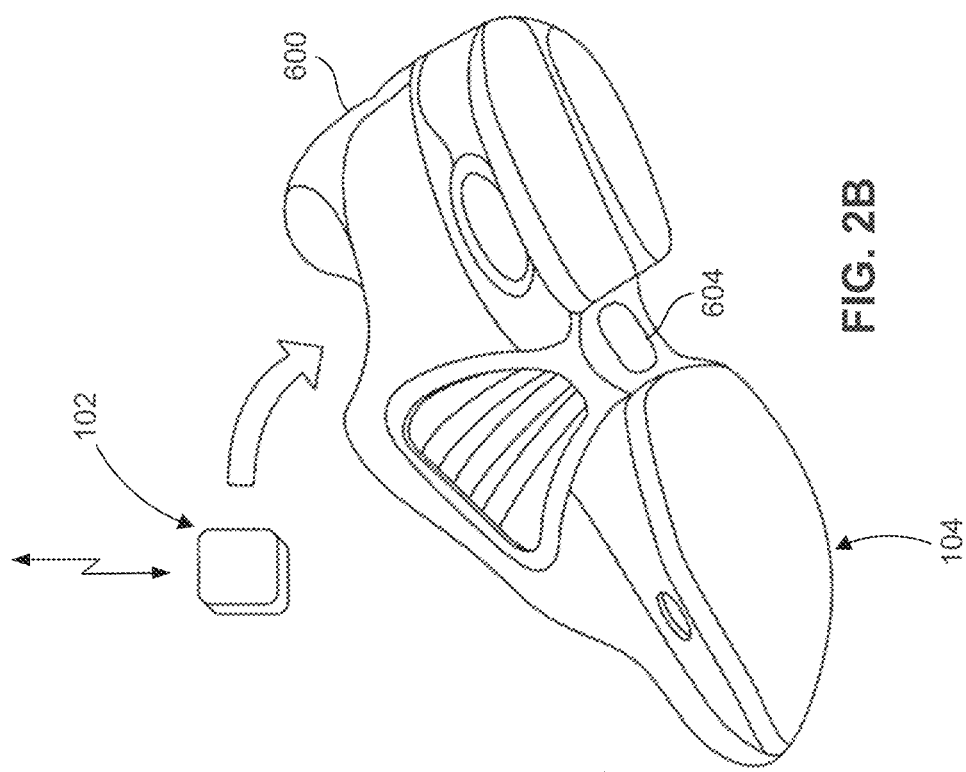
Figure 2A:
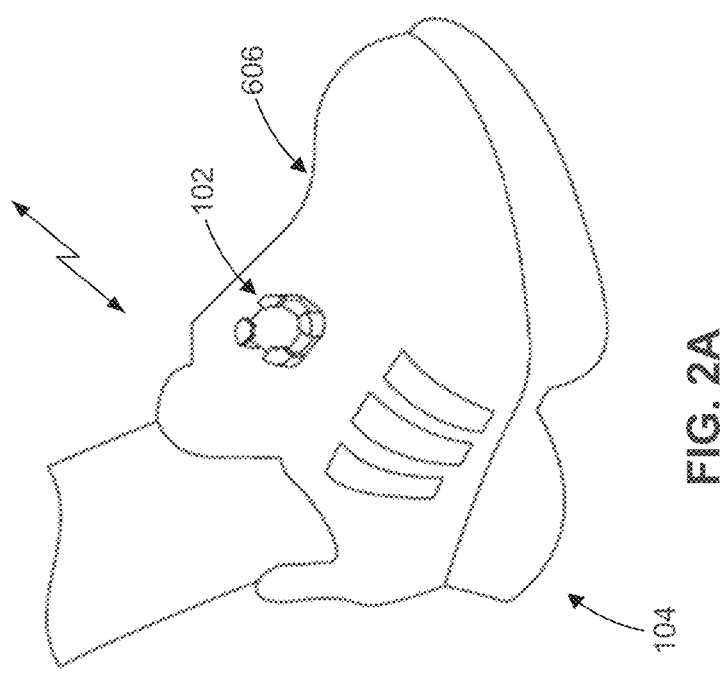

FIG. 2A is a diagram of an article of footwear 606 having sensor module 102 mounted on an external portion of article of footwear 606. As shown in FIG. 2A, sensor module 102 may be mounted using a mounting device 608. Mounting device 608 is held onto the top of article of footwear 606, for example, using article of footwear laces. Mounting device 608 permits sensor module 102 to be removed and inserted into the mounting device without taking the mounting device off of article of footwear 606.

FIG. 2B is a diagram of an article of footwear 600 having a sensor module 102 inserted into a recess in sole 604 of article of footwear 600 according to some embodiments of the present invention. The recess positions sensor module 102 in such a way that a surface of the sensor module's 102 housing is parallel to and in the plane of the top of sole 604. Placing sensor module 102 in the recess of sole 604 may be desirable because, in some embodiments, one of the acceleration sensor axis of sensor module 102 is parallel to the plane of the sensor module's 102 housing surface, and placing the sensor module 102 in this orientation may provide greater accuracy than other orientations such as, for example, attaching sensor module 102 to an external surface of article of footwear 600. In some embodiments, the recess in the sole that houses sensor module 102 is located in the mid-foot region of article of footwear 600 (e.g., where there is a minimum of flex of article of footwear 600).

In some embodiments, sensor module 102 is enclosed in a hard plastic protective housing. A surface of sensor module 102 includes a mark that is used to ensure proper orientation of sensor module 102, for example, when it is inserted into an article of footwear. In some embodiments, mark should be oriented facing towards the toe portion of the article of footwear. In other embodiments, however, the sensor module 102 will work properly regardless of orientation.

A second surface of sensor module 102 includes a removable cap. In some embodiments, removable cap is removed by turning it less than a quarter turn in one direction. Removable cap provides access to a battery, which can be removed and replace with a fully charged battery, as needed. In some embodiments, battery is a button type battery.

In some embodiments, the movement of the bodies of a plurality of individuals engaged in an athletic activity (e.g., multiple individuals or customers) and/or the movement of a plurality of pieces of athletic equipment used by the individuals during the athletic activity may be monitored. In some embodiments, real-time monitoring and/or feedback may be provided, while in other embodiments post-activity feedback may be provided.

Figure 3:
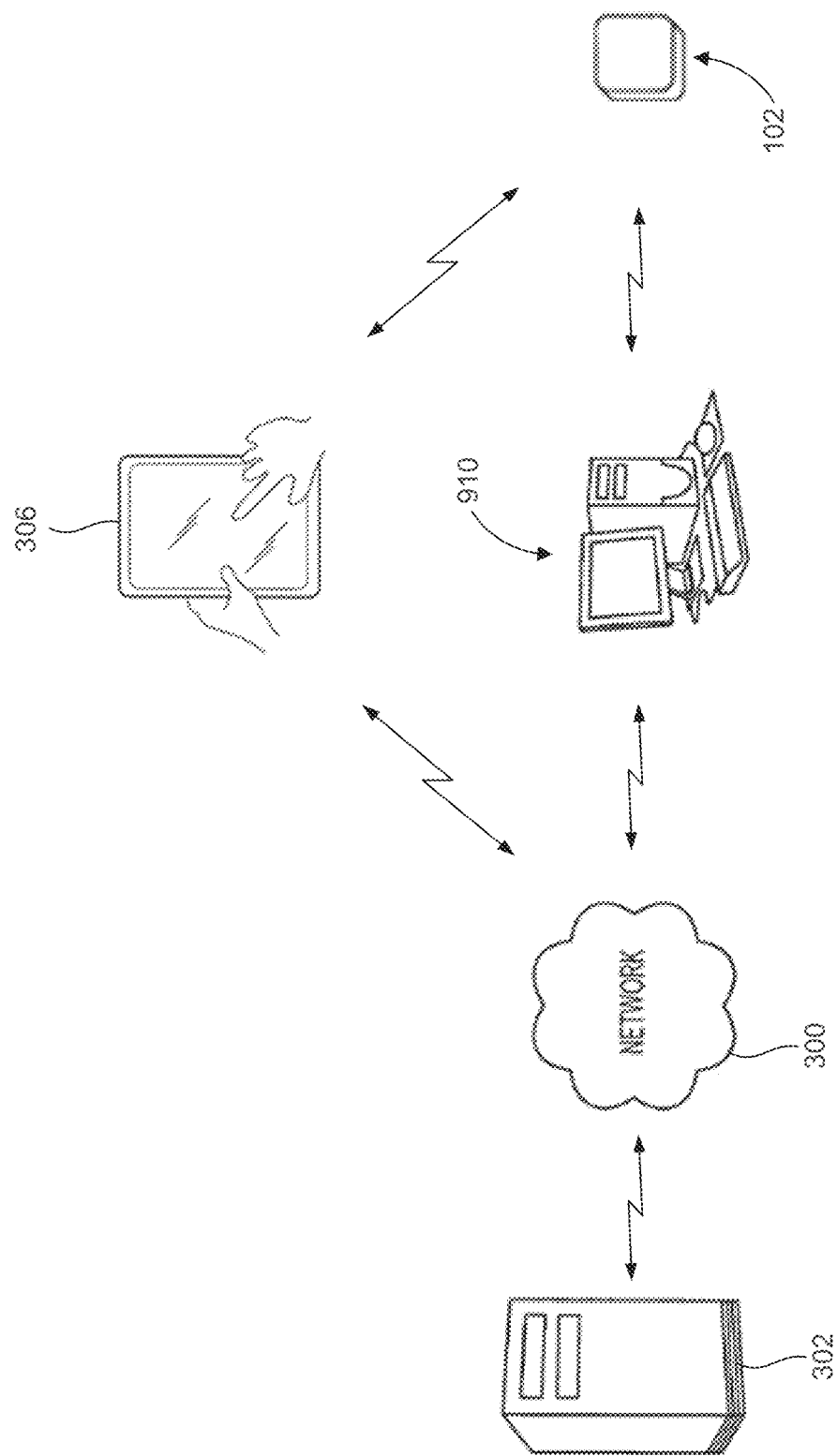
FIG. 3 is a diagram of a sensor module interacting with one of a retail device, an electronic device, a network, and a server according to an embodiment of the present invention.

As shown in FIG. 3, communication may also occur between the sensor module 102, an electronic device 306, and/or a remote server 302 via a network 300. In some embodiments, the network 300 is the Internet. The Internet is a worldwide collection of servers, routers, switches and transmission lines that employ the Internet Protocol (TCP/IP) to communicate data. The network 300 may also be employed for communication between any two or more of the sensor module 102, the electronic device 306, the server 302, and a docking unit. In some embodiments of the present invention, information is directly communicated between the sensor module 102 and the server 302 via the network 300, thus bypassing the electronic device 306.

A variety of information may be communicated between any of the sensor module 102, the electronic device 306, the network 300, the server 302, or other electronic components such as, for example, another sensor module 102, a mobile phone, a tablet computer, or other electronic devices, such as a retail device 910. Such information may include, for example, performance parameter data, device settings (including sensor module 102 settings), software, and firmware.

Communication among the various elements of the present invention may occur after the athletic activity has been completed or in real-time during the athletic activity. In addition, the interaction between, for example, the sensor module 102 and the electronic device 306, and the interaction between the electronic device 306 and the server 302 may occur at different times.

In some embodiments of the present invention, an individual 100 using the retail enhancement system 10 may participate in the activity with the sensor module 102 physically coupled to a piece of athletic equipment 104, but with no other electronic devices making up part of the retail enhancement system 10 in the individual's 100 immediate vicinity. In such some embodiments, the sensor module 102 would monitor the athletic activity using its sensors. The sensor module 102 may also perform calculations necessary to monitor changes in the spatial orientation of the piece of athletic equipment 104, or perform calculations necessary to determine a correlation between equipment 104 movement data and a characteristic.

Alternatively, in this scenario, other components of the retail enhancement system 10 that are remotely located from the individual 100 during the activity could be relied upon to perform calculations necessary to monitor changes in the spatial orientation of the piece of athletic equipment 104, or perform calculations necessary to determine a correlation between equipment 104 movement data and a characteristic. This could occur, for example after wireless transmission of athletic performance information directly from the sensor module 102 to an electronic device 306 or a server 302 during or after the activity, or after a wired transmission of athletic performance information directly from the sensor module 102 to an electronic device 306 after the activity.

In other embodiments, the sensor module 102 may communicate with an electronic device 306 of the retail enhancement system 10 that is also carried by the individual 100 during the athletic activity. In some embodiments, the electronic device 306 may be carried by another person besides the individual 100, or not carried by any person. In some embodiments, the electronic device 306 may be a watch, a mobile phone, a tablet computer, or other electronic device. In one embodiment of the present invention, as described in further detail below, in particular with respect to FIGS. 18-25, the sensor module 102 may communicate with an electronic device 306 running a retail enhancement system 10 electronic device 306 software application.

The electronic device 306 may serve a variety of purposes including, for example, providing additional data processing, providing additional data storage, providing data visualization, providing additional sensor capabilities, relaying information to a network 300, providing for the playback of music or videos, checking inventories, processing sales orders, processing sales transactions, inventory management, theft alert or the like.

In an embodiment providing theft alert capabilities, the electronic device 306 may alert the retailer 1000 if the individual 100 fails to return the sensor module 102 within an expected time, or if the individual 100 travels too far from the retail environment. In some embodiments, the retail enhancement system 10 may provide the personal information about the individual 100 to investigators. In some embodiments, the personal information may be known as "registration information." This personal information may include other personal identification information such as driver's license number, social security number, address, email, phone number, credit card information, and any other personal information used by the retail enhancement system 10. This personal information may also be used for other portions of the retail enhancement system 10, such as purchasing athletic equipment or articles of footwear that are recommended by the system, forwarding product information at a later date, using for marketing materials, and collecting information for the retailer 1000 or producer or manufacturer to use for engineering or business development purposes.

In one embodiment of the present invention, the electronic device 306 may be a dedicated electronic device 306. The term "dedicated electronic device" indicates that the electronic device 306 is not capable of serving another purpose outside of the retail enhancement system 10 of the present invention. For example, a mobile phone, a personal digital assistant, or a digital music file player (e.g., an MP3 player) may not be considered to be "dedicated electronic monitoring devices" as the term is used herein. In this manner, the dedicated electronic monitoring device 306 may in some embodiments provide a simpler and/or more efficient device.

The electronic device 306 illustrated in the figures may not be a dedicated electronic monitoring device; the electronic device 306 illustrated in the figures may be a tablet computer. In alternate embodiments, it may be possible for the sensor module 102 itself to be embodied by a mobile phone, or for the electronic device 306 to be a mobile phone. Including an electronic device 306 in the retail enhancement system 10, such as a mobile phone, may be desirable as mobile phones are commonly carried by individuals 100, even when engaging in athletic activities, and they are capable of providing significant additional computing and communication power at no additional cost to the individual 100.

In view of the above discussion, it is apparent that various processing steps or other calculations recited herein may be capable of being performed by various embodiments of the retail enhancement system 10 disclosed herein, and are not necessarily limited to being performed by the sensor module 102, depending on the configuration of a particular embodiment of the present invention. For example, any of the processing steps or other calculations recited herein may be performed, in various embodiments, by the sensor module 102, by a server computer 302, by an electronic device 306, and/or any other network component, or by more than one component.

Embodiments of the present invention may involve the use of so-called "cloud computing." Cloud computing may include the delivery of computing as a service rather than a product, whereby shared resources, software, and information are provided to computers and other devices as a utility over a network (typically the Internet). Cloud computing may entrust services (typically centralized) with an individual's 100 data, software and computation on a published application programming interface over a network. End users may access cloud-based applications through a web browser or a light weight desktop or mobile app while the business software and data are stored on servers at a remote location. Cloud application providers often strive to give the same or better service and performance than if the software programs were installed locally on end-user computers.

Embodiments of the present invention may incorporate features of motion monitoring systems. Exemplary of motion monitoring systems are disclosed in commonly owned U.S. patent application Ser. No. 13/077,494, filed Mar. 31, 2011 (which published as U.S. Patent App. Pub. No. 2012/0254934), the entirety of which is incorporated herein by reference thereto.

Figure 4:
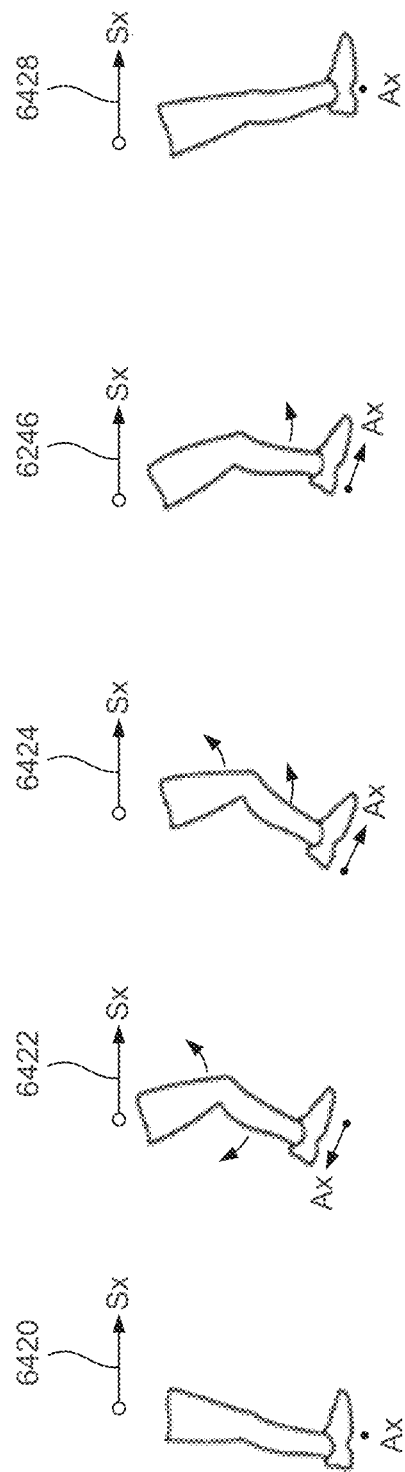
FIGS. 4 and 5 are diagrams of how one function of the sensor module may operate according to an embodiment of the present invention.
Figure 5:
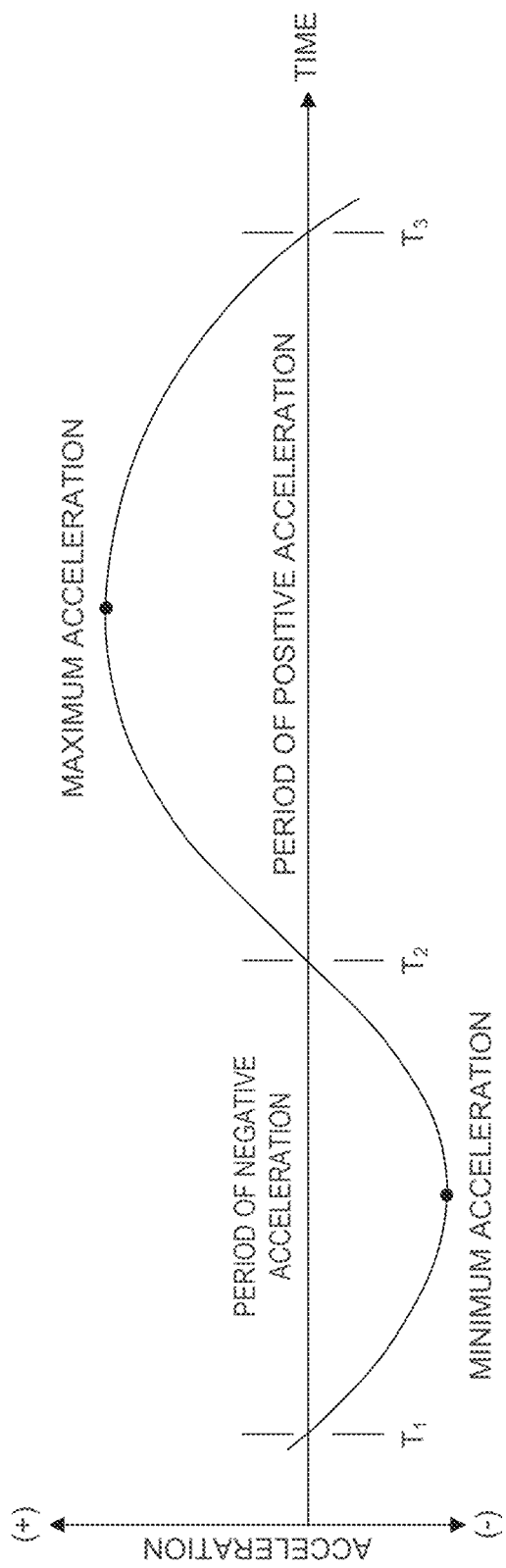

An overview of exemplary embodiments of components of the athletic equipment retail enhancement system 10 of the present invention, including exemplary sensor modules 102, has been provided above FIGS. 4 and 5 are diagrams that illustrate how the retail enhancement system 10 may determine performance data such as, for example, the speed, the pace, the stride rate, the stride length, and the total distance traveled by an individual in an embodiment of the present invention. In some embodiments, this data may be used in the recommendation of an article of footwear.

As shown in FIG. 4, an individual's leg has a specific movement pattern during each stride relative to the direction in which the individual is traveling (e.g., direction X). At a time period 6420, for example, the beginning of a stride, the foot of one leg of an individual is planted firmly on the ground and is not moving in the direction of travel. Since there is no movement of the foot, there is also no acceleration in the direction of travel. As the individual's hips and upper body move forward in the direction of travel at a speed $S_X$, the upper portion of the individual's leg begins to move forward at a time period 6422 relative to the direction in which the individual is traveling, while the lower portion of the individual's leg begins to move backwards relative to the direction of travel. This generates a negative acceleration in the direction of travel that is detected by a first axis (e.g., the X axis) of acceleration sensor 6406.

At a later point in time during the stride, time period 6424 in FIG. 4, the upper portion of the individual's leg is still moving forward relative to the direction of travel when the lower portion of the individual's leg begins to move forward relative to the direction of travel of the individual. This generates a positive acceleration in the direction of travel of the individual that is detected by the first axis of acceleration sensor 6406.

At a time period 6426 during the stride, the upper portion of the individual's leg has stopped moving forward relative to the direction of travel while the lower portion of the individual's leg is continuing to move forward relative to the direction of travel of the individual. This stage of the stride also generates a positive acceleration in the direction of travel of the individual that is detected by the axis of acceleration sensor 6406.

Finally, at the end of the stride, time period 6428 in FIG. 4, the individual's foot is again firmly planted on the ground. There is no movement of the foot in the direction of travel at this time period, and the acceleration along the first axis is zero.

FIG. 5 illustrates an idealized, filtered output of acceleration sensor of sensor module 102 corresponding to the stride of an individual (e.g., whether running or walking) As depicted, there is a period of negative acceleration having a minimum acceleration value and a period of positive acceleration having a maximum acceleration value during each stride. Using this information, the average speed of the individual in the direction of travel during the stride is given, for example, by equation 1 below:

$$S_X = K_1\{fx_1(A_{max}, T_3 - T_2)\} + K_2 \quad \text{EQ.1}$$

where $S_X$ is the average speed for the stride, $K_1$ is a proportionality constant, $fx_1$ is a function involving Amax (the maximum acceleration value generated during the stride processed through a low pass filter) and $T_3 - T_2$ (the period of positive acceleration), and $K_2$ is an adjustment constant. The values $K_1$ and $K_2$ are empirical values that are determined experimentally, and in an embodiment they are different for different ranges of speed (e.g., one set of values is used if an individual is walking and another set of values is used if the individual is running) The function $fx_1$ is determined experimentally, and in embodiments can be a higher order (e.g., a second order or a third order) equation.

In one embodiment, the value(s) for $K_1$ and/or $K_2$ are initially determined, for example, based on an input length for a user's leg (e.g., measured from the knee to the heel) or an input height for the user (e.g., using an assumption that the length of the leg is some fraction of the height).

In an embodiment, the value(s) for $K_1$ and/or $K_2$ are determined and/or updated by having the user run a known distance and using this known distance to determine and/or update the value(s) for $K_1$ and/or $K_2$.

As noted herein, it is possible to determine the average speed for the stride using the minimum acceleration value. This is done, for example, using equation 2 below:

$$S_X = K_3\{fx_2(A_{min}, T_2 - T_1)\} + K_4 \quad \text{EQ.2}$$

where $S_X$ is the average speed for the stride, $K_3$ is a proportionality constant, $fx_2$ is a function involving $A_{min}$ (the minimum acceleration value generated during the stride processed through a low pass filter) and $T_2 - T_1$ (the period of negative acceleration), and $K_4$ is an adjustment constant. The values $K_3$ and $K_4$ and the function $fx_2$ are determined experimentally. In embodiments, the function $fx_2$ can be a higher order (e.g., a second order or a third order) equation.

In one embodiment, the average speed is calculated by combining equations 1 and 2 and forming a third equation for the average speed during a stride. This third equation is:

$$S_X = K_1\{fx_1(A_{max}, (T_3 - T_2)\} - K_3\{fx_2(A_{min}, (T_2 - T_1)\} + K_{2+4} \quad \text{EQ.3}$$

where $S_X$ is the average speed for the stride, $K_1$ and $K_2$ are proportionality constants, $fx_1$ is a function involving Amax (the maximum acceleration value generated during the stride processed through a low pass filter) and $T_3-T_2$ (the period of positive acceleration), $fx_2$ is a function involving $A_{min}$ (the minimum acceleration value generated during the stride processed through a low pass filter) and $T_2-T_1$ (the period of negative acceleration), and $K_{2+4}$ is an adjustment constant. The values $K_1$, $K_3$ and $K_{2+4}$ and the functions $fx_1$ and $fx_2$ are determined experimentally. In embodiments, the functions $fx_1$ and $fx_2$ can be higher order (e.g., second order or third order) equations.

Using the information provided herein, it is possible to develop other algorithms for determining the average speed during a stride. For example, the output of more than one axes of acceleration sensor 6406 can be used, in which the output values would be combined using, for example, a square root of the sum of the squares approach. Accordingly, the present invention is not limited to using just the algorithms described herein.

Once the average speed for each stride is calculated, calculating other performance parameters is possible. For example, the distance traveled during each stride (e.g., stride length) is given by equation 4 below:

$$D_X = S_X(T_3-T_1) \qquad \text{EQ.4}$$

where $D_X$ is the stride length, $S_X$ is the average speed during the stride, and $T_3-T_1$ is the time of a single stride. Stride rate is determined by dividing 1 minute by $T_3-T_1$ to determine the number of strides per minute. The total distance traveled by the individual is the sum of all stride lengths. Pace is calculated, for example, by inverting the average speed value and adjusting the unit to obtain a desired time per distance value (e.g., minutes per kilometer, minute per mile, et cetera).

It is to be noted that while the values for $K_1$ and $K_2$ can be determined and selected based on information provided by a user (e.g., by asking a user to provide the length of his or her leg or his or her height), it is desirable to have the individual walk or run a particular known distance and use this information to adjust the values for $K_1$ and $K_2$ (i.e., to calibrate sensor module 102 for the particular user). Doing this leads to improved accuracy. Additionally, it may also be beneficial to have one set of K values that are used in an algorithm when a user is walking and another set of K values that are used when the user is running Whether the user is walking or running can be determined, for example, using a threshold acceleration value. For example, if the maximum acceleration value detected is below a certain threshold, it is assumed that the user is walking Otherwise, it is assumed the user is running.

In an embodiment, calibration of sensor module 102 is performed using, for example, received GPS signals. The received GPS signals can be used, for example, to determine a distance that a user runs or walks during a workout.

In one embodiment, sensor modules 102 according to the present invention are used to detect changes in an individual's direction of motion. Sensor modules 102 according to the present invention can also be worn by individuals and used to detect and/or track other motions such as, for example, motions associated with push-ups, pull-ups, weightlifting, diving, gymnastics, et cetera.

Turning to FIG. 6A, a block diagram of components of a sensor module 102 according to some embodiments of the present invention is shown. In the illustrated embodiment, the sensor module 102 includes a processor 110, a power source 112, a memory 114, an acceleration sensor 116, a magnetic field sensor 118, and a transceiver 122 operatively connected to one another to carry out the functionality of the sensor module 102. In other embodiments, one or more of these sensor module 102 components may be omitted, or one or more additional components may be added.

The processor 110 may be adapted to implement application programs stored in the memory 114 of the sensor module 102. The processor 110 may also be capable of implementing analog or digital signal processing algorithms such as raw data reduction and filtering. For example, processor 110 may be configured to receive raw data from sensors and process such data at the sensor module 102. The processor 110 is operatively connected to the power source 112, the memory 114, the acceleration sensor 116, the magnetic field sensor 118, and the transceiver 122.

The power source 112 may be adapted to provide power to the sensor module 102. In one embodiment, the power source 112 may be a battery. The power source may be built into the sensor module 102 or removable from the sensor module 102, and may be rechargeable or non-rechargeable. In some embodiments, the power source 112 may be recharged by a cable attached to a charging source, such as a universal serial bus ("USB") FireWire, Ethernet, Thunderbolt, or headphone cable, attached to a personal computer. In another embodiment, the power source 112 may be recharged by inductive charging, wherein an electromagnetic field is used to transfer energy from an inductive charger to the power source 112 when the two are brought in close proximity, but need not be plugged into one another via a cable. In some embodiment, a docking station may be used to facilitate charging. In other embodiments, the sensor module 102 may be repowered by replacing one power source 112 with another power source 112.

The memory 114 may be adapted to store application program instructions and to store athletic activity data. In some embodiments, the memory 114 may store application programs used to implement aspects of the functionality of the retail enhancement system 10 described herein. In one embodiment, the memory 114 may store raw data, recorded data, and/or calculated data. In some embodiments, as explained in further detail below, the memory 114 may act as a data storage buffer. The memory 114 may include both read only memory and random access memory, and may further include memory cards or other removable storage devices.

In some embodiments of the present invention, the memory 114 may store raw data, recorded data, and/or calculated data permanently, while in other embodiments the memory 114 may only store all or some data temporarily, such as in a buffer. In one embodiment of the present invention, the memory 114, and/or a buffer related thereto, may store data in memory locations of predetermined size such that only a certain quantity of data may be saved for a particular application of the present invention.

The acceleration sensor 116 may be adapted to measure the acceleration of the sensor module 102. Accordingly, when the sensor module 102 is physically coupled to an object 104 (such as an individual's 100 body or a piece of athletic equipment, or article of footwear described above), the acceleration sensor 116 may be capable of measuring the acceleration of the object 104, including the acceleration due to the earth's gravitational field. In one embodiment, the acceleration sensor 116 may include a tri-axial accelerometer that is capable of measuring acceleration in three orthogonal directions. In other embodiments one, two, three, or more separate accelerometers may be used.

The magnetic field sensor 118 may be adapted to measure the strength and direction of magnetic fields in the vicinity of the sensor module 102. Accordingly, when the sensor module 102 is physically coupled to an object 104 (such as an individual's 100 body or a piece of athletic equipment, or article of footwear described above), the magnetic field sensor 118 may be capable of measuring the strength and direction of magnetic fields in the vicinity of the object 104, including the earth's magnetic field. In one embodiment, the magnetic field sensor 118 may be a vector magnetometer. In other embodiments, the magnetic field sensor 118 may be a tri-axial magnetometer that is capable of measuring the magnitude and direction of a resultant magnetic vector for the total local magnetic field in three dimensions. In other embodiments one, two, three, or more separate magnetometers may be used.

In one embodiment of the present invention, the acceleration sensor 116 and the magnetic field sensor 118 may be contained within a single accelerometer-magnetometer module bearing model number LSM303DLHC made by STMicroelectronics of Geneva, Switzerland. In other embodiments, the sensor module 102 may include only one of the acceleration sensor 116 and the magnetic field sensor 118, and may omit the other if desired.

The transceiver 122 depicted in FIG. 6A may enable the sensor module 102 to wirelessly communicate with other components of the retail enhancement system 10, such as those described in further detail below. In one embodiment, the sensor module 102 and the other local components of the retail enhancement system 10 may communicate over a personal area network or local area network using, for example, one or more of the following protocols: ANT, ANT+ by Dynastream Innovations, Bluetooth, Bluetooth Low Energy Technology, BlueRobin, or suitable wireless personal or local area network protocols. Other known communication protocols suitable for a retail enhancement system 10 may also be used.

In one embodiment, the transceiver 122 is a low-power transceiver. In some embodiments, the transceiver 122 may be a two-way communication transceiver 122, while in other embodiments the transceiver 122 may be a one-way transmitter or a one-way receiver. Wireless communication between the sensor module 102 and other components of the retail enhancement system 10 is described in further detail below. In other embodiments, the sensor module 102 may be in wired communication with other components of the retail enhancement system 10 that does not rely on transceiver 122.

In some embodiments of the present invention, a sensor module 102 having components such as those depicted in FIG. 6A may be physically coupled to an object 104 during an athletic activity conducted by an individual 100 to monitor changes in the spatial orientation of the individual's 100 body or a piece of the individual's athletic equipment or article of footwear, or to determine a correlation between body or equipment movement data and a characteristic such as gait characteristic. In these embodiments, the acceleration sensor 116 and the magnetic field sensor 118 may be responsible for collecting the data necessary to carry out the various monitoring calculations.

In some other embodiments, however, it may be desirable to have additional sensors included within the sensor module 102, or to have additional sensors in communication with the sensor module 102. In further embodiments, the sensor module 102 may be integrated within an existing piece of athletic activity monitoring equipment possibly having additional or different sensors such as, for example, a heart rate monitoring device, a pedometer, and accelerometer-based monitoring device, or other fitness monitoring device.

In addition to the acceleration sensor 116 and the magnetic field sensor 118, other sensors that may be part of the sensor module 102 or separate from but in communication with the sensor module 102 may include sensors capable of measuring a variety of athletic performance parameters. The term "performance parameters" may include physical parameters and/or physiological parameters associated with the individual's 100 athletic activity. Physical parameters measured may include, but are not limited to, time, distance, speed, pace, pedal count, wheel rotation count, rotation generally, stride count, stride length, airtime, stride rate, altitude, strain, impact force, jump force, force generally, and jump height. Physiological parameters measured may include, but are not limited to, heart rate, respiration rate, blood oxygen level, blood lactate level, blood flow, hydration level, calories burned, or body temperature.

FIG. 6B is a block diagram of components of a sensor module 102 according to another embodiment of the present invention that may incorporate some of the additional sensors mentioned above, as well as other additional components. In the illustrated embodiment, the sensor module 102 includes a processor 110, a power source 112, a memory 114, an acceleration sensor 116, a magnetic field sensor 118, a user interface 120, and a transceiver 122, an angular momentum sensor 124, a heart rate sensor 126, a temperature sensor 128, a position receiver 130, a data port 132, and a timer 134 operatively connected to one another to carry out the functionality of the sensor module 102. In other embodiments, one or more of these sensor module 102 components may be omitted, or one or more additional components may be added.

The processor 110, the power source 112, the memory 114, the acceleration sensor 116, the magnetic field sensor 118, and the transceiver 122 of the embodiment of FIG. 6B may have structures and functions similar to those described above with respect to analogous components in FIG. 6A. In some embodiments, the transceiver 122 may be a two-way communication transceiver 122, while in other embodiments the transceiver 122 may be a one-way transmitter or a one-way receiver.

The user interface 120 of the sensor module 102 may be used by the individual 100 to interact with the sensor module 102. In some embodiments, the user interface 120 may include one or more input buttons, switches, or keys, including virtual buttons, switches, or keys of a graphical user interface touch screen surface. The function of each of these buttons, switches, or keys may be determined based on an operating mode of the sensor module 102. In one embodiment, the user interface 120 may include a touch pad, scroll pad and/or touch screen. In another embodiment, the user interface 120 may include capacitance switches. In a further embodiment, the user interface 120 may include voice-activated controls.

In some embodiments, however, the sensor module 102 may not include a user interface 120. In these embodiments, the sensor module 102 may be capable of communicating with other components of the retail enhancement system 10 which may themselves include user interfaces.

The angular momentum sensor 124, which may be, for example, a gyroscope, may be adapted to measure the angular momentum or orientation of the sensor module 102. Accordingly, when the sensor module 102 is physically coupled to an object 104 (such as an individual's 100 body or athletic equipment), the angular momentum sensor 124 may be capable of measuring the angular momentum or orientation of the object 104. In one embodiment, the angular momentum sensor 124 may be a tri-axial gyroscope that is capable of measuring angular rotation about three orthogonal axis. In other embodiments one, two, three, or more separate gyroscopes may be used. In some embodiments, the angular momentum sensor 124 may be used to calibrate measurements made by one or more of the acceleration sensor 116 and the magnetic field sensor 118.

The heart rate sensor 125 may be adapted to measure an individual's heart rate. The heart rate sensor 125 may be placed in contact with the individual's 100 skin, such as the skin of the individual's chest, and secured with a strap. The heart rate sensor 125 may be capable of reading the electrical activity the individual's 100 heart.

The temperature sensor 128 may be, for example, a thermometer, a thermistor, or a thermocouple that measures changes in the temperature. In some embodiments, the temperature sensor 128 may primarily be used for calibration other sensors of the retail enhancement system 10, such as, for example, the acceleration sensor 116 and the magnetic field sensor 118.

In one embodiment, the position receiver 130 may be an electronic satellite position receiver that is capable of determining its location (i.e., longitude, latitude, and altitude) using time signals transmitted along a line-of-sight by radio from satellite position system satellites. Known satellite position systems include the GPS system, the Galileo system, the BeiDou system, and the GLONASS system. In another embodiment, the position receiver 130 may be an antennae that is capable of communicating with local or remote base stations or radio transmission transceivers such that the location of the sensor module 102 may be determined using radio signal triangulation or other similar principles. In some embodiments, position receiver 130 data may allow the sensor module 102 to detect information that may be used to measure and/or calculate position waypoints, time, location, distance traveled, speed, pace, or altitude.

The data port 132 may facilitate information transfer to and from the sensor module 102 and may be, for example, a USB port. In some exemplary embodiments, data port 132 can additionally or alternatively facilitate power transfer to power source 112, in order to charge power source 112.

The timer 134 may be a clock that is capable of tracking absolute time and/or determining elapsed time. In some embodiments, the timer 134 may be used to timestamp certain data records, such that the time that certain data was measured or recorded may be determined and various timestamps of various pieces of data may be correlated with one another.

In some embodiments of the present invention, a sensor module 102 having components such as those depicted in FIG. 6B may be physically coupled to an object 104 during an athletic activity conducted by an individual 100 to monitor changes in the spatial orientation of the individual's 100 body or a piece of the individual's athletic equipment or article of footwear, or to determine a correlation between body or equipment movement data and a characteristic such as gait characteristic. In these embodiments, the acceleration sensor 116, the magnetic field sensor 118, and/or other included sensors may be responsible for collecting the data necessary to carry out the various monitoring calculations. In some other embodiments, however, it may be desirable to have additional sensors included within the sensor module 102, to have additional sensors in communication with the sensor module 102, or to have fewer sensors with the sensor module 102.

As illustrated in FIG. 6A, in one embodiment, the sensor module 102 may include a housing 136. The housing 136 may contain and protect the various electronic components of the exemplary sensor modules 102 described above with reference to FIG. 6A or FIG. 6B. The housing may take on any suitable size and shape that is able to accommodate the necessary components of the sensor module 102 and to physically couple to the desired part of the individual's 100 body. In one embodiment, the housing may be made of plastic, such as, for example, TPU, or other suitably durable material.

In some embodiments, the sensor module 102 may also include a button and/or a display. The button may serve as the user interface of the sensor module 102. The button may be capable of turning the sensor module 102 on and off, toggling through various display options, or serving a variety of other functions. Alternatively, multiple buttons or no buttons may be provided. In one embodiment, the display may be a relatively simple LED display that is capable of conveying the status or battery life of the sensor module 102 to an individual 100 with different color combinations or flashing patterns, for example. In another embodiment, the display may be a more advanced display that is capable of displaying performance parameter information, feedback, or other information to the individual 100, such as a seven-segment LCD display. Alternatively, no button or display may be provided, as illustrated in FIG. 2A and FIG. 2B.

In other embodiments, the sensor module 102 may include audio controls such as a speaker and/or microphone for audio communication with an individual 100. These components may serve as the user interface of the sensor module 102. These audio controls may be capable of turning the sensor module 102 on and off, toggling through various display options, or serving a variety of other functions. In one embodiment, the audio controls may be capable of conveying the status or battery life of the sensor module 102 to an individual 100. In another embodiment, the audio controls may be capable of outputting or receiving performance parameter information, feedback, or other information to and from the individual 100. In one embodiment, the audio controls may be capable of accepting voice commands form the individual 100. In another embodiment, the sensor module 102 may be capable of relaying audio information to a user wirelessly via another device, such as a pair of headphones. Alternatively, audio controls may be provided.

Data obtained by the sensor module 102 may be processed in a variety of ways to yield useful information about the motion of an object 104 of interest during the activity. In some embodiments, sensor module 102 data may be processed to monitor changes in the spatial orientation of the individual's 100 body or a piece of the individual's 100 athletic equipment. In other embodiment, sensor module 102 data may be processed to by reference to a predetermined correlation between movement data and a characteristic stored in a data structure.

FIG. 7A is a more detailed diagram of a first example electronic device 306 according to an embodiment of the present invention. In an embodiment, electronic device 306 corresponds to a tablet computer. Alternatively, the electronic device may be a retail register, desktop computer, mobile computing device, mobile phone, and the like. As shown in FIG. 7A, electronic device 306 may include a processor 2302, memory 2304, a user input control 1306, a display 308, an audio unit 310, a transceiver 312, a cellular transceiver 316, an optional satellite-based positioning system receiver 305, a camera 309, and a battery 320.

Processor 2302 is a conventional processor capable of implementing application programs stored in memory 2304. Processor 2302 is also capable of implementing digital signal processing algorithms. Processor 2302 is coupled to memory 304, user input control 1306, display 308, audio unit 310, transceiver 312, and may include a cellular transceiver 316.

Memory 2304 is used to store application program instructions and data. In an embodiment, memory 2304 stores programs, for example, used to implement all of the functionality of a typical tablet computer. In an embodiment, memory 2304 includes both read only memory and random access memory.

User input control 1306 is used by an individual to interact with electronic device 306. In an embodiment, user input control 1306 includes a variety of input buttons and/or keys. The function of each of these buttons and/or keys is typically determined based on an operating mode of electronic device 306. In one embodiment, user input control 1306 includes a touch pad or scroll pad and/or touch screen buttons.

Display 308 is used to display information to a user. In an embodiment, display 308 is a liquid crystal display.

Camera 309 is a small digital camera used to take digital photos or video. In one embodiment, camera 309 is a CCD camera. In another embodiment, camera 309 is a CMOS camera.

Audio unit 310 is used to process audio signals. In an embodiment, voice signals picked up using a microphone are converted to digital signals so that they can be operated upon, for example, by processor 2302. Audio unit 310 also converts, for example, digital audio signals into amplified analog audio signals that can be used to drive one or more speakers. In an embodiment, audio unit 310 implements signal processing algorithms such as those available from Dolby Laboratories, Inc., which enhance the quality of music.

Transceiver 312 is a low-power transceiver used to communicate with other components of retail enhancement system 10. In an embodiment, transceiver 312 operates in an unlicensed frequency band such as 2.4 GHz. Transceiver 312 is coupled to an antenna 314. As used herein, the term transceiver means a combination of a transmitter and a receiver. In an embodiment, the transmitter and the receiver are integrated and form, for example, a part of an intergraded circuit.

Cellular transceiver 316 may be used to send and receive, for example, voice cellular telephone signals. Transceiver 316 can also be used to exchange information with a computer network such as, for example, the Internet. Cellular transceiver 316 is coupled to an antenna 318. As used herein, the term cellular transceiver means a combination of a cellular transmitter and a cellular receiver. In an embodiment, the transmitter and the receiver are integrated together into a single device.

In one embodiment, cellular transceiver 316 is used to send data described herein to a location where it is analyzed, for example, by a professional trainer. The professional trainer can call or text message the individual and provide the individual real-time feedback based on the data. If the individuals wants to call the professional trainer, for example, during a workout, the individual can place a call to the professional trainer, for example, by tapping electronic device 306 to place a call to a stored telephone number. In one embodiment, tapping electronic device 306 sends a text message to the professional trainer requesting that the professional trainer call the individual.

Battery 320 is used to provide power to operate the various components of electronic device 306. In an embodiment, battery 320 is recharged periodically using a power adapter that plugs into a typical household power outlet. Battery 320 can also be a non-rechargeable battery.

In an embodiment, electronic device 306 also includes an optional satellite-based positioning system (e.g., global positioning system (GPS) or Galileo system) receiver 305. This enables the electronic device to determine its location anywhere on the earth. The satellite-based positioning system (e.g., GPS) receiver 305 is coupled to an antenna 307.

In an embodiment, GPS receiver 305 enables the electronic device 306, for example, to provide navigational instructions to a runner using the device. The directions for a running route can be downloaded to the electronic device prior to a run and stored in memory 2304. In addition to navigational instructions, attributes about the running route such as, for example, whether the route has sidewalks, is on a trail, is located within a safe neighborhood, et cetera, can also be downloaded and viewed.

GPS receiver 305 can be used, in an embodiment, to track a route run by a runner. The route can be saved in memory 304 and viewed by the runner after the run. The route can also be shared with other runners, for example, by posting the route on a computer/web server for down-loading by other runners.

In an embodiment, GPS receiver 305 and information stored in the memory of electronic device 306 (or information received, e.g., from the internet using cellular transceiver 316) are used to provide navigational instructions, for example, to a runner. In an embodiment, the runner can enter into electronic device 306 that he or she would like to run five kilometers, for example, and the electronic device will automatically select/map-out an appropriate route and provide navigation instructions to the runner during the run. In an embodiment, the runner can specify both a start point and a stop point for the run. In an embodiment, only one point is specified, which serves as both the start point and the stop point. In an embodiment, the start and stop points are the point at which the runner is standing (e.g., as determined by GPS receiver 305) when the runner enters, for example, that he or she would like to run five kilometers.

In an embodiment, electronic device 306 includes a radio. The radio can be an AM only radio, an FM only radio, or both an AM and FM radio. In an embodiment, the radio is controlled using soft keys presented to a user on display 308.

In one embodiment, electronic device 306 includes optional sensors (not shown) for detecting selected weather related data such as, for example, temperature, humidity, ultra-violet radiation and/or barometric pressure. This data can be used, for example, to determine how an individual's performance is effected by environmental factors.

In one embodiment, a electronic device according to the present invention does not include a display. In this embodiment, information such as, for example, performance and/or feedback information is provided to a user audibly during a workout. The information can be display to the user, for example, after the workout using a computer display once the information has been transferred to the computer. In an embodiment, the information can be transferred to a second processing device such as, for example, a sports watch during the workout and displayed to the user during the workout on the display of the second processing device.

FIG. 7B is a diagram of an example electronic device 306 according to an embodiment of the present invention. In an embodiment, electronic device 306 corresponds to a device such as, for example, at tablet computer, retail register kiosk, desktop computer, a PDA device, MP3 player, or an electronic watch having a sports operating mode. As shown in FIG. 7B, electronic device 306 includes a processor 352, memory 354, a user input control 356, a display 358, an audio unit 360, a transceiver 362, and a battery 366.

Processor 352 is a conventional processor capable of implementing application programs stored in memory 354. Processor 352 is also capable of implementing digital signal processing algorithms. Processor 352 is coupled to memory 354, user input control 356, display 358, audio unit 360, and transceiver 362.

Memory 354 is used to store application program instructions and data. In an embodiment, memory 354 stores programs, for example, used to implement all of the functionality of a typical PDA, MP3 player, or electronic watch and one or more programs used to implement aspects of the functionality of retail enhancement system 10 described herein. In an embodiment, memory 354 includes both read only memory and random access memory.

User input control 356 is used by an individual to interact with electronic device 306. In an embodiment, user input control 356 includes a variety of input buttons and/or keys. The function of each of these buttons and/or keys is typically determined based on an operating mode of electronic device 306. In one embodiment, user input control 356 includes a touch pad or scroll pad and/or touch screen buttons.

Display 358 is used to display information to a user. In an embodiment, display 358 is a liquid crystal display.

Audio unit 360 is used to process audio signals. In an embodiment, audio unit 360 converts, for example, digital audio signals into amplified analog audio signals that can be used to drive one or more speakers. In an embodiment, audio unit 360 implements signal processing algorithms such as those available from Dolby Laboratories, Inc., which enhance the quality of music.

Transceiver 362 is a low-power transceiver used to communicate with other components of retail enhancement system 100. In an embodiment, transceiver 362 operates in an unlicensed frequency band such as 2.4 GHz. Transceiver 362 is coupled to an antenna 364.

Battery 366 is used to provide power to operate the various components of electronic device 306. In an embodiment, battery 366 is recharged periodically using a power adapter that plugs into a typical household power outlet. Battery 366 can also be a non-rechargeable battery.

In embodiments, a electronic device according to the present invention can be formed, for example, by attaching a dongle (e.g., a small hardware device that protects software) to a conventional phone, a music file player, a personal digital assistant, et cetera. The dongle includes, for example, downloadable software that implements some or all of the sport functions described herein. In an embodiment, the software includes a sport user interface written in the Java programming language. In an embodiment, the software includes drivers, for example, that enable the software to be used with any ultra low power Bluetooth communications protocol compatible device. Other embodiments are compatible with other communications protocol compatible devices.

In an embodiment of the present invention, a electronic device according to the present invention is a dedicated device (rather than a device such as, for example, a phone, a music file player, or a personal digital assistant) that implements the sports electronic retail enhancement functions as detailed herein.

A coordinate axis system is a useful analytical tool for monitoring changes in the spatial orientation of an object 104. FIG. 8A illustrates an exemplary three-dimensional Cartesian coordinate axis system 350. This system 350 defines six degrees of freedom for a rigid body, such as the object 104. Six degrees of freedom refers to motion of a rigid body in three-dimensional space, namely the ability to move forward/backward, up/down, left/right (translation in three perpendicular axes) combined with rotation about three perpendicular axes (pitch, yaw, roll), as illustrated in the figure.

FIG. 8B illustrates another exemplary three-dimensional Cartesian coordinate axis system 300 having three axes—an X axis, a Y axis, and a Z axis. Two vectors, "G" and "B," are superimposed on the coordinate axis system 300 illustrated in FIG. 8B. The G-vector 1302 pointing in the −Y direction represents a gravity vector. The B-vector 1304 represents a resultant magnetic field vector.

Regardless of whether the retail enhancement system 10 and the sensor module 102 are being used to monitor the individual's 100 body or a piece of the individual's 100 athletic equipment, in embodiments of the present invention where there is a desire to monitor changes in the spatial orientation of the individual's 100 body or the piece of the individual's 100 athletic equipment, a common analytical framework may be used to carry out the monitoring. This analytical framework is illustrated by FIG. 9.

With reference to FIG. 9, in such some embodiments, the individual 100 may use the sensor module 102 in the retail enhancement system 10 to determine a change in spatial orientation of the object 104 according to spatial orientation process 400 as follows. As discussed above, the object in some embodiments may be an article of footwear, and the motion may include running, walking, jogging, and the like. In some embodiments the spatial orientation change detected may be utilized for correlating gait characteristics such as foot strike type, rate of pronation, degree of pronation, and the like.

First, at step 402, the sensor module 102 may detect movement of the object 104. In one embodiment, movement of the object 104 is detected based on acceleration data captured by the acceleration sensor 116 of the sensor module 102. In another embodiment, movement of the object 104 is detected based on magnetic field data captured by the magnetic field sensor 118 of the sensor module 102. In yet another embodiment, movement of the object 104 is detected based on both acceleration data and magnetic field data.

In one embodiment, the magnetic field sensor 118 may be adapted to measure the strength and direction of magnetic fields in the vicinity of the sensor module 102. In another embodiment, the magnetic field sensor 118 may be adapted to measure the strength and direction of the earth's magnetic field in the vicinity of the sensor module 102. In some embodiments, the magnetic field sensor 118 may be capable of measuring the magnitude and direction of a resultant magnetic vector for the total local magnetic field and/or for the local earth's magnetic field.

In some embodiments, the sensor module 102 may then determine that the movement of the object 104 indicates the occurrence of a movement to track. In one embodiment, the determination that the movement of the object 104 indicates the occurrence of a movement to track occurs when a threshold data value is met for a predetermined period of time. For example, the sensor module 102 may determine that a movement of the object 104 has resulted in a threshold acceleration and/or magnetic field change occurring for a predetermined period of time.

In some embodiments, the determination of the occurrence of a movement to track is an indication that the movement to track had already begun prior to the determination. In this case, it is still possible to capture all of the relevant data relating to the movement as the sensor module 102 may temporarily record a stream of data in a buffer in the event that data that had recently been recorded may need to be examined or more permanently recorded in response to a determination that an occurrence of a movement to track is found. In other embodiments, the determination of the occurrence of a movement to track is an indication that the movement to track is about to begin in the near future. In some embodiments, the sensor module 102 is adapted to store data permanently or temporarily, and may further be adapted to store data for predefined periods of time in certain circumstances, such as when populating a data buffer.

Next, as step 406, in response to the determination of the occurrence of a movement to track, an initial spatial orientation of the object 104 may be determined. In some embodiments, the determination of an initial spatial orientation of the object 104 may be made by reference to a coordinate axis system.

Returning to the discussion of step 406, in one embodiment, the determination of the initial spatial orientation of the object 104 may be made with respect to a gravity vector 302, such as that illustrated in FIG. 8B. In another embodiment, the determination of the initial spatial orientation of the object 104 may be made with respect to an earth magnetic field vector 304, such as that illustrated in FIG. 8B. In other embodiments, the determination of the initial spatial orientation of the object 104 may be made with respect to characterizations of the way that the object translated and rotated in three-dimensional space with six degrees of freedom, as explained with reference to FIG. 8B.

At step 408, after the determination of the initial orientation of the object 104 at a first time has been made, a change in the spatial orientation of the object 104 may be determined. In some embodiments, the determination of the change in the spatial orientation of the object 104 at step 408 may be made similarly to the determination of the initial orientation of the object 104 at step 406, except that additional information about changes in the orientation of the gravity vector 302 and/or the magnetic field vector 304 as the object moves may be additionally factored in.

At step 410, a characteristic is determined based on the change in the spatial orientation of the object 104 determined in step 408. The nature of the characteristic may change based on the athletic activity that the individual 100 is participating in, as well as particular object 104 that is being monitored. In one embodiment, the characteristic may relate to, for example, a speed, a jump height, a jump force, a jump distance, a jump trajectory, an athletic activity force, an athletic activity distance, an impact force, a characterization of a specific type of athletic movement, or a reaction time measurement. In other embodiments, the characteristic may be, for example, the rate of rotation, the plane of rotation, the jump force, force profile (force acting upon the body of the athlete or the ground or the object), or gait characteristics. Again, as discussed above, the object in some embodiments may be an article of footwear, and the motion may include running, walking, jogging, and the like. In some embodiments the spatial orientation change detected may be utilized for correlating gait characteristics such as foot strike type, rate of pronation, degree of pronation, and the like.

Finally, at step 412, an output is provided that conveys the characteristic to the individual 100, a retailer 1000, or any other interested person. In one embodiment, the output may be an audible, visual, and/or haptic output. In some embodiments the spatial orientation change detected may be utilized for correlating gait characteristics such as foot strike type, rate of pronation, degree of pronation, and the like.

In some embodiments of the present invention, instead of a desire to monitor changes in the spatial orientation of an object 104 of interest, there may be a desire to correlate movements of objects 104, such as the individual's 100 body or the piece of the individual's 100 athletic equipment, to characteristics based on a predetermined correlation stored in a data structure. A common analytical framework may be used to carry out such correlations. This analytical framework is illustrated by FIG. 10. As discussed above, the object in some embodiments may be an article of footwear, and the motion may include running, walking, jogging, and the like. In some embodiments the spatial orientation change detected may be utilized for correlating gait characteristics such as foot strike type, rate of pronation, degree of pronation, and the like.

With reference to FIG. 10, in such some embodiments, the individual 100 may use the sensor module 102 in the retail enhancement system 10 to determine such correlations to object 104 movement according to movement correlation process 420 as follows.

First, at step 422, the sensor module 102 may detect movement of the object 104. This step may be carried out in a similar fashion to step 402 of the spatial orientation process 400, as described above.

In some embodiments, the sensor module 102 may then determine that the movement of the object 104 indicates the occurrence of a movement to track. This step may be carried out in a similar fashion to step 404 of the spatial orientation process 400, as described above.

Next, at step 426, the sensor module 102 may record movement data in response to identifying a movement to track. In one embodiment, movement of the object 104 is recorded based on acceleration data captured by the acceleration sensor 116 of the sensor module 102. In another embodiment, movement of the object 104 is recorded based on magnetic field data captured by the magnetic field sensor 118 of the sensor module 102. In yet another embodiment, movement of the object 104 is recorded based on both acceleration data and magnetic field data.

Next, at step 428, the sensor module 102 may determine a correlation between the recorded movement data and a characteristic. In one embodiment, this determination may be based on correlation information stored in a data structure, such as a lookup table.

A lookup table is a data structure, usually an array or associative array, often used to replace a runtime computation with a simpler array indexing operation. The savings in terms of processing time can be significant, since retrieving a value from memory is often faster than undergoing relatively processing-expensive computation or input/output operation. Lookup table figures may be pre-calculated and stored in static program storage or pre-fetched as part of a program initialization phase.

The nature of the correlation may depend on the particular application and algorithms used to establish the correlation. Also, the nature of the characteristic may change based on the athletic activity that the individual 100 is participating in, as well as particular object 104 that is being monitored. In one embodiment, the characteristic may relate to, for example, a speed, a jump height, a jump force, a jump distance, a jump trajectory, an athletic activity force, an athletic activity distance, an impact force, a characterization of a specific type of athletic movement, or a reaction time measurement. In other embodiments, the characteristic may be, for example, the rate of rotation, the plane of rotation, the jump force, force profile (force acting upon the body of the athlete or the ground or the object), or gait characteristics. As discussed above, the object in some embodiments may be an article of footwear, and the motion may include running, walking, jogging, and the like. In some embodiments the spatial orientation change detected may be utilized for correlating gait characteristics such as foot strike type, rate of pronation, degree of pronation, and the like.

FIG. 16C discloses an example of a characteristic table. In some embodiments, the recommendation may include utilization of a graphical display that classifies characteristics of the individual 100 into different categories, such as by using a classification table such as those shown in FIG. 16C. For example, a Heel Striker may be classified as such if the relevant angle measurement is greater than or about 5 degrees, a Midfoot Striker may be classified as such if the angle measurement is about −5 degrees to about 5 degrees, and a Forefoot Striker may be classified as such if the relevant angle measurement is less than or about 5 degrees. As an example of pronation classification, a Pronator may be classified as such if the relevant angle measurement is greater than or about 12 degrees, a Mild Pronator may be classified as such if the relevant angle measurement is about 5 degrees to about 12 degrees, a Neutral individual may be classified as such if the relevant angle measurement is between about −5 degrees to about 5 degrees, and a Supinator may be classified as such if the relevant angle measured is less than or about −5 degrees. In some embodiments, measured Pronation Rate may be a relevant third variable used in the classification table that may include individuals with high pronation rates, average pronation rates, or low pronation rates. In some embodiments, there may be no graphical display of the characteristic table.

In some embodiments, the described table may map the classification system to a shoe classification system. The shoe classification system may be a general classification system applied to multiple footwear brands, or may be proprietary in nature and specific to a particular brand of footwear. Depending on the classification of Foot Strike type, Pronation Angle, and Pronation Rate, the retail enhancement system may output a recommendation of a particular type of footwear such as stable, neutral, natural, fast, or the like.

In some embodiments, the function underlying the relationship between gait characteristic acceleration data and gait characteristics may be based on empirical data for the specific article of footwear.

Finally, at step 430, an output is provided that conveys the characteristic to the individual 100, a retailer 1000, or any other interested person. This step may be carried out in a similar fashion to step 412 of the spatial orientation process 400, as described above.

The analytical frameworks outlined with respect to FIG. 9 and FIG. 10 detailing the basic spatial orientation process 400 and the basic movement correlation process 420, respectively may be used in embodiments of the present invention to monitor the individual's 100 body or a piece of the individual's 100 athletic equipment using a sensor module 102. However, in some embodiments of the present invention, these basic analytical frameworks may include additional steps that may provide improved capabilities, thus offering the individual 100 engaged in athletic activities better tools to assess their activities.

FIG. 11 illustrates an active state process 440 that may be used to augment the basic spatial orientation process 400 or the basic movement correlation process 420 outlined above. The active state process 400 may enable a sensor module 102 to run in a plurality of states, one of which may be considered an active state. In one embodiment, the active state may be characterized by the sensor module 102 consuming more power during the active state than prior to the active state. In another embodiment, the active state may be characterized by the sensor module 102 sampling data from the acceleration sensor 116 at a higher rate during the active state than prior to the active state. In yet another embodiment, the active state may be characterized by the sensor module 102 permanently saving data in the active state, as opposed to only temporarily recorded data prior to the active state. In this way, enabling various states may allow the sensor module 102 to operate with reduced battery power, reduced processing power, or otherwise be more efficient.

With reference to FIG. 11, the active state process 440 begins as step 442. In one embodiment, the steps of the active state process 440 may occur just prior to the steps of the basic spatial orientation process 400 or the basic movement correlation process 420 so that these processes may be carried out with more efficient sensor module 102 function.

At step 442, the sensor module 102 may detect movement of the object 104 at a first time. This step may be carried out in a similar fashion to step 402 of the spatial orientation process 400 or step 422 of the movement correlation process 420, as described above.

Next, at step 444, the sensor module 102 may determine that the movement of the object 104 corresponds to a predetermined activation movement. In some embodiments, the predetermined activation movement may include a series of discrete movements such as, for example, the individual 100 jumping up and down three times in series, or a movement that results in the acceleration of the sensor module 102 exceeding and/or falling below a predetermined threshold in absolute terms or for a predetermined period of time. In one embodiment, movement of the object 104 is detected based on acceleration data captured by the acceleration sensor 116 of the sensor module 102. In another embodiment, movement of the object 104 is detected based on magnetic field data captured by the magnetic field sensor 118 of the sensor module 102. In yet another embodiment, movement of the object 104 is detected based on both acceleration data and magnetic field data. In some embodiments the predetermined activation movement may include a certain number of steps taken, strides taken, jumps, leg lifts, toe taps, or other lower body movement.

The step of determining that the movement of the object corresponds to a predetermined activation movement may include comparing acceleration data associated with the predetermined activation movement to acceleration data detected in association with the movement of the object. Alternatively, the step of determining that the movement of the object corresponds to a predetermined activation movement may include comparing timing data associated with the predetermined activation movement to timing data detected in association with the movement of the object.

In some embodiments, the monitored object 104 can be considered stationary when the sensor module 102 of the monitored object 104 senses resultant acceleration of about 1G (i.e., resultant acceleration within a threshold tolerance of 1G, for example, within 5% of 1G). In some embodiments the monitored object 104 can be considered stationary at times while the individual is standing still.

Next, at step 446, after determining that an activation movement has occurred, the sensor module 102 may enter the active state. As previously described, the active state may be characterized, for example, by the sensor module 102 consuming more power or sampling data at a higher rate during the active state than prior to the active state.

Finally, at step 448, upon the sensor module 102 entering the active state, detection of movement of the object at a second time, as detailed at step 402 of the basic spatial orientation process 400 or at step 422 of the basic movement correlation process 420. In this way, enabling various states may allow the sensor module 102 to operate with reduced battery power, reduced processing power, or otherwise be more efficient.

FIG. 12 illustrates a reference motion process 450 that may be used to augment the basic movement correlation process 420 outlined above. The reference motion process 450 may enable a sensor module 102 to identify a matching athletic motion from a plurality of reference motions by comparing movement data, where the plurality of reference motions may be diverse in nature. In this way, the athletic motion identification capabilities of the movement correlation process 420 may be enhanced by enabling identification and tracking of diverse types of motions executed during an activity. As discussed above, the object in some embodiments may be an article of footwear, and the motion may include running, walking, jogging, and the like. In some embodiments the spatial orientation change detected may be utilized for correlating gait characteristics such as foot strike type, rate of pronation, degree of pronation, and the like.

With reference to FIG. 12, the reference motion process 450 begins as step 452. In one embodiment, the steps of the reference motion process 450 may effectively be substituted for step 426, 428, and 430 of the basic movement correlation process 420 outlined above so that the correlation and identification capabilities are enhanced.

At step 452, the sensor module 102 may record movement data (possibly in response to identifying a movement to track in a previous step, as outlined above). In one embodiment, movement of the object 104 is recorded based on acceleration data captured by the acceleration sensor 116 of the sensor module 102. In another embodiment, movement of the object 104 is recorded based on magnetic field data captured by the magnetic field sensor 118 of the sensor module 102. In yet another embodiment, movement of the object 104 is recorded based on both acceleration data and magnetic field data.

Next, at step 454, the sensor module 102 may identify a matching athletic motion from a plurality of reference motions by comparing the movement data to data associated with the plurality of reference motions. In one embodiment, as with step 428 of the basic movement correlation process 420, the identification may be made at least in part based on correlation information stored in a data structure, such as a lookup table.

Particular to step 428, identification of the matching athletic motion may be by reference to a plurality of reference motions. In other words, at step 428, the system is not limited to looking for a motion that matches a single motion (e.g., raising one foot and then the other). In some embodiments, the system is not limited to looking for a motion that matches a single class of motions (e.g., running as opposed to walking) In other embodiments, the system is not limited to looking for a motion that matches motions in a single sport (e.g., sprinting).

In one embodiment, one or more of the reference motions may include a series of discrete movements. In some embodiments, data associated with the plurality of reference motions may include acceleration data, magnetic field data, and/or timing data. Of course, the nature of the identifying matching athletic motion may depend on the particular application and algorithms used to establish the match. Also, the nature of the matching athletic motion may change based on the athletic activity that the individual 100 is participating in, as well as particular object 104 that is being monitored.

Finally, at step 456, an output is provided that conveys the matching athletic motion to the individual 100, a retailer 1000, or any other interested person. This step may be carried out in a similar fashion to step 430 of the movement correlation process 420, as described above. In this way, the athletic motion identification capabilities of the movement correlation process 420 may be enhanced by enabling identification and tracking of diverse types of motions executed during an activity.

FIG. 13 illustrates a remote spatial processing process 460 that may be used to augment the basic spatial orientation process 400 outlined above. The remote spatial processing process 460 may enable a sensor module 102 to wirelessly transmit spatial orientation data to a remote computer for processing. Wireless communication with other elements of the retail enhancement system 10 is generally described above. In this way, the spatial processing capabilities or movement correlation capabilities of the retail enhancement system 10 may be enhanced by shifting certain processing and analytical tasks to a remotely located computer, such as a server computer, with greater computational abilities and, in some embodiments, access to additional data or other resources.

With reference to FIG. 13, the remote spatial processing or correlation process 460 begins as step 462. In one embodiment, the steps of the remote spatial processing or correlation process 460 may effectively be substituted for step 410 of the basic spatial orientation process 400, or step 426 of the basic movement correlation process 420, outlined above so that characteristic determination may occur remotely.

At step 462, a change in the spatial orientation of the object 104 may be determined or movement data may be recorded. In some embodiments, the determination of the change in the spatial orientation of the object 104 or the recordation of movement data at step 462 may be made similarly to the determination of the change in spatial orientation of the object 104 at step 408 of the basic spatial orientation process 400 outlined above or to the recording of movement data at step 426 of the basic movement correlation process 420.

Next, at step 464, the sensor module 102 may wirelessly transmit data relating to the change in spatial orientation, or to movement, to a computer, wherein the computer is remotely located from the user during the athletic activity. For example, the remote computer may be server 202. In one embodiment, the data relating to the change in spatial orientation, or to movement, may be transmitted to the remote computer during the athletic activity. In another embodiment, the data relating to the change in spatial orientation, or to movement, may be transmitted to the remote computer after the athletic activity has been completed.

Next, at step 466, the sensor module 102 may wirelessly receive characteristic data from the remote computer, wherein the characteristic data is based on the transmitted data relating to the change in spatial orientation, or to movement. Accordingly, the determination of the characteristic, as outlined, for example, at step 410 of the basic spatial orientation process 400, the determination of the characteristic based on correlation data, possibly with reference to a lookup table, as outlined, for example, at step 428 of the basic movement correlation process 420, may be handled by the remote computer. In one embodiment, the characteristic data may be received from the remote computer during the athletic activity. In another embodiment, the characteristic data may be received from the remote computer after the athletic activity has been completed. As discussed above, the object in some embodiments may be an article of footwear, and the motion may include running, walking, jogging, and the like. In some embodiments the spatial orientation change detected may be utilized for correlating gait characteristics such as foot strike type, rate of pronation, degree of pronation, and the like.

In addition, in certain embodiments, because of the greater processing capabilities and resources of the remote computer, the remote computer may be capable of providing additional information to the sensor module 102. In one embodiment, the sensor module 102 may receive training recommendation data from the remote computer in addition to the characteristic data. In another embodiment, the sensor module 102 may receive motivational content data from the remote computer in addition to the characteristic data.

In some embodiments, the characteristic data received from the remote computer may include a comparison between data associated with the user for the present athletic activity and data associated with the user from a previous athletic activity. In another embodiment, the characteristic data received from the remote computer may include a comparison between data associated with the user for the present athletic activity and data associated with a different individual's athletic activity.

Finally, at step 468, an output is provided that conveys the characteristic to the individual 100, a retailer 1000, or any other interested person. This step may be carried out in a similar fashion to step 412 of the spatial orientation process 400, or to step 430 of the movement correlation process 420, as described above. In this way, the spatial processing or movement determining capabilities of the retail enhancement system 10 may be enhanced by shifting certain processing and analytical tasks to a remotely located computer, such as a server computer, with greater computational abilities and, in some embodiments, access to additional data or other resources.

FIG. 14 illustrates a location process 480 that may be used to augment the basic spatial orientation process 400 or the basic movement correlation process 420 outlined above. The location process 480 may enable an individual to determine the precise geographic location that various monitored athletic motions occurred during the course of an athletic activity. In this way, the location process 480 may provide the individual, a retailer 1000, or any other interested person with additional information that may be correlated with the movement-based characteristic information itself.

With reference to FIG. 14, the location process 480 begins as step 482. In one embodiment, the steps of the location process 480 may occur after the steps of the basic spatial orientation process 400 or the basic movement correlation process 420, or just prior to the output steps of these processes.

At step 482, the characteristic may be determined based on a change in the spatial orientation of the object 104, as described at step 410 of the spatial orientation process 400, or based on the correlation described at step 428 of the movement correlation process 420.

Next, at step 484, the location of the object 104 during the athletic activity may be determined. In one embodiment, the location of the object 104 during the athletic activity is determined using a satellite positioning system receiver, such as a GPS, Galileo, BeiDou, or GLONASS receiver. In another embodiment, the location of the object 104 during the athletic activity is determined using a beacon signal or radio signal triangulation.

In embodiments where the individual's 100 physical activity includes traversing a specific route (e.g., running or walking), the sensor module 102 may capable of recording an individual's 100 geographic way points along the route traversed.

Finally, at step 486, a determined athletic characteristic may be correlated with the location associated with the athletic characteristic. Accordingly, for example, the sensor module 102 may capable of recording where an individual 100 traversed particular environment or terrain (e.g. pavement, grass, incline, decline, sloped). This may be factored into the recommendation regarding an article of footwear.

FIG. 15 shows a flowchart for a method for feedback of a recommendation of an article of footwear according to an embodiment of the present invention. In some embodiments, the method may begin with providing the sensor module 102 (e.g. motion sensor). Next, the sensor module 102 (e.g. motion sensor) may be attached to the individual 100. After that, data may be recorded during a first athletic activity. The data may then be received to the system, analyzed, and characteristics (such as gait characteristics may be determined. The individual then may be provided with a recommendation and confirm a previously determined characteristic. There may then be a decision step, where the system or method may ask whether a confirmation athletic activity (e.g. confirmation run) is desired. If yes, the system and method may go back to the step where the sensor module 102 (e.g. motion sensor) is attached to the individual 100 and run through the method and system a second time. If no confirmation run is desired, the system and method for providing feedback of a recommendation of an article of footwear may end.

By using the retail enhancement system 10 including the sensor module 102 described above, embodiments of the present invention may advantageously enable the individual 100 (or their coach, teammate, a spectator, or retailer 1000) to obtain this or other information about the motion of the individual's 100 body or the motion of a piece of the individual's 100 athletic equipment during or after the course of the athletic activity.

While various embodiments of the present invention are described in the context of the running, the present invention is not so limited and may be applied in a variety of different sports or athletic activities including, for example, sports of soccer (i.e., football), basketball baseball, bowling, boxing, cricket, cycling, football (i.e., American football), golf, hockey, lacrosse, rowing, rugby, running, skateboarding, skiing, surfing, swimming, table tennis, tennis, or volleyball, or during training sessions related thereto. In some embodiments, the retail enhancement system may make recommendations regarding articles of apparel or other sports equipment in addition to, or in substitution of articles of footwear.

As a non-limiting example, in an embodiment, sensor module 102 embodiments such as those described above may enable an individual 100, coach, teammate, retailer 1000, or a spectator to determine, for example, characteristics of a tennis player's motion. For example, a sensor module 102 may be attached to a tennis racquet to measure characteristics of the swinging racket. Based on these measurements and other personal information regarding the individual, the retail enhancement system 10 may make a recommendation regarding a specific racquet.

For running, sensor module 102 embodiments such as those described above may enable an individual 100, coach, teammate, retailer 1000, or a spectator to determine, for example, characteristics of a runner's motion. For example, a sensor module 102 could be used to determine the speed, pace, distance traversed, locations traversed, or to discriminate between different surfaces (e.g., grass, street, or trail) and inclinations (e.g., uphill, flat, or downhill). In some embodiments the sensor module 102 may be mounted, for example, on a runner's torso, arm, hand, leg, foot, or head, or on or in their article of footwear.

In some embodiments of the present invention, the sensor module 102 may be capable of compensating for inherent deficiencies that may be present for various types of sensor contained within or in communication with the sensor module 102. Most real world sensors have limitations. For example, accelerometers, magnetometers, and gyroscopes may have accuracy issues, particularly when used at speeds of motion of the object 104 or under other conditions that differ from their initial calibration conditions.

In some systems, if sensor data, such as acceleration sensor 116 or magnetic field sensor 118 data, is temporarily lost or otherwise unavailable, the data from the unavailable sensor is not used in subsequent processing or calculations. In other systems, lost data may be estimated by "straight line" methods where, for example, it is assumed that the data stays constant or changes at a constant rate. However, in some embodiments of the present invention sensor data, such as one of acceleration sensor 116 or magnetic field sensor 118 data may be used to compensate for and/or estimate the changes in the other of acceleration sensor 116 or magnetic field sensor 118 data based on known, derived, or estimate correlations between the two types of data, or data extrapolation.

By combining the data produced by, for example, acceleration sensor 116 and a magnetic field sensor 118, systems and methods according to embodiments of the present invention are able to more accurately determine absolute data values or characteristics even when data from one of the acceleration sensor 116 or the magnetic field sensor 118 is lost for any reason. Using the data that is not missing, the system can continue to provide data values or characteristics to fill in the "holes" until the missing data is regained or otherwise again sampled.

In other embodiments of the present invention, angular momentum sensor 124 data, such as gyroscope data, may be used in combination with one or more of acceleration sensor 116 or magnetic field sensor 118 data for data calibration and/or extrapolation.

In some embodiments of the present invention, calibration and/or generation of correction factor data for an acceleration sensor 116 or magnetic field sensor 118-based sensor modules 102 may be performed under a variety of different use conditions, e.g., calibration data or correction factors may be generated for use at different movement speeds, for use with an individual's 100 body, with a piece of athletic equipment, for use in different sports, for use under different wind conditions, for use under different court or field conditions, etc. Moreover, this variety of correction factors and/or calibration data may be collected, in the background, over time, as the individual 100 continues using the system. In this manner, a "lookup table" or other "universe" or library of calibration data or correction factors may be built up and stored in the monitoring/retail enhancement system (optionally in the portion of the system), such that an appropriate correction factor could be generated and applied for a full range of individual 100 or athletic equipment speeds and/or other use conditions.

A microprocessor provided with the retail enhancement system 10 (optionally in the portion of the system, in the personal computer, electronic device 306, sensor module 102, etc.) may be programmed to interpolate between and/or extrapolate from known calibration or correction factors to arrive at the most appropriate calibration or correction factor for use at any speed or other use condition(s). Also, in this manner, different calibration or correction factors may be applied at different times during a single athletic performance, e.g., based on the speed or other use conditions determined at a given time during the performance, to further help improve the overall accuracy of the speed and distance monitor. By having a variety of correction or calibration factors available under different performance conditions, the sensor module 102 will tend to become more accurate, particularly over time and with increased use, because of the increased number of calibration and correction factors generated with increased use.

In one embodiment of the present invention, the sensor module 102 may be affected by perturbations in local magnetic fields, such as the earth's magnetic field. Perturbation can be caused, for example, by objects with ferromagnetic structures. In some embodiments, the local magnetic field may be more variable at certain distances near the surface of the earth than at other distances further away from the earth. For example, the local magnetic field may be more variable or perturbed within approximately six feet of the surface of the earth than at more than approximately six feet away from the surface of the earth. Accordingly, in some embodiments, magnetic field sensor 118 data obtained from an object 104 when the object 104 is more than approximately six feet away from the surface of the earth may be used to extrapolate or otherwise estimate proper or likely magnetic field sensor 118 data from when the object 104 was within approximately six feet of the surface of the earth, if the magnetic field sensor 118 data from when the object 104 was within approximately six feet of the surface of the earth is otherwise deemed to be unreliable due to the relatively high variability in local magnetic fields, such as the earth's magnetic field, near the surface of the earth.

In some embodiments, a magnetic field sensor 118 may obtain data about the movement of the object 104 at a first time when the magnetic field sensor 118 is significantly influenced by a perturbed magnetic field. Then obtain data about the movement of the object 104 at a second time when the magnetic field sensor 118 is not significantly influenced by a perturbed magnetic field. After this data is captured, the sensor module 102 may determine that the data about the movement of the object 104 at the first time is not acceptable, and may estimate data about the movement of the object 104 at the first time based on the data about the movement of the object at the second time.

In various embodiments of the present invention described above, an individual 100 (or another interested person such as a retailer 1000, coach, teammate, or spectator) may obtain information about the motion of the individual's 100 body or the motion of a piece of the individual's 100 athletic equipment during the course of the athletic activity. Once a characteristic or specific athletic movement has been identified by the retail enhancement system 10, to the extent that the characteristic or specific athletic movement was not entirely optimal/correct, the retail enhancement system 10 may further be employed to train or coach the user to improve their characteristic or specific athletic movement in the future. Determinations of what characteristic value or specific athletic movement characteristic is optimal/correct may be made automatically by the retail enhancement system 10 based on predetermined values, algorithms, or other data stored in a database, look-up table, or the like, or the determination may be made by a live trainer, coach, the individual 100 themselves, or another interested person with access to the characteristic value or specific athletic movement data such as a retailer 1000.

It is possible to use sensor modules 102 such as those described above to obtain gait characteristics such as foot strike type, rate of pronation, degree of pronation, and the like using such methods. Based on these experimental data obtained by these methods, given a suitably large and representative sample and suitably precise measurement techniques, and assuming particulars regarding the energy transfer between the components, it is also possible to undertake a multi-variable regression analysis to link gait characteristics such as foot strike type, rate of pronation, degree of pronation, and the like to one another and with a recommendation to provide to an individual regarding an article of footwear. In other embodiments, other methods such as high speed video analysis can be used as well to obtain information regarding gait characteristics, and this information can be used to define the variables for a multi-variable regression analysis.

From the data collected, such as acceleration and magnetic field data, the retail enhancement system 10 may determine rolling plane of foot. The retail enhancement system 10 may also detect gait phases, such as rolling through a stance phase into a takeoff phase in a particular plane.

The retail enhancement system 10 may detect the orientation of the gravity vector at two different phases—at one point in time, the only force acting is gravity. Because of this, the gravity vector will appear as moving in the plane, with respect to the sensor module. This is a very short period of the gait cycle, and at other times, other forces perturb the gravity vector. The retail enhancement system 10 may calculate the cross product of the vector defining the plane, which will be perpendicular to the plane of motion and thus defining the plane of motion. At the same time the magnetometer may measure the magnetic field. Built into the calculation is the assumption is that the magnetic field in the location is constant, and does not change during this time period. The retail enhancement system 10 may then project the magnetometer vector on the accelerometer planes, and the result will include that any changes in magnetometer data will be due to movement of the foot in the article of footwear.

Similar calculations can be made to various axes of the sensor module's data, such as calculating pronation angle, and pronation rate, for example.

Once this data is captured and calculated the retail enhancement system 10 may classify the runners based on their running style, utilizing data analysis such as an anterior-posterior plot angle vs. time; medial-lateral plot angle vs. time; and the like. The retail enhancement system 10 may include calculations of these characteristic angles for many runners that may fall into different categories, such as heel strike, mid foot, forefoot, neutral, pronation, supinate, or some combination of characteristics. This angle data may be organized into a function that may match up to various categories. The function may include data analysis of gait characteristic maximums, inflection points, etc.

The gait analysis function may in some embodiments use a principle component analysis (PCA). A PCA transforms into a set that pulls out principle features that are important to the analysis. The gait analysis function may in some embodiments use other analyses, such as binary or multi-variate classification; regression analysis; brute force methods using basic biomechanics science; or some combination of analyses.

The gait analysis function may in some embodiments utilize personal information of individuals such as gender, shoe size, height, weight, running habits, prior injuries, etc.

This information may be stored in the sensor module 102, the electronic device 306, or a server. Storing the information in the sensor module 102 may be advantageous because in a busy retail environment it may reduce the opportunity for data paired to sensor modules 102 assigned to particular individuals to become mismatched.

Regression analysis is a statistical process for estimating the relationships among variables. Regression analysis can be used to fit a predictive model to an observed data set of values. After developing such a model, if additional values of one or more variables (e.g. gait characteristics such as foot strike type, rate of pronation, degree of pronation, and the like) can be determined, the fitted model can be used to make a prediction of the values of unknown variables, such as categories of articles of footwear that may be recommended. When building a suitable model, given variables that may be related, regression analysis can be applied to, for example, quantify the strength of the relationships between the various variables, to assess which variables may have no relationship at all, or to identify which subsets of the variables contain redundant information.

In one embodiment of the present invention, a linear regression analysis can be employed to predict the relationship between gait characteristics such as foot strike type, rate of pronation, degree of pronation, and the like. In linear regression, data are modeled using linear predictor functions, and unknown model parameters are estimated from the data, such as categories of articles of footwear that may be recommended. Exemplary results of a linear regression analysis correlating points of impact obtained empirically to points of impact determine from applying a linear regression function to sensor module 102 data are illustrated in FIG. 16A.

In another embodiment of the present invention, the regression analysis can alternatively rely on a tool known as a regression tree. A regression tree is a predictive model that maps observations about an item to conclusions about the item's target value. The goal is to create a model that predicts the value of a target variable based on several input variables. A tree can be derived by splitting the source set into subsets based on an attribute value test. This process is repeated on each derived subset in a recursive manner called recursive partitioning. The recursion is completed when the subset at a node has all the same value of the target variable, or when splitting no longer adds value to the predictions. A portion of an exemplary regression tree for correlating gait characteristics such as foot strike type, rate of pronation, degree of pronation, and the like is shown in FIG. 16B. In this figure, each x(n) variable represents one of the foot motion variables, while the leafs of the regression tree represent an outcome variable after applying the regression conditions for a given branch.

Once a regression analysis results in a model that establishes a relationship between gait characteristics such as foot strike type, rate of pronation, degree of pronation, and the like, measured or calculated values of some variables can be used to determine others that are unknown, such as categories of articles of footwear that may be recommended. In one embodiment of the present invention, data from a sensor module 102 may be used to determine gait characteristics such as foot strike type, rate of pronation, degree of pronation, and the like, for a given individual, and this data may be used to provide to an individual a recommendation regarding an article of footwear.

In one embodiment of the present invention, a regression analysis can be used to determine gait characteristics such as foot strike type, rate of pronation, degree of pronation, and the like based on acceleration data obtained from the sensor module 102. The acceleration data may be obtained from a sensor module 102, or from another source. In other embodiments, the regression analysis can be used to determine gait characteristics such as foot strike type, rate of pronation, degree of pronation, and the like based on other data such as magnetometer data, angular momentum sensor data, or multiple types of data.

In one embodiment of the present invention, the analysis can include other user-input information such as prior injury information, an athletic goal, intended athletic environment, intended athletic duration, and current athletic footwear. Other personal information may be used, such as height, weight, shoe size, and gender.

Each parameter determining steps may be conducted in accordance with the discussion provided above regarding obtaining these parameters. Finally, the regression analysis may determine the recommendation given to an individual about an article of footwear.

As noted above, the regression analysis may rely on a regression tree. A regression tree may be used when linear regression techniques do not yield suitable predictive results. The regression tree is a model that can predict determine gait characteristics such as foot strike type, rate of pronation, degree of pronation, and the like, for a given individual, and this data may be used to provide to an individual a recommendation regarding an article of footwear derived, in one embodiment, from acceleration data. In some embodiments, the regression tree can provide local data correlations that are not valid globally. The key is fitting a given set of input data into a particular portion of the regression tree where a good fit among the data can be found. For example, one branch of the regression tree may be a good fit for a gait with low pronation angle, high pronation rate, while another branch of the regression tree may be a good fit for a gait with high pronation rate and low pronation angle. Additional variables can be added to the analysis in various branches of the tree. But at some point, adding new variables requires significantly more data analysis while giving little added accuracy. In other words, at some point continuing to split new branches of the tree no longer adds value to the predictions.

In some embodiments of the present invention, the sensor module 102 may communicate with other components of the retail enhancement system 10 via wired or wireless technologies. Communication between the sensor module 102 and other components of the retail enhancement system 10 may be desirable for a variety of reasons. For example, to the extent that the sensor module 102 records and stores athletic activity information, it may be useful to transmit this information to another electronic device for additional data processing, data visualization, sharing with others, comparison to previously recorded athletic activity information, or a variety of other purposes. As a further example, to the extent that the sensor module 102 has insufficient processing power, wide area network transmission capabilities, sensor capabilities, or other capabilities, these capabilities can be provided by other components of the retail enhancement system 10. With this in mind, possible communications means are described briefly below.

Wired communication between the sensor module 102 and an electronic device 306 may be achieved, for example, by placing the sensor module 102—or a piece of athletic equipment 104 including the sensor module 102—in a docking unit that is attached to the electronic device 306 using a communications wire plugged into a communications port of the electronic device 306. In another embodiment, wired communication between the sensor module 102 and the electronic device 306 may be achieved, for example, by connecting a cable between the sensor module 102—or a piece of athletic equipment 104 including the sensor module 102—and the computer 304. The data port 132 of the sensor module 102 and a communications port of the computer 304 may include USB ports. The cable connecting the sensor module 102 and the computer 304 may be a USB cable with suitable USB plugs including, but not limited to, USB-A or USB-B regular, mini, or micro plugs, or other suitable cable such as, for example, a FireWire, Ethernet or Thunderbolt cable. As previously explained above, in some embodiments, such cables could be used to facilitate power transfer to a power source 112 of the sensor module 102, in order to charge the power source 112. Alternatively, the power source 112 may be recharged by inductive charging, or by using a docking station with a charging base 200.

Wired connection to an electronic device 306 may be useful, for example, to upload athletic activity information from the sensor module 102 to the electronic device 306, or to download application software updates or settings from the electronic device 306 to the sensor module 102.

Wireless communication between the sensor module 102—or a piece of athletic equipment 104 including the sensor module 102—and the electronic device 306 may be achieved, for example, by way of a wireless wide area network (such as, for example, the Internet), a wireless local area network, or a wireless personal area network. As is well known to those skilled in the art, there are a number of known standard and proprietary protocols that are suitable for implementing wireless area networks (e.g., TCP/IP, IEEE 802.16, Bluetooth, Bluetooth low energy, ANT, ANT+ by Dynastream Innovations, or BlueRobin). Accordingly, embodiments of the present invention are not limited to using any particular protocol to communicate between the sensor module 102 and the various elements of the retail enhancement system 10 of the present invention.

In one embodiment, the sensor module 102—or a piece of athletic equipment 104 including the sensor module 102—may communicate with a wireless wide area network communications system such as that employed by mobile telephones. For example, a wireless wide area network communication system may include a plurality of geographically distributed communication towers and base station systems.

Communication towers may include one or more antennae supporting long-range two-way radio frequency communication wireless devices, such as sensor module 102. The radio frequency communication between antennae and the sensor module 102 may utilize radio frequency signals conforming to any known or future developed wireless protocol, for example, CDMA, GSM, EDGE, 3G, 4G, IEEE 802.x (e.g., IEEE 802.16 (WiMAX)), etc. The information transmitted over-the-air by the base station systems and the cellular communication towers to the sensor module 102 may be further transmitted to or received from one or more additional circuit-switched or packet-switched communication networks, including, for example, the Internet.

As previously noted, in some embodiments of the present invention, a having a sensor module 102 may communicate with an electronic device 306 of the retail enhancement system 10, such as a smart phone, that is also carried by the individual 100 during the athletic activity. As illustrated by FIGS. 17-25 various software modules of a motion monitoring electronic device 306 software of the present invention may support graphical user interfaces (GUIs) through which an individual 100 can interact with the retail enhancement system 10.

In some embodiments of the present invention, the electronic device 306 may take the form of a mobile phone and may include at least a processor, a memory, user input controls, a positioning system receiver, a wireless wide area network (WWAN) transceiver, a visual display, and an audio unit. A visual display in the form of a LCD screen, and user input controls in the form of a physical keyboard and a scroll ball may be present.

The memory of the electronic device 306 may be adapted to store application programs used to implement aspects of the functionality of the retail enhancement system 10 described herein, such as a retail enhancement system 10 electronic device 306 software application. Thus, the application software may be stored, for example, in the memory of the electronic device 306. Alternatively, those of skill in the art will understand that all or part of the software may be stored on the server 302 and accessed over the network 300 and run remotely as a mobile web application.

This retail enhancement system electronic device 306 software application includes a number of different software modules capable of providing motion monitoring services to individuals 100 using articles of footwear or other pieces of athletic equipment equipped with sensor modules 102. In one embodiment of the present invention, these modules include an athletic activity it module, a get better module, a challenges module, and a record book module. Each module may support one or more GUIs capable of being presented to an individual 100 using the retail enhancement system 10.

A GUI may offer, for example, graphical elements, visual indicators, and/or text to represent information and actions available to the individual 100. The individual 100 may use a physical input device, such as keyboard or scroll ball to interact with the GUI of the electronic device 306. Alternatively, the individual 100 may use a touch screen to interact directly with what is displayed. Various touch screens such as, for example, resistive or capacitive touch screens, may be employed.

Those skilled in the art will appreciate that alternative or additional software modules and sub-modules may be implemented in order to provide or extend the described or additional functionalities to the individual 100 using the electronic device 306. For example, the software configuration of software stored on an electronic device 306 may include a device operating system, which may be one of the commercially available mobile phone operating systems such as, for example, BlackBerry OS, iPhone OS, Windows Mobile, Symbian, LINUX, WebOS, or Android. The device operating system may also have an associated application programming interface through which middleware and application programs may access the services of the operating system.

The various modules of the retail enhancement system 10 of the present invention may support GUIs through which an individual 100 can interact with the retail enhancement system 10 using the electronic device 306 just prior to and/or during an activity. As will be appreciated by those of skill in the art, in one embodiment the GUIs may be supported by a mobile device application being run on the electronic device 306. In another embodiment, the GUIs may appear as web pages provided by the server 302 via a website that may be accessible to the individual 100 over the network 300 using a web browser on their electronic device 306. The GUIs may be considered to be part of the methods or systems of the present invention.

In order to access the features of embodiments of the present invention just prior to or during a physical activity, the individual 100 using the electronic device 306 may power on their electronic device 306 if it is not already in a powered up state. In some embodiments, it may be necessary for the individual 100 to manipulate user input controls to enter retail enhancement system 10 mode to access the application software.

As illustrated in FIG. 17, an embodiment a module of a GUI may enable the retail enhancement system 10 may support multiple individuals 100 such as multiple runners in different parts or phases of a sales cycle. For example, one runner may be registering and inputting personal information into the electronic device 306, while another runner is out for a data collection run. In an embodiment, the parts or phases may include pre run, out running, completed run, and analysis. Other phases may be included as sub-phases, or phases not specific to running Certain embodiments may include other athletic activity phases. As an example, in an embodiment a pre run phase may include individuals 100 that are currently in the store and have not paired any sensor modules 104 yet. An out running phase may include individuals that have paired sensor modules 104. In some embodiments, this out running phase may only be shown on the electronic device 306 where the personal information was collected or input by the individual 100 or retailer 1000. A completed run phase may include individuals 100 that have returned from a run and that the sensor modules 104 are ready for data collection and download from the sensor modules 104. In some embodiments, this completed run phase may only be shown on the electronic device 306 where the personal information was collected. An analysis phase may include individuals 100 whose data has been downloaded from the sensor modules 104. In some embodiments, this analysis phase may only be shown on the electronic device 306 where the personal information was collected. Having subsequent phases only shown on the electronic device 306 where the specific individual's 100 personal information was collected may be advantageous because it will allow for continuity in the retail experience by pairing a particular retailer 1000 with a particular individual 100 and make it less likely in a busy retail environment to have data become lost, misplaced, or loaded onto a different electronic device 306. In some embodiments, the home screen of the electronic device 306 may be divided into different areas depending on what stage a particular individual is in the process. In some embodiments, phases may be added as they are needed, and empty phases may not be shown on the electronic device 306.

In some embodiments, individuals may be identified by customer icons, which may include a gender icon, or a photo of the individual. The customer icon may also include customer specific info such as how long an individual has been running, name, and the like. In some embodiments, individuals may be able to be deleted from the electronic device 306 from the phase screen.

In some embodiments, there may be an introduction animation for first time use of the retail enhancement system 10. There may also be a setup and tutorial for first time use by the retailer 1000 or individual 100. Additionally there may be a walkthrough section that may include step-by-step instructions explaining the process of the retail enhancement system. In some embodiments, the retail enhancement system 10 may automatically select the language and localization of the retail environment based on the electronic device 306 characteristics, IP address, GPS location, or the like. The retail enhancement system 10 may also allow for default language preferences to be changed in a settings menu.

As illustrated in FIG. 18, the first time the retail enhancement system application is launched, a start module 3100 may prompt the individual 100 or retailer 1000 to, for example, select a preferred language, enter a password to proceed, link their electronic device 306 to a web account previously set up via the server 302. The individual 100 may also be prompted to enter information such as, for example, preferred unit preferences, personal information such as the individual's 100 age, height, weight, and sex, and/or the individual's 100 desired voice training options. The start module 3100 may have a new user icon which users may select to enter their information, or retailers may enter information about the retail environment. Additionally, the GUI may have sensor indicators 3004 that are used to indicate sensor status (e.g. on/off, low battery, collecting data, charging, paired to system, etc.). The start module 3100 may present a menu 3101, as illustrated in the illustration of the style module 3200 shown in FIG. 19A. During subsequent launches of the software application, the menu 3101 may be presented to the individual 100 immediately upon launch. The menu 3101 may include several icons or indicia corresponding to the style, run, learn, and article of footwear, as well as icons or indicia corresponding to settings or help features, as illustrated in subsequent figures. After launching the application software, the individual 100 may cause different GUI pages to be provided by different modules by selecting their corresponding icons using user input controls. Additional icons corresponding to sub-modules or program wizards associated with a particular module may pop up or otherwise be displayed to the individual 100 if the individual 100 selects, swipes, or hovers over a module icon with a cursor.

In some embodiments there may be an educational section. In some embodiments this may include information general to health and fitness, or more specialized information, such as information about running or a particular athletic activity.

In some embodiments, there may be a footwear gallery section, where an individual 100 or retailer 1000 may search through a catalog of articles of footwear without use of the sensor modules 104, or collecting of any data. In some embodiments, the retail enhancement system may retrieve returning customers information (individuals 100). In some embodiments, the system may archive customer information in an acceptable way to allow for more storage room on the electronic device 306 or sensor module 104. Archival may include hard drive storage on site, cloud based storage, server storage, or any other acceptable storage medium.

FIG. 19A is an exemplary GUI window that may be provided by the style module 3200. This GUI window may display a type of athletic activity icon set that may be used to convey various pieces of information to the individual 100, and from which the individual 100 can select types of activity the articles of footwear will be used for (e.g. for enjoyment, for training for a race, to stay healthy, to lose weight, and training for sports). Another section of the style module 3200 may include selection icons for the types of surfaces that the article of footwear will be used on (e.g. road/sidewalk, treadmill, trail, and everywhere). In either case, individuals may be able to select multiple icons to denote intended environment and use. Another section of the style module 3100 may include selection icons for duration of activity (e.g. less than thirty minutes, thirty minutes to an hour, and more than one hour).

Other examples of athletic goals may include training for a race, or other sporting event, improving individual fitness, simply enjoy running, or the like. Frequency intervals may include for example about 1-2 times per week, about 3-4 times per week, about 5-7 times per week, or the individual doesn't know. Length intervals may include for example about less than about 5 miles per week, about 5-10 miles per week, about 10-20 miles per week, greater than about 20 miles per week, or the individual doesn't know. Examples of intended athletic terrain environments may include roads, track, treadmill, trail, gym, or particular athletic fields designed for a specific sport. Examples of athletic equipment preferences may include for example more cushioning, less weight, better fit, strength, durability, intended athletic activity range, balance, weight balance, more color choices, and the like.

FIG. 19B is an exemplary GUI window that may be provided by the style module 3200 as a sub-module. All modules may have one or more sub-modules which may be navigated to and from by clicking, swiping, etc. The style sub-module shown in FIG. 19B may allow the individual 100 to select a brand, type, and line of article of footwear that the individual would like to replace.

FIG. 19C is an exemplary GUI window that may be provided by the style module 3200 as a sub-module. The style sub-module illustrated in FIG. 19C may allow the individual 100 to select a location of any prior injuries within a certain period of time. The style sub-module may have selection icons corresponding to particular body parts. In some embodiments, the style sub-module may display a graphical representation of an individual or avatar, and allow the individual 100 to directly select the particular area with a previous injury on the graphical representation. In some embodiments, the system may allow the individual 100 or retailer 1000 to one of upload photos, videos, medical records, and the like for incorporation into the retail enhancement system and methods.

Before the individual 100 can begin to use the retail enhancement system 10, they must successfully pair the electronic device 306 to a sensor module 102. Pairing is a process used in computer networking that helps set up an initial linkage between computing devices to allow communications between them. Pairing may occur wirelessly via a personal area network or local area network using, for example, the Bluetooth wireless protocols. The GUI may prompt the individual 100 or retailer 1000 to pair their electronic device 306 to a sensor module 102 as shown in FIGS. 20A-20C, and may display updates to the individual 100 or retailer 1000 as to the status of the pairing.

Sensor modules may have a generic registration name in the system that identifies the sensor module as part of the system. Once paired, sensor modules may be identified by the name of the individual using that sensor module. For example a sensor might be registered as RSS0005 as a generic identification name, and the broadcast signal would include this name. Once paired that sensor module may change the broadcast signal to include a name corresponding to the particular individual using that sensor module, such as RICH01 or RICH02. In this way, retailers 1000 will know which individual 100 by name is in certain phases of using the retail enhancement system 10.

Once the sensor modules 102 are paired, the registration data and personal information collected from the individual 100 may be loaded onto the sensor modules. In an embodiment, when the individual 100 returns to the retail environment, the sensor modules 102 may broadcast his or her name i.e. RICH01 and any available retailer 1000 or clerk will see this on the electronic device 306 and be able to help complete the other phases of the retail enhancement system 10. In an embodiment, this may trigger the registration and personal information to be transferred to the electronic device 306. Additionally, the analysis data captured by the sensor module 102 may be transferred to the electronic device at this time. The data may be transferred either with or without prompting of the individual 100 or retailer 1000. In other words, the data transfer may be either manual or automatic.

Updates may include notifying the individual 100 or retailer 1000 that the electronic device 306 is attempting to connect to the sensor module 102, that a connection has been made, or that a connection cannot be made. In one embodiment, these prompts or notifications may appear in the GUI window as shown in FIG. 20A. In one embodiment, the sensor module 102 may indicate that the sensor module 102 is ready to match, matched and ready for a run, that a run has been completed and is ready for upload, that the upload is in progress, and that there is low battery, and there may be a GUI window that explains this to the individual 100 or retailer 1000, such as illustrated in FIG. 20C.

Once the sensor module 102 is paired, the individual 100 may begin to use the retail enhancement system 10 by engaging in an athletic activity such as walking or running. In one embodiment, the sensor module 102 or the electronic device may indicate to the individual that they have engaged in sufficient athletic activity to analyze the data being captured by the sensor module 102. Once the individual has completed the athletic activity, the data captured by the sensor module 102 may be transferred to the electronic device by any of the ways described above. In some embodiments, the retail enhancement system 10 may notify the individual through either the electronic device 306 or sensor module 104 that enough data has been collected for the system to analyze and output a recommendation. This may be in the form of a visual display, flashing lights, text output, audio output, and may be in the form of notification on the electronic device 306, sensor module 104, or even another device carried by the individual, such as a personal mobile phone, smart watch, or other mobile electronic device. In some embodiments, the retail enhancement system 10 may notify the individual 100 to come back to the retail environment for data upload via an email, text message, voice message, or the like that may be transmitted and received by the individuals personal mobile phone, smart watch, or other mobile device.

During the data transfer, the GUI transfer module may display the status of data loading and calculations as shown in FIG. 21. The GUI window may indicate that it is measuring coordinates of gait characteristics such as rate of pronation, degree of pronation, foot strike type, and the like. In one embodiment, there may be a measurement visualization window that may display certain graphical information regarding the gait characteristics. In one embodiment, this graphical information may include scientific information regarding these gait characteristics. In another embodiment, this graphical information may include displays of the individuals body mechanics overlayed onto an avatar to visualize particular gait characteristics in an animation.

FIG. 22A shows a GUI embodiment of a gait analysis result module. The gait analysis result module may include a portion dedicated to the left side of the individual 100 and a portion dedicated to the right side of the individual 100. The gait analysis result module may include information regarding the foot strike type, pronation angle, and pronation rate of each side of the individual. The gait analysis result module may include information regarding a categorical type of gait determined using various gait characteristics. One embodiment may include recommended article of footwear class based on gait characteristics, such as stability, neutral, cushion, and the like.

FIG. 22B shows a sub-module of a gait analysis result module, that may show a motion video of a representation of the runner's foot. In some embodiments, this representation may include the bone structure within the foot. In some embodiments, there may be visual overlays or visual guides to illustrate key points in the motion sequence, such as when the foot strikes the ground. In some embodiments, the user may be able to select different views, such as front, side, and rear. In other embodiments, the user may be able to zoom, pan, rotate, and drag within the window to view the representation from different angles. In some embodiments, the window will include playback controls, where the user may view a video representation, stop a video representation, move forward or backward in a video representation of the data analyzed. In some embodiments, there may be running data points showing instantaneous measurements and how they change throughout the gait cycle, such as pronation angle, pronation rate, and location of foot strike.

In some embodiments, modules and sub-modules may be available to the individual in real-time during completion of the athletic activity. The modules and sub-modules may be displayed in real-time so that for example the individual 100 may view the gait analysis while they are running on a treadmill and view the data update in real-time. In another embodiment, the real-time system may be used for demonstration purposes so that a store clerk or retailer 1000 could explain the system to individuals 100 while manipulating the sensor modules (102) and showing the resulting motion on the display.

FIG. 23A shows a GUI embodiment of an article of footwear finding module. In some embodiments the article of footwear finding module may organize recommended article of footwear by types of article of footwear such as stability, neutral, and cushion. In some embodiments, the article of footwear may be organized by other categories, such as brand, price point, etc. In some embodiments, the organization may be filtered such that it only displays article of footwear currently in-stock at that location for purchase. This may be accomplished through manual entry, or digital connection to a point-of-sale system, or inventory system.

FIG. 23B shows another GUI embodiment of an article of footwear finding module. This GUI embodiment may be complimentary to the article of footwear finding module shown in FIG. 23A or may be stand-alone. In some embodiments, the article of footwear finding module may explain why an individual's biomechanics point toward a category of article of footwear. In this regard, this system may serve as an educational tool. In other embodiments, there may be links on the article of footwear finding module for the individual to select that explains information such as the anatomy of an article of footwear, brand specific technology, and how to properly fit an article of footwear.

FIG. 24A shows a GUI embodiment of a feedback module. This module may show a user different article of footwear recommendations after a series of athletic activities. The recommendations may be made with the cumulative data gathered, or may be made after each set of data has been analyzed independently.

FIG. 24B shows another GUI embodiment of a feedback module. In these embodiments, the module may display confirmation that the recommended article of footwear created the anticipated result with respect to the individual's gait characteristics. If the article of footwear did not create the desired effect, the feedback module may display a message that the article of footwear did not have the anticipated result. In some embodiments, the individual may engage in an athletic activity with the same article of footwear again, and compare the two results again. In other embodiments, the individual may engage in an athletic activity with different article of footwear after a new recommendation is made.

FIG. 25 shows a GUI embodiment of a sale/post-sale module. In some embodiments, this module may have a communication section where the individual may have their data saved to a profile or sent to an email address for later review. In some embodiments, this module may have a summary section where summary information may be displayed about the individuals gait characteristics and recommendations. In other embodiments, this module may have a purchase section. The purchase section may include selecting whether an article of footwear has been purchased, or selecting an article of footwear to be purchased. The purchase section may include selections to scan a barcode, choose from a chart, or the like. The purchase section may include selection of the size of article of footwear.

FIG. 26 shows a conceptual diagram of a retail enhancement system according to an embodiment of the present invention. In some embodiments, the interface to the retail enhancement system 10 may be accessed remotely by individuals 100 such that they may complete their personal information entry and registration information entry online on an internet website, or app similar to that used on the electronic device 306. The app or website may be a limited version of the retail enhancement system 10 and may have certain limitations, such as it would show the personal information entry section, and a filter for articles of footwear. The individual's information may then be available for access at a retail environment through an electronic device 306, where data may be obtained with previously obtained information and filtered articles of footwear choices. Similarly, the individual may elect to purchase through the app or website without visiting a physical retail environment, and utilize a virtual retail environment.

In some embodiments, the retail enhancement system 10 may send an SMS link with analysis results, or email the analysis results to the individual 100 or other interested party. The links may similarly include marketing or promotional material, such as special coupons to purchase online (e.g. 10% discount, free expedited shipping, or the like).

In some embodiments, the GUI modules may provide a visual display to the individual 100 giving them feedback about the gait characteristics during their athletic activity. The GUI may include a statistical display bar that may provide, for example, information on the maximum impact, rates of pronation, and pronation angles, or other gait characteristics.

The GUIs may include a video element. The video element shown is an animation that represents the individual's gait in three dimension. In some embodiments the animation may start automatically, while in other embodiments the individual 100 must provide an input to the electronic device 306 to request that the video play. In one embodiment, the perspective of the animation may change such that the individual's 100 perspective may appear to rotate around the animation to provide a better perspective on the gait characteristics. In another embodiment the individual 100 may be presented with a selection icon 604 allowing the individual 100 to choose different animated views of the animation such as, for example, a front view, an angled view, or a side view.

Other visual displays giving feedback about the gait characteristics of the individual during their athletic activity may also be provided to the individual 100. In one embodiment, a swipe element may indicate to the individual 100 that swiping their finger across the display screen may lead to other pages that display additional feedback. In other embodiments, buttons, switches, links, or other elements may be substituted for a swipe element.

In some embodiments of the present invention, the retail enhancement system 10 may also include or interact with an interactive retail system or inventory system. The interactive retail system or inventory system could be, for example, presented to an individual 100 via a screen on the individual's 100 electronic device 306. The interactive retail system or inventory system could provide a platform for selecting and/or ordering products offered by the provider of the system. Based on the characteristic or specific athletic movement provided by the retail enhancement system 10, and/or based on any training or coaching provided, as described above, the interactive retail system or inventory system could suggest specific products or product lines that may be helpful to the individual 100 in improving their future performance. The retail enhancement system 10 or inventory system may also ensure that the products are available in the retailer's inventory. In some embodiments, personal data about the individual 100 stored by the retail enhancement system 10 may also be used in making the determination of suitable products or product lines.

In one embodiment, the characteristic or specific athletic movement data and/or any training or coaching provided may be used for the online customization of certain products. For example, this data can be used to customize an article of footwear, an article of compression clothing, a helmet, or other piece of clothing or athletic equipment to enable clothing or other equipment to help the individual 100 in improving their future performance. In some embodiments, customized products may have an unique styles, varied materials, or different accessories for the individual 100 to choose from. In some embodiments, the retail enhancement system 10 may recommend an article of footwear based upon the more severe characteristic. In this way, the gait characteristic that is potentially most harmful to the individual's performance or health may be addressed.

In some embodiments, the retail enhancement system 10 may be sold as a package, including a tablet computer, multiple sensor modules 102 for multiple individuals 100 (e.g. runners), and a charger.

In some embodiments, the recommendation may only include a single manufacturer's products. In other embodiments, it may include multiple manufacturer's products.

This retail enhancement system 10 may recognize and record repeat usage of the retail enhancement system 10 over time, number of times various individuals store their data into a profile and update that data, records of sales and whether this retail enhancement system 10 leads to increased sales. The retail enhancement system 10 may also be able to integrate with various social media platforms, allowing individuals to share with their social network data regarding their gait characteristics, their usage of the retail enhancement system 10, or articles of footwear or other athletic equipment they purchase after use.

In some embodiments, the retail enhancement system 10 may integrate to a consumer experience platform that may include educational information about footwear, athletic content, e-commerce, store locators, and advanced research and development efforts on the part of manufacturers. Additionally, in some embodiments, the data may be aggregated and analyzed into usable forms for either the retailer 1000, manufacturer, engineering team may be able to use to improve their function. For example, a retailer 1000 may be able to track which models of footwear sell well at the location, and may order categories according to that data. A manufacturer or engineering team may be able to track injuries and performance metrics related to gait characteristics and improve upon existing products according to the data collected.

Various aspects of the present invention, or any parts or functions thereof, may be implemented using hardware, software, firmware, tangible non-transitory computer readable or computer usable storage media having instructions stored thereon, or a combination thereof and may be implemented in one or more computer systems or other processing systems.

Program products, methods, and systems for providing retail enhancement services of the present invention can include any software application executed by one or more electronic devices 306. An electronic device 306 can be any type of computing device having one or more processors. For example, the electronic device 306 can be a workstation, mobile device (e.g., a mobile phone, personal digital assistant, tablet computer, or laptop), computer, server, compute cluster, server farm, game console, set-top box, kiosk, embedded system, a gym machine, a retail system or retail enhancement system or other device having at least one processor and memory. Embodiments of the present invention may be software executed by a processor, firmware, hardware or any combination thereof in a computing device.

In this document, terms such as "computer program medium" and "computer-usable medium" may be used to generally refer to media such as a removable storage unit or a hard disk installed in hard disk drive. Computer program medium and computer-usable medium may also refer to memories, such as a main memory or a secondary memory, which can be memory semiconductors (e.g., DRAMs, etc.). These computer program products provide software to computer systems of the present invention.

Computer programs (also called computer control logic) may be stored on main memory and/or secondary memory. Computer programs may also be received via a communications interface. Such computer programs, when executed, may enable computer systems of the present invention to implement embodiments described herein. Where embodiments are implemented using software, the software can be stored on a computer program product and loaded into a computer system using, for example, a removable storage drive, an interface, a hard drive, and/or communications interface.

Based on the description herein, a person skilled in the relevant art will recognize that the computer programs, when executed, can enable one or more processors to implement processes described above, such as the steps in the methods illustrated by the figures. In some embodiments, the one or more processors can be part of a computing device incorporated in a clustered computing environment or server farm. Further, in some embodiments, the computing process performed by the clustered computing environment may be carried out across multiple processors located at the same or different locations.

Software of the present invention may be stored on any computer-usable medium. Such software, when executed in one or more data processing device, causes the data processing device to operate as described herein. Embodiments of the invention employ any computer-usable or -readable medium, known now or in the future. Examples of computer-usable mediums include, but are not limited to, primary storage devices (e.g., any type of random access or read only memory), secondary storage devices (e.g., hard drives, floppy disks, CD ROMS, ZIP disks, tapes, magnetic storage devices, optical storage devices, MEMS, nanotechnological storage devices, memory cards or other removable storage devices, etc.), and communication mediums (e.g., wired and wireless communications networks, local area networks, wide area networks, intranets, etc.).

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments of the retail enhancement system described with reference to the figures will so fully reveal the general nature of the invention that others can, by applying knowledge within the skill of the art, readily modify and/or adapt for various applications such specific embodiments, without undue experimentation, without departing from the general concept of the present invention.

While various embodiments of the present invention have been described above, they have been presented by way of example only, and not limitation. It should be apparent that adaptations and modifications are intended to be within the meaning and range of equivalents of the disclosed embodiments, based on the teaching and guidance presented herein. It therefore will be apparent to one skilled in the art that various changes in form and detail can be made to the embodiments disclosed herein without departing from the spirit and scope of the present invention. The elements of the embodiments presented above are not necessarily mutually exclusive, but may be interchanged to meet various needs as would be appreciated by one of skill in the art.

It is to be understood that the phraseology or terminology used herein is for the purpose of description and not of limitation. The breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

The invention claimed is:

1. A retail enhancement system, comprising:
   a sensor module comprising:
     a sensor, the sensor comprising at least one of a magnetometer, an accelerometer, or an angular momentum sensor,
     wherein the sensor module is configured to be associated with a first individual and to obtain a data for the first individual relating to a physiological parameter of the first individual during a first athletic activity from the sensor, and is further configured to be separately associated with a second individual to obtain a data for the second individual relating to a physiological parameter of the second individual during a second athletic activity from the sensor,
     wherein the sensor module is configured to be removably attached to a first article of footwear to be worn by the first individual during the first athletic activity and is further configured to be removably attached to a first article of footwear to be worn by the second individual during the second athletic activity; and
   an electronic device that is separate from the sensor module, wherein the electronic device is a dedicated device in a retail environment and is configured to:
     register the first individual and the second individual;
     collect personal information of the first individual and the second individual regarding at least one of an athletic goal, an intended athletic environment or terrain, an intended athletic activity duration, an intended athletic activity frequency, or an intended athletic activity distance;
     separately associate the sensor module with the first individual and the second individual;
     receive the data for the first individual and the data for the second individual from the sensor module;
     determine a first characteristic about a gait of the first individual based on the data for the first individual, the first characteristic about the gait of the first individual comprising at least one of foot strike type, rate of pronation, or degree of pronation;
     provide a first recommendation about a second article of footwear to be worn by the first individual to the first individual based on the first characteristic about the gait of the first individual and the personal information of the first individual;
     determine a first characteristic about a gait of the second individual based on the data for the second individual, the first characteristic about the gait of the second individual comprising at least one of foot strike type, rate of pronation, or degree of pronation;
     provide a first recommendation about a second article of footwear to be worn by the second individual to the second individual based on the first characteristic about the gait of the second individual and the personal information of the second individual;
     prompt a retailer to enter information about the first individual related to the first athletic activity and the second individual related to the second athletic activity;
     prompt the retailer or the first individual to attach the sensor module to the first article of footwear to be worn by the first individual; and
     pair the sensor module to the electronic device.

2. The system of claim 1, wherein the electronic device is configured to receive the data for the first individual during the first athletic activity from the paired sensor module.

3. The system of claim 1, wherein the electronic device separately associating the sensor module with the first individual and the second individual comprises wirelessly connecting the sensor module with the electronic device.

4. The system of claim 1, wherein the sensor module is a first sensor module, and wherein the retail enhancement system further comprises a second sensor module.

5. The system of claim 4, wherein the first sensor module is configured to be removably attached to the first article of footwear to be worn by the first individual during the first athletic activity and the second sensor module is configured to be removably attached to a second article of footwear to be worn by the first individual during a second athletic activity performed by the first individual.

6. The system of claim 5, wherein the electronic device is configured to provide a second recommendation about a third article of footwear to be worn by the first individual to the first individual based on the data for the first individual during the first athletic activity and the second athletic activity performed by the first individual.

7. The system of claim 1, wherein a graphical user interface (GUI) of the electronic device is configured to simultaneously display data of the first individual and the second individual.

8. The system of claim 1, wherein the electronic device comprises a graphical display configured to identify the first individual by a first icon and the second individual by a second icon.

9. The system of claim 1, wherein the electronic device comprises a graphical display configured to allow the first individual to select an area on the first individual's body with a prior injury.

10. The system of claim 9, wherein the first recommendation about the second article of footwear to be worn by the first individual is further based on the area on the first individual's body with the prior injury.

11. The system of claim 1, wherein the electronic device comprises a graphical display configured to display an update as to a status of the pairing of the sensor module to the electronic device.

12. The system of claim 1, wherein the electronic device comprises a graphical display configured to display one or more sales phases of a sales transaction of the first individual.

13. The system of claim 12, wherein the one or more sales phases comprises at least one of a pre athletic activity phase, an athletic activity phase, a data collection and download phase, or an analysis phase.

14. The system of claim 13, wherein at least one of the athletic activity phase or the analysis phase is only displayed on the electronic device that collected the personal information of the first individual.

15. The system of claim 13, wherein the graphical display is configured to display one or more areas of the retail environment corresponding to the one or more sales phases.

16. The system of claim 1, wherein the electronic device is configured to notify the first individual that the data for the first individual has been collected such that the first recommendation about the second article of footwear to be worn by the first individual can be provided to the first individual.

17. The system of claim 1, wherein the sensor module is configured to notify the first individual that the data for the first individual has been collected such that the first recommendation about the second article of footwear to be worn by the first individual can be provided to the first individual.

18. The system of claim 1, wherein the electronic device is further configured to provide feedback to the first individual regarding the first characteristic about the gait of the first individual.

19. The system of claim 1, wherein the electronic device is further configured to separately associate the sensor module with the first individual and the second individual in different parts of a sales cycle.

* * * * *